(12) United States Patent
Keravala

(10) Patent No.: US 11,192,925 B2
(45) Date of Patent: Dec. 7, 2021

(54) MODIFIED AAV CAPSIDS AND USES THEREOF

(71) Applicant: Adverum Biotechnologies, Inc., Redwood City, CA (US)

(72) Inventor: Annahita Keravala, Palo Alto, CA (US)

(73) Assignee: Adverum Biotechnologies, Inc., Redwood City, CA (US)

( * ) Notice: Subject to any disclaimer, the term of this patent is extended or adjusted under 35 U.S.C. 154(b) by 861 days.

(21) Appl. No.: 15/788,446

(22) Filed: Oct. 19, 2017

(65) Prior Publication Data
US 2018/0127471 A1 May 10, 2018

Related U.S. Application Data

(60) Provisional application No. 62/410,291, filed on Oct. 19, 2016.

(51) Int. Cl.
| | | |
|---|---|---|
| C07K 14/005 | (2006.01) | |
| A61K 9/00 | (2006.01) | |
| A61K 48/00 | (2006.01) | |
| C12N 7/00 | (2006.01) | |
| C12N 15/86 | (2006.01) | |

(52) U.S. Cl.
CPC .......... *C07K 14/005* (2013.01); *A61K 9/0048* (2013.01); *A61K 48/0008* (2013.01); *A61K 48/0075* (2013.01); *C12N 7/00* (2013.01); *C12N 15/86* (2013.01); *C12N 2750/14121* (2013.01); *C12N 2750/14122* (2013.01); *C12N 2750/14133* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,436,146 A | 7/1995 | Shenk et al. | |
| 5,639,736 A | 6/1997 | Robinson | |
| 5,639,872 A | 6/1997 | Robinson | |
| 5,661,135 A | 8/1997 | Robinson | |
| 5,712,380 A | 1/1998 | Kendall et al. | |
| 5,753,500 A | 5/1998 | Shenk et al. | |
| 5,773,700 A | 6/1998 | Van Grinsven et al. | |
| 5,861,484 A | 1/1999 | Kendall et al. | |
| 6,040,183 A | 3/2000 | Ferrari et al. | |
| 6,054,297 A | 4/2000 | Carter et al. | |
| 6,093,570 A | 7/2000 | Ferrari et al. | |
| 6,096,548 A | 8/2000 | Stemmer | |
| 6,156,303 A | 12/2000 | Russell et al. | |
| 6,399,586 B1 | 6/2002 | Robinson | |
| 6,482,634 B1 | 11/2002 | Wilson et al. | |
| 6,491,907 B1 | 12/2002 | Rabinowitz et al. | |
| 6,548,286 B1 | 4/2003 | Samulski et al. | |
| 6,596,539 B1 | 7/2003 | Stemmer et al. | |
| 6,649,596 B1 | 11/2003 | Smyth et al. | |
| 6,703,237 B2 | 3/2004 | Samulski et al. | |
| 6,710,036 B2 | 3/2004 | Kurtzman et al. | |
| 6,733,757 B2 | 5/2004 | Patel et al. | |
| 6,855,314 B1 | 2/2005 | Chiorini et al. | |
| 6,943,153 B1 | 9/2005 | Manning, Jr. et al. | |
| 6,962,815 B2 | 11/2005 | Bartlett | |
| 7,060,269 B1 | 6/2006 | Baca et al. | |
| 7,071,159 B2 | 7/2006 | Kendall et al. | |
| 7,172,893 B2 | 2/2007 | Rabinowitz et al. | |
| 7,220,577 B2 | 5/2007 | Zolotukhin | |
| 7,252,997 B1 | 8/2007 | Hallek et al. | |
| 7,254,489 B2 | 8/2007 | Mossel | |
| 7,285,381 B1 | 10/2007 | Hallek et al. | |
| 7,314,912 B1 | 1/2008 | Hallek et al. | |
| 7,368,428 B2 | 5/2008 | Serrero | |
| 7,427,396 B2 | 9/2008 | Arbetman et al. | |
| 7,556,965 B2 | 7/2009 | Hallek et al. | |
| 7,585,676 B2 | 9/2009 | Mitrophanous et al. | |
| 7,629,322 B2 | 12/2009 | Kleinschmidt et al. | |
| 7,635,474 B2 | 12/2009 | Daly et al. | |
| 7,749,492 B2 | 7/2010 | Bartlett et al. | |
| 7,846,730 B2 | 12/2010 | Zhang et al. | |
| 7,858,367 B2 | 12/2010 | Amalfitano et al. | |
| 7,867,484 B2 | 1/2011 | Samulski et al. | |
| 7,919,473 B2 | 4/2011 | De Fougerolles et al. | |

(Continued)

FOREIGN PATENT DOCUMENTS

| | | |
|---|---|---|
| CA | 2379220 A1 | 1/2001 |
| CN | 1325451 A | 12/2001 |

(Continued)

OTHER PUBLICATIONS

Dalkara, D. et al., Science Trans. Med., 2013, vol. 5: pp. 1-11.*
U.S. Appl. No. 17/100,565, filed Nov. 20, 2020, Schaffer, et al..
U.S. Appl. No. 14/281,749, filed May 19, 2014, US 2015-0004101 A1, Jan. 1, 2015, U.S. Pat. No. 9,943,573, Apr. 17, 2018, Registered.
U.S. Appl. No. 14/660,657, filed Mar. 17, 2015, US 2015-0259395 A1, Sep. 17, 2015, U.S. Pat. No. 10,000,741, Jun. 19, 2018, Registered.
U.S. Appl. No. 15/388,380, filed Dec. 22, 2016, US 2017-0183647 A1, Jun. 29, 2017, U.S. Pat. No. 10,584,328, Mar. 10, 2020, Registered.
U.S. Appl. No. 15/554,664, filed Mar. 2, 2016, US 2018-0066022 A1, Mar. 8, 2018, Allowed.

(Continued)

*Primary Examiner* — Michael D Burkhart
(74) *Attorney, Agent, or Firm* — Cooley LLP

(57) ABSTRACT

The present disclosure provides adeno-associated virus (AAV) virions with altered capsid protein that binds heparan sulfate proteoglycans, where the AAV virions exhibit greater infectivity of retinal cells, altered tropism and/or the ability to bind and cross the inner limiting membrane following intravitreal injection. The present disclosure further provides methods of delivering a gene product to a retinal cell in an individual, and methods of treating ocular disease.

13 Claims, 25 Drawing Sheets

Specification includes a Sequence Listing.

(56) References Cited

U.S. PATENT DOCUMENTS

| | | |
|---|---|---|
| 7,947,659 B2 | 5/2011 | De Fougerolles et al. |
| 7,968,340 B2 | 6/2011 | Hallek et al. |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 8,802,080 B2 | 8/2014 | Warrington et al. |
| 8,889,641 B2 | 11/2014 | Asokan et al. |
| 8,900,858 B2 | 12/2014 | Trono et al. |
| 9,193,956 B2 | 11/2015 | Schaffer et al. |
| 9,233,131 B2 * | 1/2016 | Schaffer .................. C12N 7/00 |
| 9,409,953 B2 | 8/2016 | Asokan et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,587,282 B2 | 3/2017 | Schaffer et al. |
| 9,856,539 B2 | 1/2018 | Schaffer et al. |
| 9,943,573 B2 | 4/2018 | Constable et al. |
| 10,000,741 B2 | 6/2018 | Chalberg et al. |
| 10,004,788 B2 | 6/2018 | Constable et al. |
| 10,046,016 B2 | 8/2018 | Schaffer et al. |
| 10,202,657 B2 | 2/2019 | Schaffer et al. |
| 10,214,566 B2 | 2/2019 | Schaffer et al. |
| 10,214,785 B2 | 2/2019 | Schaffer et al. |
| 10,584,328 B2 | 3/2020 | Chavez et al. |
| 2002/0136710 A1 | 9/2002 | Samulski et al. |
| 2002/0155610 A1 | 10/2002 | Colosi |
| 2002/0168342 A1 | 11/2002 | Wang et al. |
| 2002/0192823 A1 | 12/2002 | Bartlett |
| 2003/0143732 A1 | 7/2003 | Fosnaugh et al. |
| 2003/0171254 A1 | 9/2003 | Sasaki et al. |
| 2004/0180440 A1 | 9/2004 | Zolotukhin |
| 2005/0053922 A1 | 3/2005 | Schaffer et al. |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0220766 A1 | 12/2005 | Bartlett et al. |
| 2005/0287122 A1 | 12/2005 | Bartlett et al. |
| 2006/0051333 A1 | 3/2006 | Arbetman et al. |
| 2006/0292117 A1 | 12/2006 | Loiler et al. |
| 2007/0020624 A1 | 1/2007 | Ruibenfield et al. |
| 2007/0036760 A1 | 2/2007 | Wilson et al. |
| 2007/0172460 A1 | 7/2007 | Kleinschmidt et al. |
| 2007/0196338 A1 | 8/2007 | Samulski et al. |
| 2007/0261127 A1 | 11/2007 | Boyden et al. |
| 2008/0188437 A1 | 8/2008 | Tolentino et al. |
| 2008/0269149 A1 | 10/2008 | Bowles et al. |
| 2009/0202490 A1 | 8/2009 | Schaffer et al. |
| 2009/0317417 A1 | 12/2009 | Vandenberghe et al. |
| 2010/0015095 A1 | 1/2010 | Pan et al. |
| 2010/0166729 A9 | 7/2010 | Madison et al. |
| 2010/0172871 A1 | 7/2010 | Flannery et al. |
| 2011/0104120 A1 | 5/2011 | Xiao et al. |
| 2011/0143400 A1 | 6/2011 | Reich et al. |
| 2011/0171262 A1 | 7/2011 | Bakker et al. |
| 2011/0236353 A1 | 9/2011 | Wilson et al. |
| 2011/0301073 A1 | 12/2011 | Gregory et al. |
| 2012/0093772 A1 | 4/2012 | Horsager et al. |
| 2012/0100136 A1 | 4/2012 | Patel et al. |
| 2013/0323302 A1 | 12/2013 | Constable et al. |
| 2014/0242031 A1 | 8/2014 | Schaffer et al. |
| 2014/0294771 A1 | 10/2014 | Schaffer et al. |
| 2014/0336245 A1 | 11/2014 | Mingozzi et al. |
| 2014/0341852 A1 | 11/2014 | Srivastava et al. |
| 2014/0364338 A1 | 12/2014 | Schaffer et al. |
| 2015/0005369 A1 | 1/2015 | Muzyczka et al. |
| 2015/0118201 A1 | 4/2015 | Xiao et al. |
| 2015/0132262 A1 | 5/2015 | Schaffer et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0315610 A1 | 11/2015 | Nishie et al. |
| 2016/0017295 A1 | 1/2016 | Schaffer et al. |
| 2016/0040137 A1 | 2/2016 | Lock et al. |
| 2016/0102324 A1 | 4/2016 | Duchateau et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |
| 2017/0044504 A1 | 2/2017 | Schaffer et al. |
| 2017/0096683 A1 | 4/2017 | Scaria et al. |
| 2018/0066022 A1 | 3/2018 | Chalberg et al. |
| 2018/0289757 A1 | 10/2018 | Schaffer et al. |
| 2018/0311319 A1 | 11/2018 | Constable et al. |
| 2018/0320145 A1 | 11/2018 | Chalberg et al. |
| 2018/0344197 A1 | 12/2018 | Neitz et al. |
| 2019/0142975 A1 | 5/2019 | Keravala et al. |
| 2019/0169237 A1 | 6/2019 | Schaffer et al. |
| 2019/0218627 A1 | 7/2019 | Schaffer et al. |
| 2019/0255192 A1 | 8/2019 | Kirn et al. |
| 2020/0010851 A1 | 1/2020 | Keravala |
| 2020/0149033 A1 | 5/2020 | Chavez et al. |
| 2021/0040501 A1 | 2/2021 | Keravala |
| 2021/0077552 A1 | 3/2021 | Schaffer et al. |

FOREIGN PATENT DOCUMENTS

| | | |
|---|---|---|
| CN | 1826414 A | 8/2006 |
| CN | 1966082 A | 5/2007 |
| CN | 101484005 A | 7/2009 |
| CN | 101532024 A | 9/2009 |
| CN | 103561774 A | 2/2014 |
| GB | 2545763 A | 6/2017 |
| JP | 2008-523813 A | 7/2008 |
| JP | 2014-518614 | 8/2014 |
| WO | WO 1997/038723 A1 | 10/1997 |
| WO | WO 1998/011244 A2 | 3/1998 |
| WO | WO 1999/061601 A2 | 12/1999 |
| WO | WO 1999/067393 A2 | 12/1999 |
| WO | WO 2000/028004 A1 | 5/2000 |
| WO | WO 2000/028061 A2 | 5/2000 |
| WO | WO 2001/070276 A2 | 9/2001 |
| WO | WO 2002/053703 A2 | 7/2002 |
| WO | WO 2003/018820 A2 | 3/2003 |
| WO | WO 2003/023032 A2 | 3/2003 |
| WO | WO 2003/054197 A2 | 7/2003 |
| WO | WO 2003/093436 A2 | 11/2003 |
| WO | WO 2004/027019 A2 | 4/2004 |
| WO | WO 2004/108922 A2 | 12/2004 |
| WO | WO 2004/112727 A2 | 12/2004 |
| WO | WO 2005/005610 A2 | 1/2005 |
| WO | WO 2005/033321 A2 | 4/2005 |
| WO | WO 2006/066066 A2 | 6/2006 |
| WO | WO 2006/110689 A2 | 10/2006 |
| WO | WO 2007/120542 A2 | 10/2007 |
| WO | WO 2008/131951 A1 | 11/2008 |
| WO | WO 2009/137006 A2 | 11/2009 |
| WO | WO 2009/154452 A2 | 12/2009 |
| WO | WO 2010/093784 A2 | 8/2010 |
| WO | WO 2010/138263 A2 | 12/2010 |
| WO | WO 2011/117258 A2 | 9/2011 |
| WO | WO 2012/145601 A2 | 10/2012 |
| WO | WO 2013/029030 A1 | 2/2013 |
| WO | WO 2013/170078 A1 | 11/2013 |
| WO | WO 2013/173129 A2 | 11/2013 |
| WO | WO 2013/173512 A2 | 11/2013 |
| WO | WO 2014/194132 A1 | 12/2014 |
| WO | WO 2015/048534 A1 | 4/2015 |
| WO | WO 2015/054653 A2 | 4/2015 |
| WO | WO 2015/121501 A1 | 8/2015 |
| WO | WO 2015/134643 A1 | 9/2015 |
| WO | WO 2015/142941 A1 | 9/2015 |
| WO | WO 2015/168666 A2 | 11/2015 |
| WO | WO 2015/191693 A2 | 12/2015 |
| WO | WO 2016/133917 A1 | 8/2016 |
| WO | WO 2016/141078 A1 | 9/2016 |
| WO | WO 2016/144892 A1 | 9/2016 |
| WO | WO 2017/023724 A1 | 2/2017 |
| WO | WO 2017/112868 A1 | 6/2017 |
| WO | WO 2017/190125 A1 | 11/2017 |
| WO | WO 2017/197355 A2 | 11/2017 |
| WO | WO 2018/075798 A1 | 4/2018 |

(56) References Cited

FOREIGN PATENT DOCUMENTS

WO   WO 2018/160686 A1   9/2018
WO   WO 2018/170473 A1   9/2018

OTHER PUBLICATIONS

U.S. Appl. No. 15/851,650, filed Dec. 21, 2017, US 2018-0125948 A1, May 10, 2018, U.S. Pat. No. 10,004,788, Jun. 26, 2018, Registered.
U.S. Appl. No. 15/939,674, filed Mar. 29, 2018, US 2018-0344197 A1, Dec. 6, 2018, Pending.
U.S. Appl. No. 15/961,654, filed Apr. 24, 2018, US 2018-0311319 A1, Nov. 1, 2018, Pending.
U.S. Appl. No. 15/984,085, filed May 18, 2018, US 2018-0320145 A1, Nov. 8, 3018, Pending.
U.S. Appl. No. 16/097,377, filed May 1, 2017, US 2019-0142975 A1, May 16, 2019, Pending.
U.S. Appl. No. 16/098,354, filed May 2, 2017, US 2019-0154667 A1, May 23, 2019, Pending.
U.S. Appl. No. 16/488,689, filed Feb. 28, 2018, Pending.
U.S. Appl. No. 16/494,203, filed Mar. 16, 2018, US 2020-0010851 A1, Jan. 9, 2020, Pending.
U.S. Appl. No. 16/750,736, filed Jan. 23, 2020, US 2020-0149033 A1, May 14, 2020, Pending.
U.S. Appl. No. 16/998,540, filed Aug. 20, 2020, US 2021-0040501 A1, Feb. 11, 2021, Pending.
U.S. Appl. No. 13/889,275, filed May 7, 2013, US 2013-0323302 A1, Dec. 5, 2013, Abandoned.
U.S. Appl. No. 14/281,765, filed May 19, 2014, US 2014-0341977 A1, Nov. 20, 2014, Abandoned.
U.S. Appl. No. 14/281,783, filed May 19, 2014, Abandoned.
U.S. Appl. No. 14/407,054, filed Jun. 10, 2013, US 2015-0111275 A1, Apr. 23, 2015, Abandoned.
U.S. Appl. No. 15/554,664, filed Mar. 2, 2016, US 2018-0066022 A1, Mar. 8, 2018, Pending.
U.S. Appl. No. 16/988,540, filed Aug. 20, 2020, Pending.
U.S. Appl. No. 15/984,085, filed May 18, 2018, US 2018-0320145 A1, Nov. 8, 2018, Pending.
U.S. Appl. No. 16/488,689, filed Aug. 26, 2019, Keravala.
Adachi, et al., "A New Recombinant Adeno-Associated Virus (AAV)-Based Random Peptide Display Library System: Infection-Defective AAV 1 .9-3 As A Novel Targeted Platform for Vector Evolution"; Gene Therapy and Regulation; vol. 5, No. 1, pp. 31-55 (Oct. 2010).
Akiyama, et al., "Intraocular Injection of an Aptamer that Binds PDGF-B: A Potential Treatment for Proliferative Retinopathies," Journal of Cellular Physiology, vol. 207, pp. 407-412 (2006).
Ali, et al., "Restoration of photoreceptor ultrastructure and function in retinal degeneration slow mice by gene therapy." Nature Genetics; vol. 25, pp. 306-310 (Jul. 2000).
Allocca, et al., "Novel adeno-associated virus serotypes efficiently transduce murine photoreceptors", Journal of Virology (Oct. 2007), 81(20): 11372-11380.
Asokan, et al., "Reengineering a receptor footprint of adeno-associated virus enables selective and systemic gene transfer to muscle", Nat Biotechnol, (Jan. 2010); 28(1): 79-82.
Asuri, et al., "Directed evolution of adeno-associated virus for enhanced gene delivery and gene targeting in human pluripotent stem cells." Mol Ther. (Feb. 2012); 20(2): 329-338. Epub Nov. 22, 2011.
Bantel-Schaal et al. "Human Adeno-Associated Virus Type 5 Is Only Distantly Related to Other Known Primate Helper-Dependent Parvoviruses." Journal of Virology (1999); 73:2, p. 939-947.
Berge, et al., "Pharmaceutical salts." J Pharm Sci. 1977; 66(1): 1-19.
Bichsel, et al., "Bacterial delivery of nuclear proteins into pluripotent and differentiated cells", PLoS One (Jan. 2011); 6(1): e16465, pp. 1-9.
Blacklow, et al., "A Seroepidemiologic Study of Adenovirus-Associated Virus Infection in Infants and Children." Am J Epidemiol.; vol. 94, No. 4, pp. 359-366 (Oct. 1971).
Booij, et al., "Simultaneous Mutation Detection in 90 Retinal Disease Genes in Multiple Patients Using a Custom-designed 300-kb Retinal Resequencing Chip". Ophthalmology (Jan. 2011); 118(1): 160-167, e1-3.
Boucas, et al., "Engineering adeno-associated virus serotype 2-based targeting vectors using a new insertion site-position 453-and single point mutations." J Gene Med., Dec. 2009, 11(12):1103-1113.
Boye, et al., "Impact of Heparan Sulfate Binding on Transduction of Retina by Recombinant Adeno-Associated Virus Vectors". J Virol. (Mar. 28, 2016); 90(8): 4215-4231. Print Apr. 2016.
Buch, et al., "In Contrast to AAC-Mediated Cntf Expression. AAV-Mediated Gdnf Expression Enhances Gene Replacement Therapy in Rodent Models of Retinal Degeneration"; Molecular Therapy; vol. 14, No. 5, pp. 700-709 (Nov. 2006).
Büning, Hildegard, et al. "Recent developments in adeno-associated virus vector technology." The Journal of Gene Medicine (2008); 10.7: 717-733.
Byrne, et al., "Retinoschisin gene therapy in photoreceptors, Müller glia or all retinal cells in the Rs1h-/-mouse." Gene Ther. (Jun. 2014); 21(6): 585-592. Epub Apr. 3, 2014.
Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).
Chen, Haifen, "Adeno-associated virus vectors for human gene therapy". World J Med Genet. (Aug. 27, 2015); 5(3): 28-45. Epub Aug. 2, 20157.
Chiorini et al. "Cloning and Characterization of Adeno-Associated Virus Type 5." Journal of Virology (1999); 73:2, p. 1309-1319.
Chiorini et al. "Cloning of Adeno-Associated Virus Type 4 (AAV4) and Generation of Recombinant AAV4 Particles." Journal of Virology (1997); 71:9, p. 6823-6833.
Choi, et al.; "AAV Hybrid Serotypes: Improved Vectors for Gene Delivery."; Current Gene Therapy; vol. 5, No. 3, pp. 299-310 (Jun. 2005).
Clinical Trial NCT01494805, History of Changes for "Safety and Efficacy Study of rAAV.sFlt-1 in Patients With Exudative Age-Related Macular Degeneration (AMD)", NCT01494805, Submitted Date: Dec. 15, 2011 (v1), ClinicalTrials.gov, https://clinicaltrials.gov/ct2/history/NCT01494805?V_1=View#StudyPageTop, 9 pages.
Cronin, et al., "Efficient transduction and optogenetic stimulation of retinal bipolar cells by a synthetic adeno-associated virus capsid and promoter". EMBO Mol Med. (Sep. 2014); 6(9): 1175-1190.
Dalkara, et al., "Developing Photoreceptor Targeted AAV Variant by Directed Evolution." ARVO Annual Meeting Abstract Search and Program Planner; vol. 2011, p. 4381 (May 2011).
DATABASE Geneseq [Online] Oct. 16, 2008 (Oct. 16, 2008), "Modified Adeno-associated virus (hu.44) capsid protein, VP1, hu.44R2.", retrieved from EBI accession No. GSP:AEL63853, Database accession No. AEL63853, 1 page.
DATABASE Geneseq [Online] Oct. 16, 2008 (Oct. 16, 2008), "Modified Adeno-associated virus (hu.44) capsid protein, VP1, hu.44R3.", retrieved from EBI accession No. GSP:AEL63854, Database accession No. AEL63854.
Davidson, et al., "Recombinant adeno-associated virus type 2, 4, and 5 vectors: transduction of variant types and regions in the mammalian central nervous system."; Proc Natl Acad Sci USA; vol. 97, No. 7, pp. 3428-3432 (Mar. 28, 2000).
Day, et al., "Advances in AAV vector development for gene therapy in the retina." Adv Exp Med Biol. (2014); 801:687-693.
Den Dunnen, et al., "Mutation nomenclature extensions and suggestions to describe complex mutations: a discussion."; Human Mutation; vol. 15, pp. 7-12 (2000).
Den Hollander, et al., "Mutations in a human homologue of *Drosophila* crumbs cause retinitis pigmentosa (RP12)". Nature Genetics (Oct. 1999); 23(2): 217-221.
Diprimo, et al., "Surface loop dynamics in adeno-associated virus capsid assembly", Journal of Virology (2008); vol. 82, No. 11, pp. 5178-5189.

(56) References Cited

OTHER PUBLICATIONS

Do, et al., "An exploratory study of the safety, tolerability and bioactivity of a single intravitreal injection of vascular endothelial growth factor Trap-Eye in patients with diabetic macular oedema". Br J Ophthalmol. (Feb. 2009); 93(2): 144-149.
Donnelly, et al. "Missense mutation in the choroideremia gene." Human Molecular Genetics (Jun. 1994); 3(6): 1017, 1 page.
Erles et al.; "Update on the prevalence of serum antibodies (IgG and IgM) to adeno-associated virus (AAV)." J Med Virol.; vol. 59, No. 3, pp. 406-411 (Nov. 1999).
European Patent Application No. 17863237.8, Extended Supplementary European Search Report dated Nov. 4, 2020, 21 pages.
European Patent Application No. 17863237.8, Partial Supplementary European Search Report dated Jun. 8, 2020, 18 pages.
European Patent Application No. 18760397.2, Extended European Search Report dated Jul. 23, 2020, 11 pages.
Excoffon, et al., "Directed evolution of adeno-associated virus to an infectious respiratory virus." Proc Natl Acad Sci USA. (Mar. 2009); 106(10): 3865-3870.
Flotte, et al.; "Gene expression from adeno-associated virus vectors in airway epithelial cells." Am J Respir Cell Mol Biol.; vol. 7, No. 3, pp. 349-356 (Sep. 1992).
Gao et al. "Novel adeno-associated viruses from rhesus monkeys as vectors for human gene therapy". PNAS (2002); 99:18, p. 11854-11859.
GenBank accession No. ABZ10812; AAV13 capsid protein sequence downloaded from NBCI; downloaded on Nov. 3, 2008.
GenBank Accession No. CAM23328 "crumbs homolog 1 (*Drosophila*) [*Homo sapiens*]" Jan. 13, 2009 [online], (Retrieved online Feb. 21, 2019].
GenBank Accession No. NP_000313 "peripherin-2 [*Homo sapiens*]," Dec. 23, 2018 [online], (Retrieved online Feb. 21, 2019].
GenBank Accession No. NP_001289 "cyclic nucleotide-gated cation channel alpha-3 isoform 1 [*Homo sapiens*]," Feb. 17, 2019 [online], (Retrieved online Feb. 21, 2019].
GenBank Accession No. Q96KN7 "RecName: Full=X-linked retinitis pigmentosa GTPase regulator-interacting protein 1; Short=RPGR-interacting protein 1," Feb. 13, 2019 [online], (Retrieved online Feb. 21, 2019].
GenBank Accession No. Q9EPQ2 "RecName: Full=X-linked retinitis pigmentosa GTPase regulator-interacting protein 1; Short=RPGR-interacting protein 1" Jan. 16, 2019 [online], (Retrieved online Feb. 21, 2019].
GenBank Accession No. Q9GLM3 "RecName: Full=X-linked retinitis pigmentosa GTPase regulator-interacting protein 1; Short=RPGR-interacting protein 1" Jan. 16, 2019 [online], (Retrieved online Feb. 21, 2019].
GenBank Accession No. AAZ79678; rat AAV1 VP3 capsid protein sequence downloaded from NCBI; downloaded on Nov. 3, 2008.
Girod, et al., "Genetic capsid modifications allow efficient re-targeting of adeno-associated virus type 2." Nat. Med. (1999); vol. 5, No. 9, pp. 1052-1056.
Grainger, et al., "869. Infectious Titer Assay for Recombinant Adeno-Associated Virus Vectors Using Direct Cell Lysis and End-point Taqman PCR". Molecular Therapy (May 2005); 11 (Suppl 1): S337, 1 page.
Gray, et al., "Directed Evolution of a Novel Adeno-associated Virus (AAV) Vector That Crosses the Seizure-compromised Blood-Brain Barrier (BBB)." Molecular Therapy; vol. 18, No. 3, pp. 570-578 (2010).
Gregory-Evans, et al., "Ex vivo Gene Therapy Using Intravitreal Injection of GDNF-secreting Mouse Embryonic Stem Cells in a Rat Model of Retinal Degeneration." Molecular Vision; vol. 15, pp. 962-973 (May 13, 2009).
Grieger, et al., "Separate Basic Region Motifs within the Adeno-Associated Virus Capsid Proteins Are Essential for Infectivity and Assembly." J. Viral. (2006), 80(11): 5199-5210.
Grifman, et al., "Incorporation of tumor-targeting peptides into recombinant adeno-associated virus capsids". Molecular Therapy (2001); vol. 3, No. 6, pp. 964-975.

Grimm, et al., "In Vitro and In Vivo Gene Therapy Vector Evolution via Multispecies Interbreeding and Retargeting of Adeno-Associated Viruses." Journal of Virology; vol. 82, No. 12, pp. 5887-5911 (Jun. 2008).
Halbert, et al., "Repeat transduction in the mouse lung by using adeno-associated virus vectors with different serotypes." J. Virol.; vol. 74, No. 3, pp. 1524-1532 (Feb. 2000).
Hellström, et al., "Cellular tropism and transduction properties of seven adeno-associated viral vector serotypes in adult retina after intravitreal injection." Gene Therapy (2009); 16: 521-532.
Hirsch, et al., "Directed Evolution of the AAV Capsid for Human Embryonic Stem Cell Transduction." Molecular Therapy; vol. 17, Supp. 1, S177-S178 (May 2009).
Huttner, et al., "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002), 2 pgs.
Huttner, et al., "Genetic modifications of the adeno-associated virus type 2 capsid reduce the affinity and the neutralizing effects of human serum antibodies." Gene Ther; vol. 10, No. 26, pp. 2139-2147 (Dec. 2003).
International Preliminary Reporton Patentability for International Application No. PCT/US2018/020215, dated Sep. 3, 2019, 9 pages.
International Preliminary Reporton Patentability for International Application No. PCT/US2017/057441, dated Apr. 23, 2019, 9 pages.
International Search Report and Written Opinion for International Application No. PCT/US2018/020215, dated Jun. 26, 2018, 14 pages.
International Search Report and Written Opinion for International Application No. PCT/US2017/057441, dated Feb. 13, 2018, 12 pages.
Invitation to Pay Additional Fees for International Application No. PCT/US2018/020215, dated May 3, 2018, 3 pages.
Jang, et al., "An evolved adeno-associated viral variant enhances gene delivery and gene targeting in neural stem cells." Mol Ther. (Apr. 2011); 19(4): 667-675.
Kaiser, et al., "RNAi-Based Treatment for Neovascular Age-Related Macular Degeneration by Sirna-027." American Journal of Ophthalmology (Jul. 2010); 150(1): 33-39.
Karp, et al., "An in vitro model of differentiated human airway epithelia. Methods for establishing primary cultures." Methods Mol Biol.; vol. 188, pp. 115-137 (2002).
Katterhorn, et al., "Adeno-Associated Virus Gene Therapy for Liver Disease". Hum Gene Ther. (Dec. 2016); 27(12): 947-961.
Kendall, et al., "Inhibition of vascular endothelial cell growth factor activity by an endogenously encoded soluble receptor." Proc Natl Acad Sci USA. (1993); 90(22): 10705-10709.
Keravala, et al., "316. Evaluating AAV Hybrid Variants for Improved Tropism after Intravitreal Gene Delivery to the Retina". Molecular Therapy (May 1, 2015); 23(1): S127-S128.
Kern, et al., "Identification of a heparin-binding motif on adeno-associated virus type 2 capsids." Journal of Virology; vol. 77, No. 20, p. 11072-11081 (Oct. 2003).
Khaboo, et al., "Insight into the mechanisms of enhanced retinal transduction by the engineered AAV2 capsid variant-7m8". Biotechnol Bioeng. (Dec. 2016); 113(12): 2712-2724. Epub Jun. 30, 2016.
Khani, et al., "AAV-mediated expression targeting of rod and cone photoreceptors with a human rhodopsin kinase promoter." Investigative Ophthalmology & Visual Science. 2007; 48(9): 3954-3961.
Klimczak, et al., "A novel adeno-associated viral variant for efficient and selective intravitreal transduction of rat muller cells." PLoS One (Oct. 2009); 4(10): e7467.
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 117 pages (2010).
Koerber, et al., "DNA Shuffling of Adeno-associated Virus Yields Functionally Diverse Viral Progeny." Mol Ther. (Oct. 2008); 16(10): 1703-1709. Epub Aug. 6, 2008.

(56) References Cited

OTHER PUBLICATIONS

Koerber, et al., "Engineering of a Novel AAV Vector In a Human Airway Model System for Cystic Fibrosis Gene Therapy"; AIChE Annual Meeting Abstract, 3 pages (Nov. 29, 2008).
Koerber, et al., "Molecular evolution of adeno-associated virus for enhanced glial gene delivery." Molecular Therapy (2009); vol. 17, No. 12, pp. 2088-2095.
Kohl, et al., "CNGB3 mutations account for 50% of all cases with autosomal recessive achromatopsia". European Journal of Human Genetics (Mar. 2005); 13(3): 302-308.
Kotterman and Schaffer, "Engineering adeno-associated viruses for clinical gene therapy." Nat Rev Genet. (Jul. 2014); 15(7): 445-451. Epub May 20, 2014.
Kou, et al. "Differential Regulation of Vascular Endothelial Growth Factor Receptors (VEGFR) Revealed by RNA Interference: Interactions of VEGFR-1 and VEGFR-2 in Endothelial Cell Signaling." Biochemistry (Nov. 1, 20055); 44(45): 15064-15073.
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al., "Long-term evaluation of AAV-mediated sFlt-1 gene therapy for ocular neovascularization in mice and monkeys." Mol Ther. (Oct. 2005); 12(4): 659-668.
Lee, et al. "A therapeutic aptamer inhibits angiogenesis by specifically targeting the heparin binding domain of VEFG." PNAS (Dec. 27, 2005); 102(52): 18902-18907.
Li, et al., "In vivo genome editing restores haemostasis in a mouse model of haemophilia". Nature (Jun. 26, 2011); 475(7355): 217-221.
Li, et al., "Engineering and Selection of Shuffled AAV Genomes: A New Strategy for Producing Targeted Biological Nanoparticles." Molecular Therapy; vol. 15, No. 7, pp. 1252-1260 (Jul. 2008).
Li, et al., "Generation of novel AAV variants by directed evolution for improved CFTR delivery to human ciliated airway epithelium." Molecular Therapy (2009), vol. 17, No. 12, pp. 2067-2077.
Limberis, et al., "Adeno-associated virus serotype 9 vectors transduce murine alveolar and nasal epithelia and can be readministered." (and Correction) Proc Natl Acad Sci USA; vol. 103, No. 35, p. 12993-12998 (Aug. 29, 2006).
Loiler, et al., "Targeting recombinant adeno-associated virus vectors to enhance gene transfer to pancreatic islets and liver." Gene Ther.; vol. 10, pp. 1551-1558 (2003).
Maguire, et al., "Directed evolution of adeno-associated virus for glioma cell transduction." J. Neurooncol.; vol. 96, pp. 337-347 (2010).
Maheshri, Narendra, et al. "Directed evolution of adeno-associated virus yields enhanced gene delivery vectors." Nature Biotechnology (2006); 24.2:198-204.
Mancuso, Katherine, et al. "Gene therapy for red-green colour blindness in adult primates." Nature (2009); 461.7265: 784-787.
McCullum, et al., "Random Mutagenesis by Error-Prone PCR." Jeff Braman (ed.), In Vitro Mutagenesis Protocols: Third Edition, Methods in Molecular Biology (2010); vol. 634, pp. 103-109.
McGee Sanftner, et al., "Glial Cell Line Derived Neurotrophic Factor Delays Photoreceptor in a Transgenic Rat Model of Retinitis Pigmentosa." Molecular Therapy; vol. 4, No. 6, pp. 622-629 (Dec. 2001).
Michelfelder, et al., "Successful Expansion but Not Complete Restriction of Tropism of Adeno-Associated Virus by In Vivo Biopanning of Random Virus Display Peptide Libraries." PLoS One; vol. 4, No. 4, pp. 1-13 (Apr. 2009).
Michelfelder, et al., "Vectors selected from adeno-associated viral display peptide libraries for leukemia cell-targeted cytotoxic gene therapy." Experimental Hematology; vol. 35, pp. 1766-1776 (2007).
Mitchell, et al., "AAV's anatomy: Roadmap for optimizing vectors for translational success." Curr Gene Ther. (2010); vol. 10, No. 5, pp. 319-340.

Mori, et al., "Two novel adeno-associated viruses from cynomolgus monkey: pseudotyping characterization of capsid protein." Virology (2004); 330: 375-383.
Morimura, et al., "Mutations in the RPE65 gene in patients with autosomal recessive retinitis pigmentosa or Leber congenital amaurosis". PNAS (Mar. 17, 1998); 95(6): 3088-3093.
Moskalenko, et al., "Epitope mapping of human anti-adeno-associated virus type 2 neutralizing antibodies: Implications for gene therapy and virus structure." J. Virol.; vol. 74, No. 4, pp. 1761-1766 (Feb. 2000).
Müller, et al., "Random peptide libraries displayed on adeno-associated virus to select for targeted gene therapy vectors." Nature Biotechnology (2003); 21.9:1040-1046.
Muramatsu et al. "Nucleotide Sequencing and Generation of an Infectious Clone of Adeno-Associated Virus 3." Virology (1996); 221:0367, p. 208-217.
Neal, et al., "P249 Evaluating the degree of HSPG-binding for effective AAV transduction following intravitreal administration". Human Gene Therapy (Nov. 1, 2016); 27(11): A121, 1 page.
Ng, et al. "Pegaptanib, a targeted anti-VEGF aptamer for ocular vascular disease." Nature Reviews Drug Discovery (Feb. 2006); 5(2): 123-132.
Nguyen, et al., "Convection-enhanced delivery of AAV-2 combined with heparin increases TK gene transfer in the rat brain." Neuroreport; vol. 12, No. 9, pp. 1961-1964 (Jul. 3, 2001).
Ni and Hui. "Emerging Pharmacologic Therapies for Wet Age-Related Macular Degeneration." Ophthalmologica (2009); 223(6): 401-410.
Nicklin, et al., "Efficient and selective AAV2-mediated gene transfer directed to human vascular endothelial cells." Molecular Therapy (2001); vol. 4, No. 2, pp. 174-181.
Nicoud et al. "Development of photoreceptor-specific promoters and their utility to investigate EIAV lentiviral vector mediated gene transfer to photoreceptors." The Journal of Gene Medicine (2007); 9(12): 1015-1023.
Opie, et al., "Identification of Amino Acid Residues in the Capsid Proteins of Adeno-Associated Virus Type 2 that Contribute to Heparan Sulfate Proteoglycan Binding." Journal of Virology; vol. 77, No. 12, pp. 6995-7006 (Jun. 2003).
Ortolano, et al., "Present and future of adeno associated virus based gene therapy approaches". Recent Pat Endocr Metab Immune Drug Discov. (Jan. 2012); 6(1): 47-66.
Paddison, et al., "Stable suppression of gene expression by RNAi in mammalian cells." Proc. Nat'l Acad. Sci. USA; vol. 99, No. 3, pp. 1443-1448 (Feb. 5, 2002).
Padron, et al., "Structure of adeno-associated virus type 4." Journal of Virology (2005); 79(8): 5047-5058.
Park, et al., "Intravitreal delivery of AAV8 retinoschisin results in cell type-specific gene expression and retinal rescue in the Rs1-KO mouse." Gene Therapy (2009); 16(7): 916-926.
Pechan, et al., "Novel anti-VEGF chimeric molecules delivered by AAV vectors for inhibition of retinal neovascularization", Gene Ther. (2009); 16(1): 10-16.
Perabo, et al., "In Vitro Selection of Viral Vectors with Modified Tropism: The Adeno-associated Virus Display." Molecular Therapy; vol. 8, No. 1, pp. 151-157 (Jul. 2003).
Perabo, et al., "Combinatorial engineering of a gene therapy vector: directed evolution of adeno-associated virus." The Journal of Gene Medicine (2006); vol. 8, pp. 155-162.
Perabo, et al., "Heparan Sulfate Proteoglycan Binding Properties of Adeno-Associated Virus Retargeting Mutants and Consequences for Their In Vitro Tropism." Journal of Virology; vol. 80, No. 14, pp. 7265-7269 (Jul. 2006).
Petrs-Silva, et al., "High-efficiency transduction of the mouse retina by tyrosine-mutant AAV serotype vectors." Molecular Therapy (2009); 17(3): 463-471.
Popa-Wagner, et al., "Impact of VP1-Specific Protein Sequence Motifs on Adeno-Associated Virus Type 2 Intracellular Trafficking and Nuclear Entry". Journal of Virology (Sep. 2012); 86(17): 9163-9174. Epub Jun. 13, 2012.
Rabinowitz, et al., "Building a Better Vector: The Manipulation of AAV Virions." Virology; vol. 278, pp. 301-308 (2000).

(56) References Cited

OTHER PUBLICATIONS

Rabinowitz, et al., "Insertional mutagenesis of AAV2 capsid and the production of recombinant virus." Virology; vol. 265, No. 2, pp. 274-285 (Dec. 20, 1999).
Raupp, et al., "The threefold protrusions of adeno-associated virus type 8 are involved in cell surface targeting as well as postattachment processing". Journal of Virology (Sep. 2012); 86(17): 9396-9408. Epub Jun. 20, 2012.
Rayaprolu, et al., "Comparative analysis of adeno-associated virus capsid stability and dynamics". Journal of Virology (Dec. 2013); 87(24): 13150-13160. Epub Sep. 25, 2013.
Reich, et al. "Small interfering RNA (siRNA) targeting VEGF effectively inhibits ocular neovascularization in mouse model." Molecular Vision (May 30, 2003); 9: 201-216.
Ried, et al., "Adeno-associated virus capsids displaying immunoglobulin-binding domains permit antibody-mediated vector retargeting to specific cell surface receptors." J. Virol.; vol. 76, No. 9, pp. 4559-4566 (May 2002).
Ryals, et al., "Quantifying transduction efficiencies of unmodified and tyrosine capsid mutant AAV vectors in vitro using two ocular cell lines." Mol Vision (Apr. 2011); 7:1090-1102.
Santiago-Ortiz, et al., "AAV ancestral reconstruction library enables selection of broadly infectious viral variants". Gene Ther. (Dec. 2015); 22(12): 934-946. Epub Jul. 17, 2015.
Schaffer, et al.; "Directed evolution of AAV vector mutants for enhanced gene delivery"; Abstracts of Papers American Chemical Society; vol. 227, Part 1, Abstract 172, p. U214 (Mar. 28-Apr. 1, 2004), 2 pages.
Score Search Result 33 for Arbetman et al. WO2004112727-A2, Dec. 29, 2004, 3 pages.
Score Search Results / Report for Per SEQ ID No. 17 per US2002/0192823 (U.S. Appl. No. 10/038,972) to Bartlett Published Dec. 19, 2002, 2 pages.
Shade et al. "Nucleotide Sequence and Genome Organization of Human Parvovirus B19 Isolated from the Serum of a Child during Aplastic Crisis." Journal of Virology (1986); 58:3, p. 921-936.
Shen et al. "Suppression of ocular neovascularization with siRNA targeting VEGF receptor 1." Gene Therapy (Feb. 2006); 13(3): 225-234.
Shen, et al., "Multiple roles for sialylated glycans in determining the cardiopulmonary tropism of adeno-associated virus 4." J Virol. (Dec. 2013); 87(24): 13206-13213. Epub Sep. 25, 2013.
Shen, et al., "Characterization of the relationship of AAV capsid domain swapping to liver transduction efficiency." Mol Ther. (2007); 15(11): 1955-1962.
Shi, et al., "Insertional mutagenesis at positions 520 and 584 of adeno-associated virus type 2 (AAV2) capsid gene and generation of AAV2 vectors with eliminated heparin-binding ability and introduced novel tropism." Hum. Gene Ther.; vol. 17, pp. 353-361 (Mar. 2006).
Shi, et al., "Capsid modifications overcome low heterogeneous expression of heparan sulfate proteoglycan that limits AAV2-mediated gene transfer and therapeutic efficacy in human ovarian carinoma." Gynecol. Oncol.; vol. 103, pp. 1054-1062 (2006).
Shi, et al., "Insertional mutagenesis of the adeno-associated virus type 2 (AAV2) capsid gene and generation of AAV2 vectors targeted to alternative cell-surface receptors", Hum Gene Ther (2001); vol. 12, No. 14, pp. 1697-1711.
Shi, et al., "RGD inclusion in VP3 provides adeno-associated virus type 2 (AAV2)-based vectors with a heparan sulfate-independent cell entry mechanism." Mol. Ther.; vol. No. 4, pp. 515-525 (Apr. 2003).
Sonntag, et al., "Adeno-associated virus type 2 capsids with externalized VP1/VP2 trafficking domains are generated prior to passage through the cytoplasm and are maintained until uncoating occurs in the nucleus." Journal of Virology; vol. 80, No. 22, p. 11040-11054 (Nov. 2006).
Srivastava et al. "Nucleotide Sequence and Organization of the Adeno Associated Virus 2 Genome." Journal of Virology (1983); 45:2, p. 555-564.
Steinbach, et al., "Assembly of adeno-associated virus type 2 capsids in vitro." J of Gen Virology; vol. 78, pp. 1453-1462 (1997).
Sullivan, et al., "Rationally designed AAV2 and AAVrh8R capsids provide improved transduction in the retina and brain." Gene Ther. (Jun. 2018); 25(3): 205-219. Epub May 22, 2018.
Sun, et al., "Immune response to adeno-associated virus and its recombinant vectors." Gene Therapy; vol. 10, pp. 964-976 (2003).
Surace, et al., "Delivery of Adeno-Associated Virus Vectors to the Fetal Retina: Impact of Viral Capsid Proteins on Retinal Neuronal Progenitor Transduction." Journal of Virology; vol. 77, No. 14, pp. 7957-7963 (Jul. 2003).
Takada, et al., "Synaptic Pathology in Retinoschisis Knockout (Rs1-/y) Mouse Retina and Modification by 4 rAAV-Rs1 Gene Delivery." Investigative Ophthalmology & Visual Science; vol. 49, No. 8, pp. 3677-3678 (Aug. 2008).
Tal, "Adeno-Associated Virus-Based Vectors in Gene Therapy." Journal of Biomedical Science; vol. 7, No. 4, pp. 279-291 (Jul. 2000).
Tomar, et al., "Use of Adeno-Associated Viral Vector for Delivery of Small Interfering RNA." Oncogene; vol. 22, No. 36, pp. 5712-5715 (Aug. 28, 2003).
Van Bokhoven, et al., "Cloning and characterization of the human choroideremia gene". Hum Mol. Genet. (Jul. 1994); 3(7): 1041-1046.
Van Vliet, et al., "Proteolytic mapping of the adeno-associated virus capsid." Mol Ther. (Dec. 2006); 14(6): 809-821.
Venkatakrishnan, et al., "Structure and Dynamics of Adeno-Associated Virus Serotype 1 VP1-Unique N-Terminal Domain and Its Role in Capsid Trafficking". Journal of Virology (Apr. 2013); 87 (9): 4974-4984.
Watanabe, et al., "Tropisms of AAV for Subretinal Delivery to the Neonatal Mouse Retina and Its Application for In Vivo Rescue of Developmental Photoreceptor Disorders." PLoS ONE; vol. 8, No. 1, 12 paqes (Jan. 15, 2013).
Waterkamp, et al., "Isolation of targeted AAV2 vectors from novel virus display libraries." J. Gene. Med.; vol. 8, pp. 1307-1319 (Sep. 6, 2006).
White, et al., "Genetic modification of adeno-associated viral vector type 2 capsid enhances gene transfer efficiency in polarized human airway epithelial cells." Human Gene Therapy; vol. 19, pp. 1407-1414 (Dec. 2008).
White, et al., "Targeted gene delivery to vascular tissue in vivo by tropism-modified adeno-associated virus vectors." Circulation; vol. 109, pp. 513-519 (Feb. 3, 2004).
Wickham, et al., "Increased in vitro and in vivo gene transfer be adenovirus vectors containing chimeric fiber proteins." Journal of Virology; vol. 71, No. 11, pp. 8221-8229 (Nov. 1997).
Wiesmann, et al., "Crystal structure at 1.7 A resolution of VEGF in complex with domain 2 of the Flt-1 receptor." Cell. 1997; 91(5): 695-704.
Wobus, et al., "Monoclonal antibodies against the adeno-associated virus type 2 (AAV-2) capsid: epitope mapping and identification of capsid domains involved in AAV-2-cell interaction and neutralization of AAV-2 infection." J. Virol.; vol. 74, No. 19, pp. 9281-9293 (Oct. 2000).
Woodard, et al., "Heparan Sulfate Binding Promotes Accumulation of Intravitreally Delivered Adeno-associated Viral Vectors at the Retina for Enhanced Transduction but Weakly Influences Tropism". J Virol. (Oct. 14, 2016); 90(21): 9878-9888. Print Nov. 1, 2016.
Work, et al., "Vascular bed-targeted in vivo gene delivery using tropism-modified adeno-associated viruses." Mol. Ther.; vol. 13, No. 4, pp. 683-693 (Apr. 2006).
Wu, et al., "Mutational analysis of the adeno-associated virus type 2 (AAV2) capsid gene and construction of AAV2 vectors with altered tropism." Journal of Virology (2000); vol. 71, No. 18, pp. 8635-8647.
Wu, et al., "α2,3 and α2,6 N-Linked Sialic Acids Facilitate Efficient Binding and Transduction by Adeno-Associated Virus Types 1 and 6.", Journal of Virology (2006); vol. 80, No. 18, pp. 9093-9103.
Xiao et al. "Gene Therapy Vectors Based on Adeno-Associated Virus Type 1." Journal of Virology (1999); 73:5, p. 3994-4003.

(56) References Cited

OTHER PUBLICATIONS

Xiao, et al.; "Adenovirus-facilitated nuclear translocation of adeno-associated virus type 2." Journal of Virology; vol. 76, No. 22, p. 11505-11517 (Nov. 2002).

Xie, et al., "The atomic structure of adeno-associated virus (AAV-2), a vector for human gene therapy." PNAS; vol. 99, No. 16, p. 10405-10410 (Aug. 6, 2002).

Yang, et al., "Directed Evolution of Adeno=Associated Virus (AAV) as Vector for Muscle Gene Therapy." Methods in Molecular Biology; vol. 709, pp. 127-139 (2011).

Yang, et al., "A myocardium tropic adeno-associated virus (AAV) evolved by DNA shuffling and in vivo selection." PNAS; vol. 106, No. 10, pp. 3946-3951 (Mar. 10, 2009).

Yokoyama, et al. "Photoreceptor-specific activity of the human interphotoreceptor retinoid-binding protein (IRBP) promoter in transgenic mice." Experimental Eye Research (Aug. 1992); 55(2): 225-233.

Young et al. "A Short, Highly Active Photoreceptor-Specific Enhancer/Promoter Region Upstream of the Human Rhodopsin Kinase Gene." Opthalmol. Vis. Sci. (Sep. 2003); 44(9): 4076-4085.

Zabner, et al., "Adeno-associated virus type 5 (AAV5) but not AAV2 binds to the apical surfaces of airway epithelia and facilitates gene transfer." J Virol.; No. 74, No. 8, pp. 3852-3858 (Apr. 2000).

Zhao, et al., "Molecular evolution by staggered extension process (StEP) in vitro recombination." Nat Biotechnol; vol. 16, No. 3, pp. 258-261 (Mar. 1998).

Zolotukhin, et al., "Recombinant adeno-associated virus purification using novel methods improves infectious titer and yield." Gene Therapy (1999); vol. 6, pp. 973-985.

\* cited by examiner

FIG. 1B
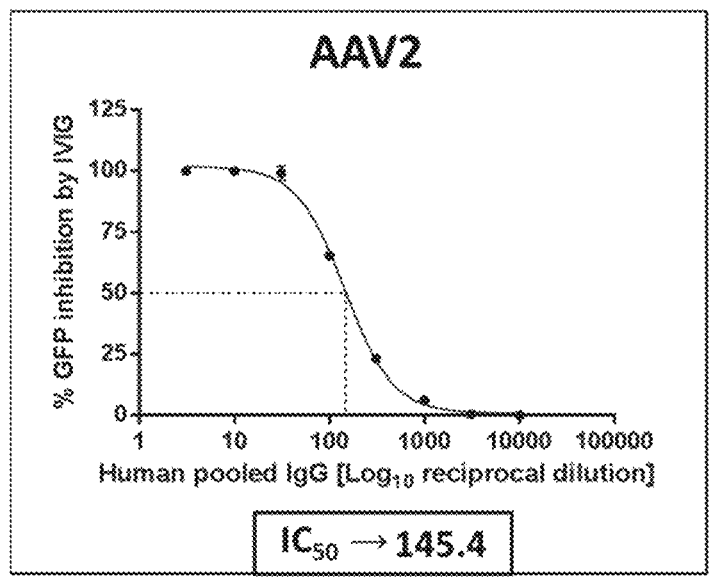
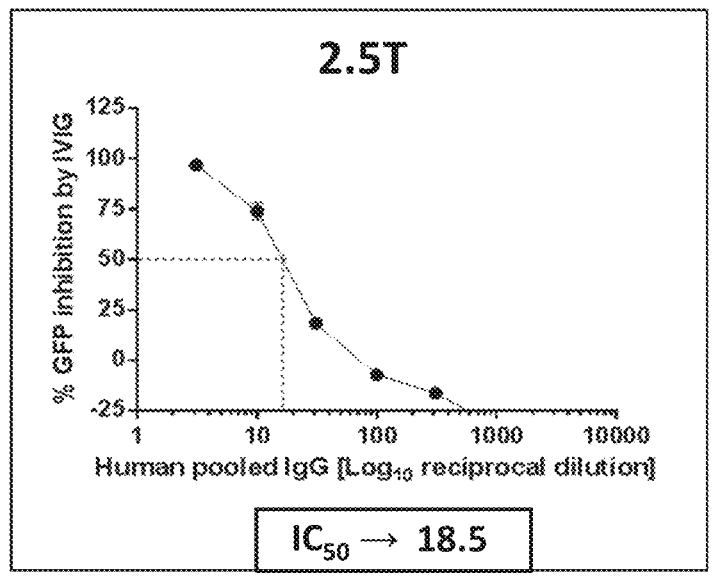

FIG. 3B

(i) AAV7m8: S T N L Q R G N L A L G E T T T R P A R Q A A T A D (aa# 580-604)

(ii) 7m8 10mer: L A L G E T T R P A (aa# 1-10)

7m8 insertion points: −12, −9, −6, −3, 0, +3

(iii) AAV2.5T: A T N N Q S S T T A P T T G T (aa# 571-585)

(iv) 2.5T/7m8(0): A T N N Q S S T L A L G E T T R P A T A P T T G T (aa# 571-595)

(v) 2.5T/7m8(+3): A T N N Q S S T T L A L G E T T R P A A P T T G T (aa# 571-595)

(vi) 2.5T/7m8(−3): A T N N Q S S L A L G E T T R P A T T A P T T G T (aa# 571-588, 579-585)

(vii) 2.5T/7m8(−6): A T N N Q S L A L G E T T R P A S T T A P T T G T (aa# 571-595)

(viii) 2.5T/7m8(−9): A T N N Q L A L G E T T R P A S S T T A P T T G T (aa# 571-595)

(ix) 2.5T/7m8(−12): A T N N L A L G E T T R P A Q S S T T A P T T G T (aa# 571-595)

(x) 2.5T/7m8(+3)-2pt: A T N N Q R S T R L A L G E T T R P A A P T T G T (aa# 571-595)

(xi) 2.5T/7m8(−12)-2pt: A T N N L A L G E T T R P A Q R S T R A P T T G T (aa# 571-595)

(xii) 2.5T/7m8(0)-sHSPG(correct): A T N N Q R G N L A L G E T T R P A R Q A T T G T (aa# 571-595)

(xiii) 2.5T/7m8(0)-sHSPG(extra 2): A T N N Q R G N L A L G E T T R P A R Q A A P T T G T (aa# 571-597)

(xiv) 2.5T/7m8(0)-IHSPG(correct): A T N L Q R G N L A L G E T T R P A R Q A A T T (aa# 571-595)

(xv) 2.5T/7m8(−3)-IHSPG(correct): A T N L Q R G L A L G E T T R P A R Q A A T T (aa# 571-595)

(xvi) 2.5T/7m8(−12)-sHSPG(extra 2): A T N N L A L G E T T R P A Q R G N R Q A A P T T G T (aa# 571-597)

(xvii) 2.5T/7m8(−12)-IHSPG(extra 8): A T N N L A L G E T T R P A Q N L Q R G N R Q A A T A P T T G T (aa# 571-603)

FIG. 4A

Capsid Sequence of 2.5T/7m8(+3) Δ2

MAADGYLPDWLEDTLSEGIRQWWKLKPGPPPPKPAERHKDDSRGLVLPGYKYLGPFNGLDKG
EPVNEADAAALEHDKAYDRQLDSGDNPYLKYNHADAEFQERLKEDTSFGGNLGRAVFQAKKR
VLEPFGLVEEGAKTAPTGKRIDDHFPKRKKARTEEDSKPSTSSDAEAGPSGSQQLQIPAQPA
SSLGADTMSAGGGGPLGDNNQGADGVGNASGDWHCDSTWMGDRVVTKSTRTWVLPSYNNHQY
REIKSGSVDGSNANAYFGYSTPWGYFDFNRFHSHWSPRDWQRLINNYWGFRPRSLRVKIFNI
QVKEVTVQDSTTTIANNLTSTVQVFTDDDYQLPYVVGNGTEGCLPAFPPQVFTLPQYGYATL
NRDNTENPTERSSFFCLEYFPSKMLRTGNNFEFTYNFEEVPFHSSFAPSQNLFKLANPLVDQ
YLYRFVSTNNTGGVQFNKNLAGRYANTYKNWFPGPMGRTQGWNLGSGVNRASVSAFATTNRM
ELEGASYQVPPQPNGMTNNLQGSNTYALENTMIFNSQPANPGTTATYLEGNMLITSESETQP
VNRVAYNVGGQMATNNQASTALALGETTRPAAPTTGTYNLQEIVPGSVWMERDVYLQGPIWA
KIPETGAHFHPSPAMGGFGLKHPPPMMLIKNTPVPGNITSFSDVPVSSFITQYSTGQVTVEM
EWELKKENSKRWNPEIQYTNNYNDPQFVDFAPDSTGEYRTTRPIGTRYLTRPL
(SEQ ID NO:1)

Swap residues

7m8 loop insert

FIG. 4B

Capsid Sequence of 2.5T/7m8(-12) elHSPG

MAADGYLPDWLEDTLSEGIRQWWKLKPGPPPPKPAERHKDDSRGLVLPGYKYLGPFNGLDKG
EPVNEADAAALEHDKAYDRQLDSGDNPYLKYNHADAEFQERLKEDTSFGGNLGRAVFQAKKR
VLEPFGLVEEGAKTAPTGKRIDDHFPKRKKARTEEDSKPSTSSDAEAGPSGSQQLQIPAQPA
SSLGADTMSAGGGGPLGDNNQGADGVGNASGDWHCDSTWMGDRVVTKSTRTWVLPSYNNHQY
REIKSGSVDGSNANAYFGYSTPWGYFDFNRFHSHWSPRDWQRLINNYWGFRPRSLRVKIFNI
QVKEVTVQDSTTTIANNLTSTVQVFTDDDYQLPYVVGNGTEGCLPAFPPQVFTLPQYGYATL
NRDNTENPTERSSFFCLEYFPSKMLRTGNNFEFTYNFEEVPFHSSFAPSQNLFKLANPLVDQ
YLYRFVSTNNTGGVQFNKNLAGRYANTYKNWFPGPMGRTQGWNLGSGVNRASVSAFATTNRM
ELEGASYQVPPQPNGMTNNLQGSNTYALENTMIFNSQPANPGTTATYLEGNMLITSESETQP
VNRVAYNVGGQMATNN<u>LALGETTRPAQ</u>APTTGTYNLQEIVPGSVWMERDV
YLQGPIWAKIPETGAHFHPSPAMGGFGLKHPPPMMLIKNTPVPGNITSFSDVPVSSFITQYS
TGQVTVEMEWELKKENSKRWNPEIQYTNNYNDPQFVDFAPDSTGEYRTTRPIGTRYLTRPL
(SEQ ID NO:2)

Swap residues

<u>7m8 loop insert</u>

FIG. 4C

Capsid Sequence of 2.5T/7m8(-3) IHSPG

MAADGYLPDWLEDTLSEGIRQWWKLKPGPPPPKPAERHKDDSRGLVLPGYKYLGPFNGLDKG
EPVNEADAAALEHDKAYDRQLDSGDNPYLKYNHADAEFQERLKEDTSFGGNLGRAVFQAKKR
VLEPFGLVEEGAKTAPTGKRIDDHFPKRKKARTEEDSKPSTSSDAEAGPSGSQQLQIPAQPA
SSLGADTMSAGGGGPLGDNNQGADGVGNASGDWHCDSTWMGDRVVTKSTRTWVLPSYNNHQY
REIKSGSVDGSNANAYFGYSTPWGYFDFNRFHSHWSPRDWQRLINNYWGFRPRSLRVKIFNI
QVKEVTVQDSTTTIANNLTSTVQVFTDDDYQLPYVVGNGTEGCLPAFPPQVFTLPQYGYATL
NRDNTENPTERSSFFCLEYFPSKMLRTGNNFEFTYNFEEVPFHSSFAPSQNLFKLANPLVDQ
YLYRFVSTNNTGGVQFNKNLAGRYANTYKNWFPGPMGRTQGWNLGSGVNRASVSAFATTNRM
ELEGASYQVPPQPNGMTNNLQGSNTYALENTMIFNSQPANPGTTATYLEGNMLITSESETQP
VNRVAYNVGGQMAT<mark>LQRG</mark>LALGETTRPA<mark>TGAHLS</mark>TYNLQEIVPGSVWMERDVYLQGPIWA
KIPETGAHFHPSPAMGGFGLKHPPPMMLIKNTPVPGNITSFSDVPVSSFITQYSTGQVTVEM
EWELKKENSKRWNPEIQYTNNYNDPQFVDFAPDSTGEYRTTRPIGTRYLTRPL
(SEQ ID NO:3)

<mark>Swap residues</mark>

7m8 loop insert

FIG. 7A 2.5T parent
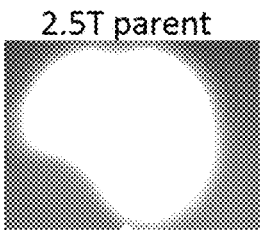
FIG. 7B 2.5T/7m8(-3)
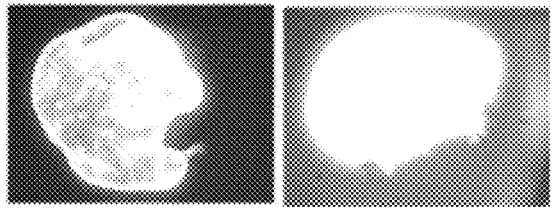
FIG. 7C 2.5T-S576R
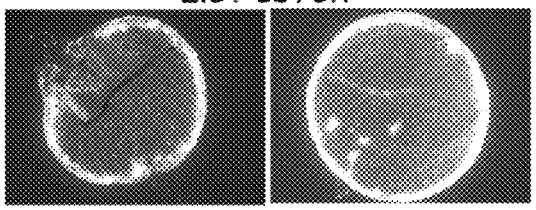
FIG. 7D 2.5T-T579R
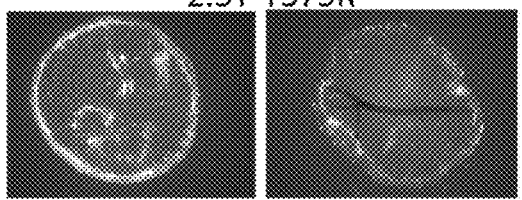
FIG. 7E 2.5T/7m8(+3)-2pt
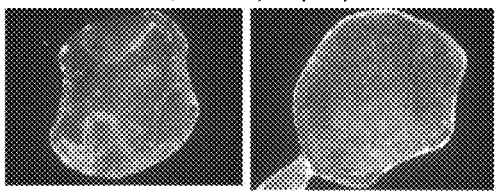
FIG. 7F 2.5T/7m8(0)-sHSPG
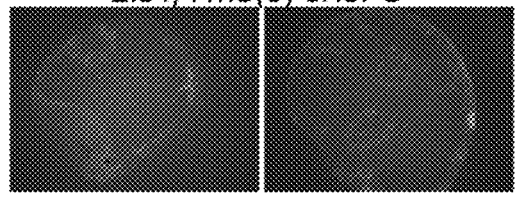
FIG. 7G 2.5T/7m8(-12)-2pt
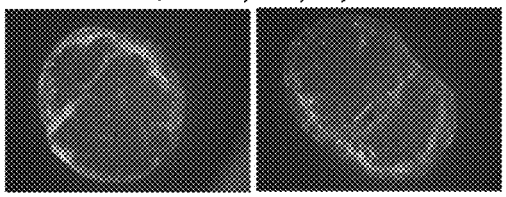
FIG. 7H 2.5T/7m8(-12)-sHSPG-extra2
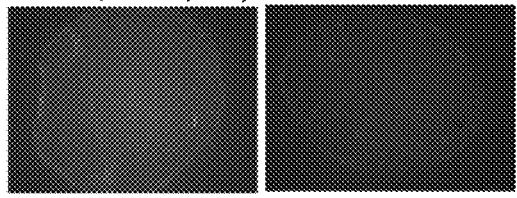
FIG. 7I 2.5T/7m8(-12)-lHSPG-extra8
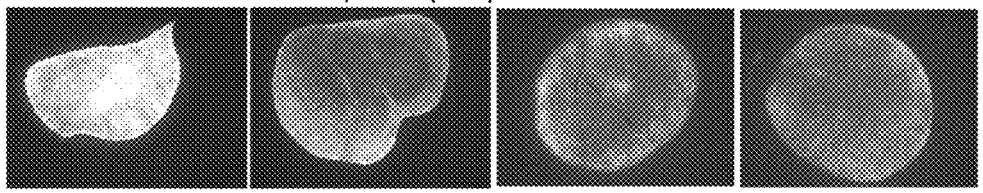
FIG. 7J 2.5T/7m8(-12)-lHSPG-correct
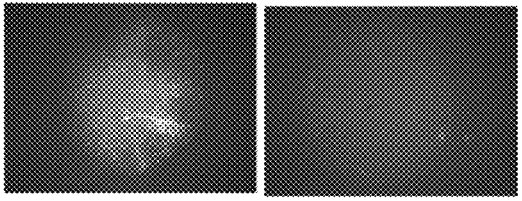
FIG. 7K 2.5T/7m8(-12)-sHSPG-correct
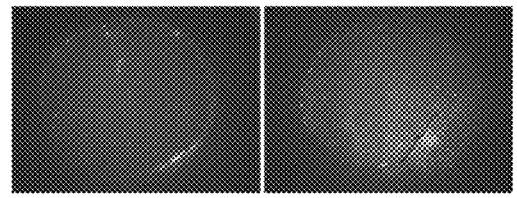

2.5T parent (overlay)　　　(GFP single channel)

2.5T-S576R (overlay)　　　(GFP single channel)

FIG. 10

| | | | |
|---|---|---|---|
| AAV-2 | 570 | PVATEQYGSVSTNLQRGNRQAATADVNTQGVLPGMVWQDRDV | 611 |
| AAV-1 | 571 | PVATERFGTVAVNFQSSSTDPATGDVHAMGALPGMVWQDRDV | 612 |
| AAV-5 | 560 | RVAYNVGGQMATNNQSSTTAPATGTYNLQEIVPGSVWMERDV | 601 |
| AAV-6 | 571 | PVATERFGTVAVNLQSSSTDPATGDVHVMGALPGMVWQDRDV | 612 |
| AAV-7 | 572 | PVATEEYGIVSSNLQAANTAAQTQVNNQGALPGMVWQDRDV | 613 |
| AAV-8 | 573 | PVATEEYGIVADNLQQANTAPQIGTVNSQGALPGMVWQDRDV | 614 |
| AAV-9 | 571 | PVATESYGQVATNHQSAQAQAQTGWVQNQGILPGMVWQNRDV | 612 |
| AAV-10 | 573 | PVATEQYGVVADNLQQANTGPIVGNVNSQGALPGMVWQNRDV | 614 |

2.5T/7m8(-12) eIHSPG

FIG. 17A
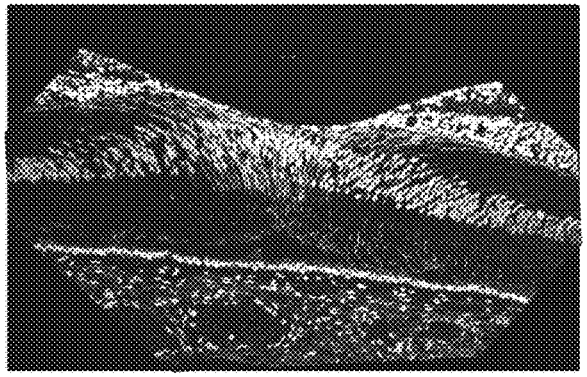 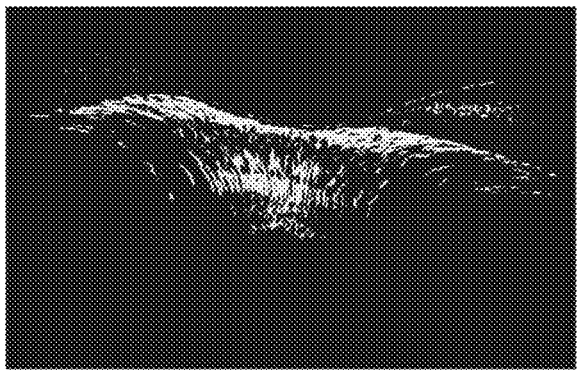
FIG. 17B
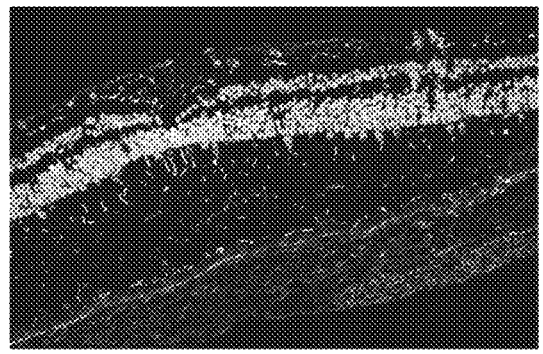 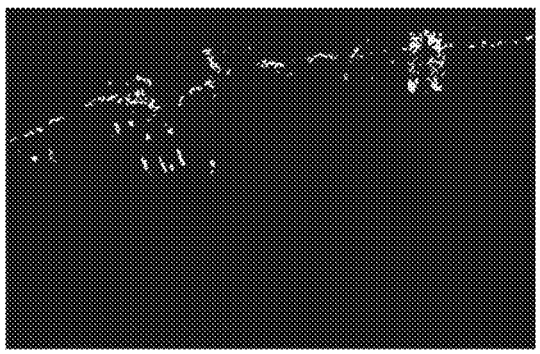
FIG. 17C
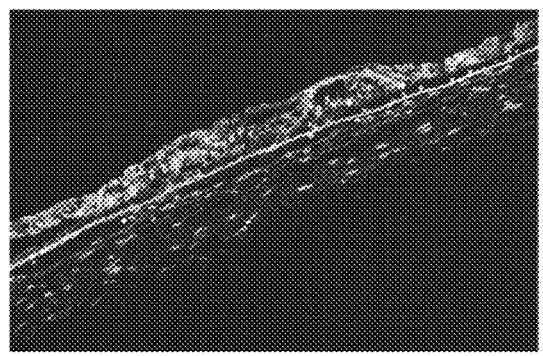 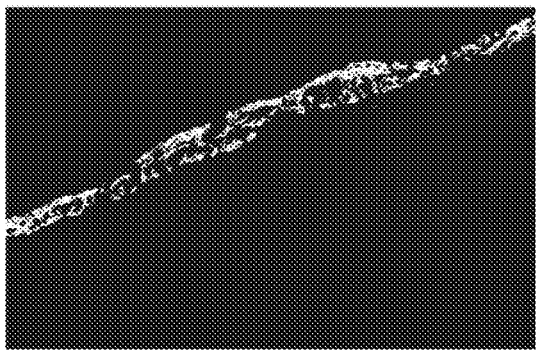

2.5T/7m8(+3) Δ2

FIG. 20
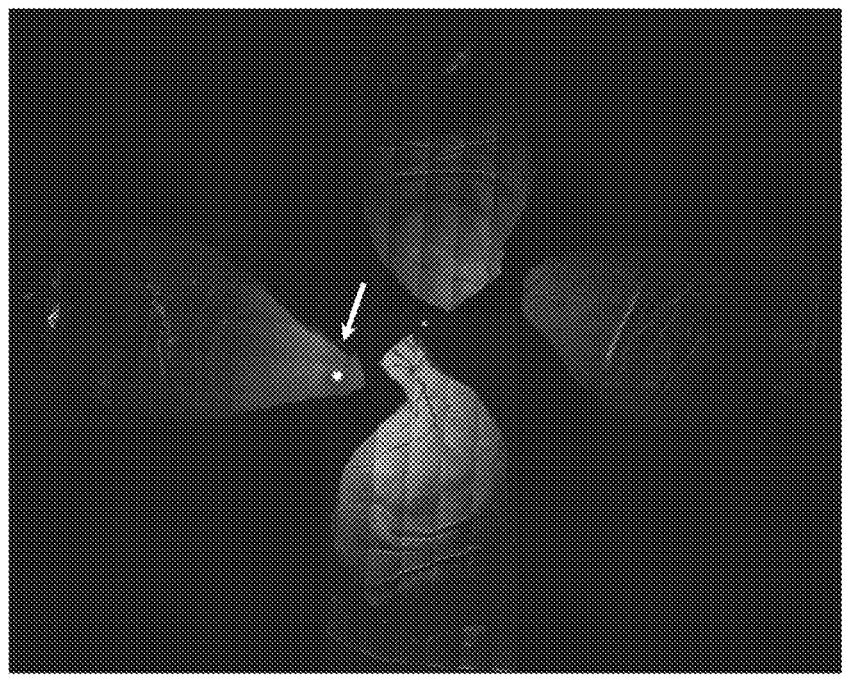
FIG. 21
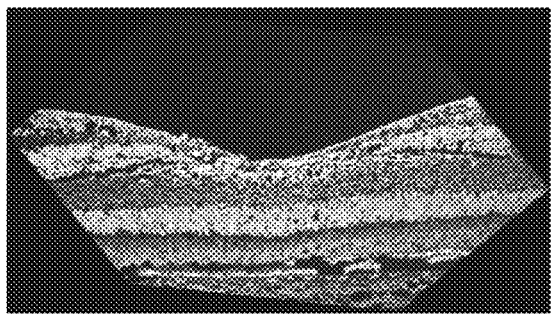 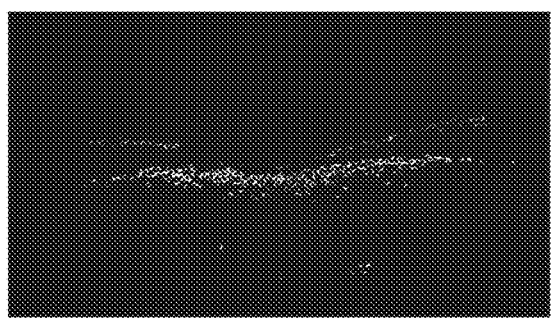

_US 11,192,925 B2_

MODIFIED AAV CAPSIDS AND USES THEREOF

CROSS REFERENCE TO RELATED APPLICATIONS

This application claims priority to U.S. Provisional Application No. 62/410,291, filed on Oct. 19, 2016, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_011_01US_ST25.txt. The text file is 107 KB, was created on Oct. 19, 2017, and is being submitted electronically via EFS-Web.

FIELD OF THE INVENTION

Embodiments of the present disclosure related to modified viral capsid proteins, including modified AAV capsid proteins, viruses and viral vectors comprising the modified AAV capsid proteins, and methods of using these viruses and viral vectors to deliver polypeptides to cells.

BACKGROUND OF THE INVENTION

A promising approach to treating and preventing genetic and other diseases and disorders is delivery of therapeutic agents with a gene therapy vector such as a viral vector. Illustrative examples of viral vectors suitable for gene therapy include but are not limited to retroviral vectors, lentiviral vectors, adenovirus vectors, herpes virus vectors, alphavirus vectors, and adeno-associated virus (AAV) vectors. AAV is a 4.7 kb, single-stranded DNA virus. Recombinant vectors based on AAV (rAAV vectors) are associated with excellent clinical safety, since wild-type AAV is non-pathogenic and has no etiologic association with any known diseases. In addition, AAV offers the capability for highly efficient gene delivery and sustained transgene expression in numerous tissues, including eye, muscle, lung and brain. Furthermore, AAV has shown promise in human clinical trials. One example is Leber's congenital amaurosis in which patients treated with a therapeutic delivered by a single subretinal administration of an rAAV vector have experienced sustained clinical benefit from expression of the therapeutic agent for more than four years from the initial date of treatment.

Certain challenges that remain with regard to the design of viral vectors for use in gene therapy include optimizing viral cell tropism and, particularly with respect to gene therapy of the eye, optimizing delivery to the retina. Thus, there is a need for optimized vectors for expressing genes in selected mammalian cells. The present invention addresses this need by providing modified AAV capsid proteins advantageous for the delivery of viral vectors to desired cells and tissues.

SUMMARY OF THE INVENTION

The present invention relates generally to the field of gene therapy, and in particular, to viral vectors useful for the delivery of nucleic acid segments encoding various agents (e.g., peptides, polypeptides, and polynucleotides, including, e.g., siRNAs, microRNAs, ribozymes, and catalytic RNA molecule), including therapeutic agents, to selected cells and tissues of vertebrate animals. In particular, aspects of the present invention include modified capsid proteins that are useful in gene therapy vectors, including for example, AAV vectors, for the delivery of agents to desired cells and for the treatment of mammalian diseases, disorders, and dysfunctions.

The disclosed compositions may be utilized in a variety of investigative, diagnostic and therapeutic regimens, including the prevention and treatment of a variety of human diseases.

In certain embodiments, the present invention includes a non-naturally-occurring modified AAV2.5T capsid protein, comprising one or more amino acid modifications. In certain embodiments, the modified AAV2.5T capsid protein comprises an amino acid insertion comprising or consisting of an amino acid sequence having at least 80%, at least 85%, or at least 90% homology to the amino acid sequence LALGETTRPA (SEQ ID NO:4), or a fragment of the amino acid sequence comprising at least five, at least six, at least seven, at least eight, or at least nine consecutive amino acids thereof, wherein the modified AAV2.5T capsid protein containing any of the aforesaid insertions is referred to as AAV2.5T/7m8. In certain embodiments, the 7m8 amino acid insertion is located between amino acid residues 574 and 588 of the AAV2.5T capsid protein.

In related embodiments, the present invention provides a modified AAV2.5T or AAV2.5T/7m8 capsid protein, wherein the capsid protein comprises an amino acid modification that introduces one or more amino acids of the AAV2 parental sequence into the capsid protein, and in particular embodiments, wherein the modification confers or enhances heparan sulfate binding to the capsid protein.

In certain aspects, the modified AAV2.5T capsid protein comprises at least one of the one or more of the following amino acid modifications: a S576R point mutation; a T579R point mutation; a substitution of amino acid residues 576-579 or amino acid residues 576-581 with the following amino acid residues: RGNRQA (SEQ ID NO:5); a substitution of amino acid residues 576-581 with the following amino acid residues: RGNRQAAP (SEQ ID NO:6); a substitution of amino acid residues 573-581 or amino acid residues 573-584 with the following amino acid residues: NLQRGNRQAATA (SEQ ID NO:7); or a substitution of amino acid residues 573-581 or amino acid residues 573-584 with the following amino acid residues: NLQRGNRQAATAAP (SEQ ID NO:8).

In particular aspects, the modified AAV2.5T/7m8 capsid protein comprises at least one of the one or more of the following amino acid modifications: a point mutation corresponding to a S576R point mutation in AAV2.5T; a point mutation corresponding to a T579R point mutation in AAV2.5T; a substitution corresponding to a substitution of amino acid residues 576-579 or amino acid residues 576-581 in AAV2.5T with the following amino acid residues: RGNRQA (SEQ ID NO:5); a substitution corresponding to a substitution of amino acid residues 576-579 or amino acid residues 576-581 in AAV2.5T with the amino acid residues: RGNRQAAP (SEQ ID NO:6) or NLQRGNRQAATA (SEQ ID NO:7); a substitution corresponding to a substitution of amino acid residues 573-579, amino acid residues 573-581, amino acid residues 573-583, or amino acid residues 573-584 in AAV2.5T with the following amino acid residues: NLQRGNRQAATA (SEQ ID NO:7); or a substitution corresponding to a substitution of amino acid residues 573-579, amino acid residues 573-581, amino acid residues 573-583, amino acid residues 573-584, or amino acid residues 576-583 in AAV2.5T with the following amino acid residues: NLQRGNRQAATAAP (SEQ ID NO:8).

In certain embodiments, a modified AAV2.5T capsid protein comprises at least one of the one or more of the following amino acid modifications: (a) a S576R point mutation; (b) a T579R point mutation; (c) a substitution of amino acid residues 576-579 or 576-581 with the following amino acid residues: RGNRQA (SEQ ID NO:5); (d) a substitution of amino acid residues 576-581 with the following amino acid residues: RGNRQAAP (SEQ ID NO:6); (e) a substitution of amino acid residues 573-579, 573-581 or 573-584 with the following amino acid residues: NLQRGNRQAATA (SEQ ID NO:7); or (f) a substitution of amino acid residues 573-581 or 573-584 with the following amino acid residues: NLQRGNRQAATAAP (SEQ ID NO:8).

In certain embodiments, a modified AAV2.5T/7m8 capsid protein comprises at least one or more of the following amino acid modifications: (a) a point mutation corresponding to a S576R point mutation in AAV2.5T; (b) a point mutation corresponding to a T579R point mutation in AAV2.5T; (c) a substitution corresponding to a substitution of amino acid residues 576-579 or 576-581 in AAV2.5T with the following amino acid residues: RGNRQA (SEQ ID NO:5); (d) a substitution corresponding to a substitution of amino acid residues 576-581 in AAV2.5T with the following amino acid residues: RGNRQAAP (SEQ ID NO:6); (e) a substitution corresponding to a substitution of amino acid residues 573-579, 573-581, 573-583, 573-584, 576-579, 576-581, 576-583 or 576-584 in AAV2.5T with the following amino acid residues: NLQRGNRQAATA (SEQ ID NO:7); or (f) a substitution corresponding to a substitution of amino acid residues 576-583, 576-584, 573-583 or 573-584 in AAV2.5T with the following amino acid residues: NLQRGNRQAATAAP (SEQ ID NO:8).

In particular embodiments, the modified capsid protein comprises one or modifications shown in any of the accompanying figures. In certain embodiments, the modified AAV2.5T/7m8 capsid protein is an AAV2.5T/7m8(0), AAV2.5T/7m8(+3), AAV2.5T/7m8(−3), or AAV2.5T/7m8 (−12). In particular embodiments, the modified capsid protein comprises a sequence shown in FIG. 4A, FIG. 4B or FIG. 4C or set forth in any of SEQ ID NOs:1-3.

In a related embodiment, the present invention includes a polynucleotide comprising a nucleic acid sequence encoding a modified AAV2.5T or AAV2.5T/7m8 capsid protein described herein. In certain embodiments, the nucleic acid sequence encoding the modified AAV2.5 or AAV2.5T capsid protein is operably linked to a promoter sequence. In particular embodiments, the polynucleotide further comprises a nucleic acid sequence encoding a rep protein.

A further related embodiment of the present invention includes a cell comprising an expression vector described herein. In further embodiments, the cell comprises a polynucleotide that encodes a therapeutic protein.

Another embodiment is a recombinant virus or viral vector comprising a modified capsid protein described herein. In certain embodiments, the recombinant virus or viral vector is an adeno-associated virus (AAV), optionally AAV2. In particular embodiments, the recombinant virus or viral vector is eluted from a heparan column at a salt concentration of about 0.2 M to about 0.4 M. In some embodiments, the recombinant virus or viral vector is capable of binding to and crossing the inner limiting membrane (ILM) when intravitreally injected into a mammal. In certain embodiments, the recombinant virus or viral vector comprises a polynucleotide sequence that encodes a therapeutic agent. In certain embodiments, the therapeutic agent is a therapeutic protein. In other embodiments, the therapeutic agent is a therapeutic nucleic acid. Exemplary therapeutic nucleic acids include siRNA, shRNA, and ribozymes. In particular embodiments, the therapeutic protein is an anti-vascular endothelial growth factor (anti-VEGF) agent. Exemplary anti-VEGF agents include aflibercept, ranibizumab and bevacizumab.

In certain embodiments, a recombinant virus or viral vector described herein has an altered cellular tropism as compared to AAV2.5T or AAV2.5T/7m8. In some embodiments, the recombinant virus or viral vector is a AAV2.5T comprising a modified capsid protein comprising: (a) a S576R point mutation; or (b) a T579R point mutation, wherein the recombinant virus or viral vector has a greater tropism for retinal ganglion cells ("RGC") than AAV2.5T. In other embodiments, the recombinant virus or viral vector is a AAV2.5T/7m8 comprising a modified capsid protein comprising: (a) a S576R point mutation; and (b) a T579R point mutation, wherein the recombinant virus or viral vector has a greater tropism for Müller cells than AAV2.5T/7m8. In other embodiments, the recombinant virus or viral vector is a AAV2.5T/7m8 comprising a modified capsid protein comprising a substitution of amino acid residues corresponding to 573-584 in AAV2.5T/7m8 with the following amino acid residues: NLQRGNRQAATA (SEQ ID NO:7), wherein the recombinant virus or viral vector has a greater tropism for retinal cells than AAV2.5T/7m8.

In further related embodiments, the present invention includes a pharmaceutical composition comprising a recombinant virus or viral vector described herein.

The present invention also includes a related method of providing a protein to a retina of a subject, comprising administering to the subject by intravitreal injection the recombinant virus or viral vector or pharmaceutical composition described herein, wherein the recombinant virus or viral vector comprises a polynucleotide sequence that encodes the protein.

The present invention further includes a method of providing a therapeutic gene product (e.g., a therapeutic protein) to a retina of a subject in need thereof, comprising administering to the subject by intravitreal injection a pharmaceutical composition comprising a recombinant virus or viral vector described herein, wherein the recombinant virus or viral vector comprises a polynucleotide encoding the therapeutic gene product. In particular embodiments, subject has been diagnosed with or is considered at risk of an ocular disease or disorder. In particular embodiments, the subject has been diagnosed with or is suspected of having or being at risk of developing one or more conditions selected from the group consisting of: age-related macular degeneration (AMD), wet-AMD, dry-AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, and diabetic retinal edema.

The present invention further provides a method of altering the tropism of an AAV2.5T or AAV2.5T/7m8 virus or viral vector, comprising introducing one or more amino acid modifications that confers or increases heparan sulfate binding to a capsid protein of the virus or viral vector. In particular embodiments, the amino acid modification introduces one or more amino acids of AAV2 into the capsid protein. In particular embodiments, at least one of the one or more amino acid modifications comprises: a point mutation corresponding to a S576R point mutation in AAV2.5T; a point mutation corresponding to a T579R point mutation in AAV2.5T; a substitution corresponding to a substitution of amino acid residues 576-581 in AAV2.5T with amino acid residues: RGNRQA (SEQ ID NO:5) or RGNRQAAP (SEQ ID NO:6); or a substitution corresponding to a substitution of amino acid residues 573-581, 576-579, 573-583 in AAV2.5T with amino acid residues: NLQRGNRQAATA (SEQ ID NO:7) or NLQRGNRQAATAAP (SEQ ID NO:8). In one embodiment, the amino acid modification comprises: (a) a S576R point mutation; or (b) a T579R point mutation, wherein the virus or viral vector has a greater tropism for RGC than AAV2.5T. In one embodiment, the amino acid modification comprises: (a) a S576R point mutation; and (b) a T579R point mutation, wherein the virus or viral vector has a greater tropism for Müller cells than AAV2.5T/7m8. In one embodiment, the amino acid modification comprises a substitution of amino acid residues corresponding to 576-579 in AAV2.5T with the following amino acid residues: NLQRGNRQAATA (SEQ ID NO:7), wherein the recombinant virus or viral vector has a greater tropism for retinal cells than AAV2.5T/7m8. In particular embodiment, the recombinant virus or viral vector is AAV2.5T/7m8-12-lHSPG (extra8) comprising a modified capsid sequence shown in FIG. 3C.

In another embodiment, the present invention includes a method for selectively delivering a polypeptide to RGC of a subject, comprising administering to the subject a modified AAV2.5T virus or viral vector comprising a polynucleotide that encodes the polypeptide, wherein the virus or viral vector comprises a capsid protein comprising a S576R point mutation or a T579R point mutation.

In another embodiment, the present invention includes a method for selectively delivering a polypeptide to Müller cells of a subject, comprising administering to the subject a modified AAV2.5T/7m8 virus or viral vector comprising a polynucleotide that encodes the polypeptide, where the virus comprises a capsid protein comprising: (a) a S576R point mutation; and (b) a T579R point mutation, optionally AAV2.5T/7m8(+3)-2pt.

In another embodiments, the present invention includes a method for selectively delivering a polypeptide to retinal cells of a subject, comprising administering to the subject a modified AAV2.5T/7m8 virus or viral vector comprising a polynucleotide that encodes the polypeptide, where the virus comprises a capsid protein comprising a substitution of amino acid residues corresponding to amino acid residues 576-579 in AAV2.5T with amino acid residues: NLQRGNRQAATA (SEQ ID NO:7) or NLQRGNRQAATAAP (SEQ ID NO:8), or a substitution of amino acid residues corresponding to amino acid residues 573-579 in AAV2.5T with amino acid residues: TNQNLQRGNRQAATA (SEQ ID NO:9) or TNQNLQRGNRQAATAAP (SEQ ID NO:10).

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 1B provides graphs showing the results of in vitro IVIg assays, which demonstrate that AAV2.5T has a better neutralizing antibody (nAb) profile compare to AAV2 as evidenced by its reduced $IC_{50}$.

FIG. 3B provides a sequence alignment of the HSPG binding region of indicated capsids (SEQ ID NOs: 4, 46 and 54-68). Sequences from the parental AAV2 sequence are indicated in light grey, and the 7m8 sequence (LALGETTRPA; SEQ ID NO:4) is indicated in dark grey. AAV2.5T/7m8 (SEQ ID NOs: 55-68) includes a 10 amino acid insertion, LALGETTRPA (SEQ ID NO:4), as compared to 2.5T (SEQ ID NO:46). The location of the insertion is indicated by the parenthetical following "7m8" in the various versions of 2.5T/7m8 (e.g., 2.5T/7m8(+3) (SEQ ID NO:56), 2.5T/7m8(0) (SEQ ID NO:55). In AAV2.5T/7m8, the 7m8 sequence is inserted between T578 and T579 of the AAV2.5T sequence, which is equivalent to the location of the 7m8 insertion in AAV2/7m8 (SEQ ID NO:54). AAV2.5T/7m8(+3) (SEQ ID NO:56) had the 7m8 insertion shifted one residue towards the C-terminus (+3 indicating the shift 3 nucleotides in the DNA sequence used to produce the recombinant capsid); the capsids designated " . . . 7m8(−3)"; " . . . 7m8(−6)"; " . . . 7m8(−9)"; and " . . . 7m8(−12)" are shifted 1, 2, 3, and 4 amino acids, respectively, toward the N-terminus. 2.5T/7m8(+3)−2pt (SEQ ID NO:61) includes the indicated point mutations to arginine at amino acid residues 576 and 579; 2.5T/7m8(0)-sHSPG (SEQ ID NO:63) includes a replacement of amino acid residues 576-591 by the indicated HSPG binding loop of AAV2, which also includes the 7m8 10 amino acid insertion within the HSPG binding loop; and 2.5T/7m8(0)−lHSPG (SEQ ID NO:65) includes a replacement of amino acid residues 573-591 by the indicated longer version of the HSPG binding loop of AAV2, which also includes the 7m8

10 amino acid insertion within the HSPG binding loop. 2.5T/7m8-12-sHSPG(extra 2) (SEQ ID NO:67) includes a replacement of amino acid residues 576-579 by the indicated HSPG binding loop of AAV2; 2.5T/7m8-12-lHSPG(extra8) (SEQ ID NO:68) includes a replacement of amino acid residues 576-579 by the indicated HSPG binding loop of AAV2; 2.5T/7m8-12-sHSPG(correct) includes a replacement of amino acid residues 575-581 of 2.5T by the indicated HSPG binding loop of AAV2; and 2.5T/7m8-12-lHSPG(correct) includes a replacement of amino acid residues 573-581 of AAV2.5T by the indicated longer version of the HSPG binding loop of AAV2, which also includes the 7m8 10 amino acid insertion within the HSPG binding loop.

FIG. 4A provides the amino acid sequence of the capsid protein of AAV2.5T/7m8(+3) Δ2 (also referred to as 2.5T/7m8(+3)−2pt) (SEQ ID NO:1).

FIG. 4B provides the amino acid sequence of the capsid protein of AAV2.5T/7m8(−12) elHSPG (also referred to as 2.5T/7m8(−12)−lHSPG(extra8)) (SEQ ID NO:2).

FIG. 4C provides the amino acid sequence of the capsid protein of AAV2.5T/7m8(−3) lHSPG (SEQ ID NO:3).

Figure 5:
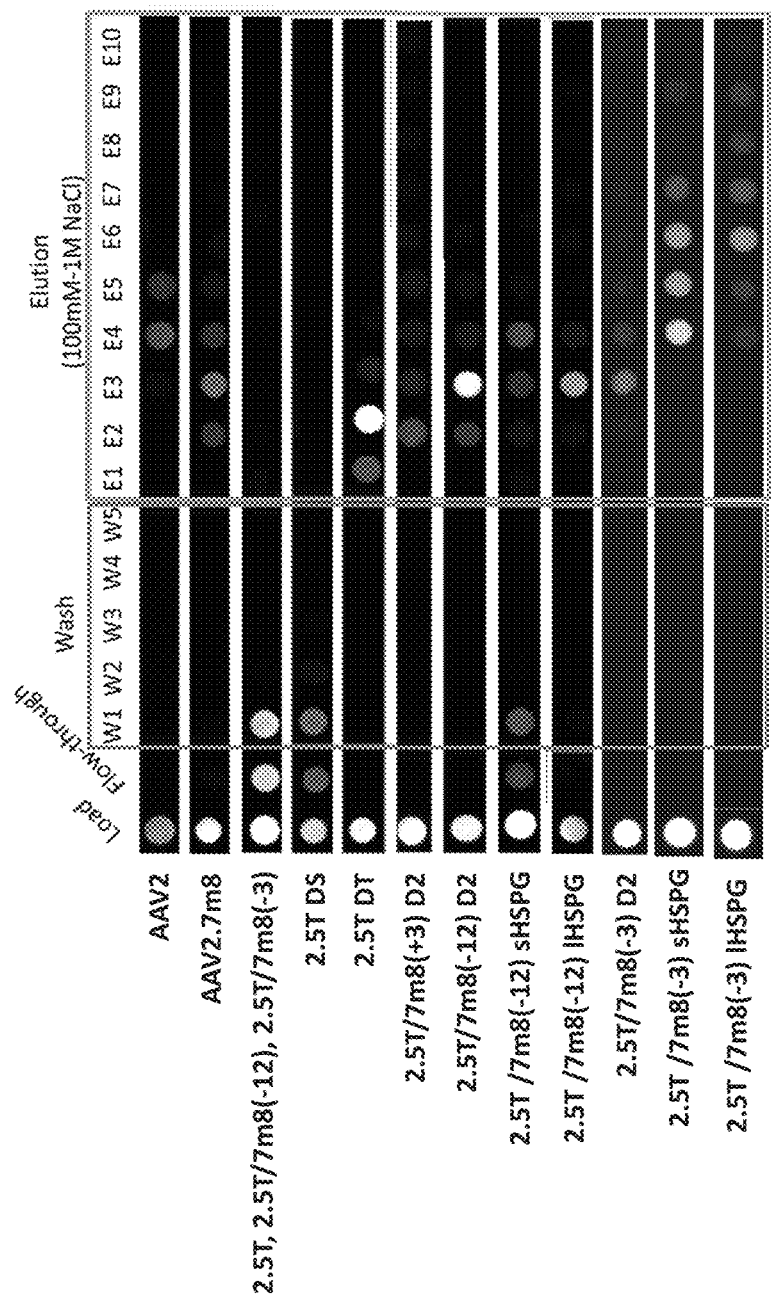

FIG. 5 shows the dot blot results of HSPG column fractions from different 2.5 swap variants. Elutes E1 to E10 have increasing concentrations of NaCl of 0.1M (E1), 0.2M (E2), 0.3M (E3), 0.4M (E4), 0.5M (E5), 0.6M (E6), 0.7M (E7), 0.8M (E8), 0.9M (E9) and 1.0M (E10).

Figure 6:
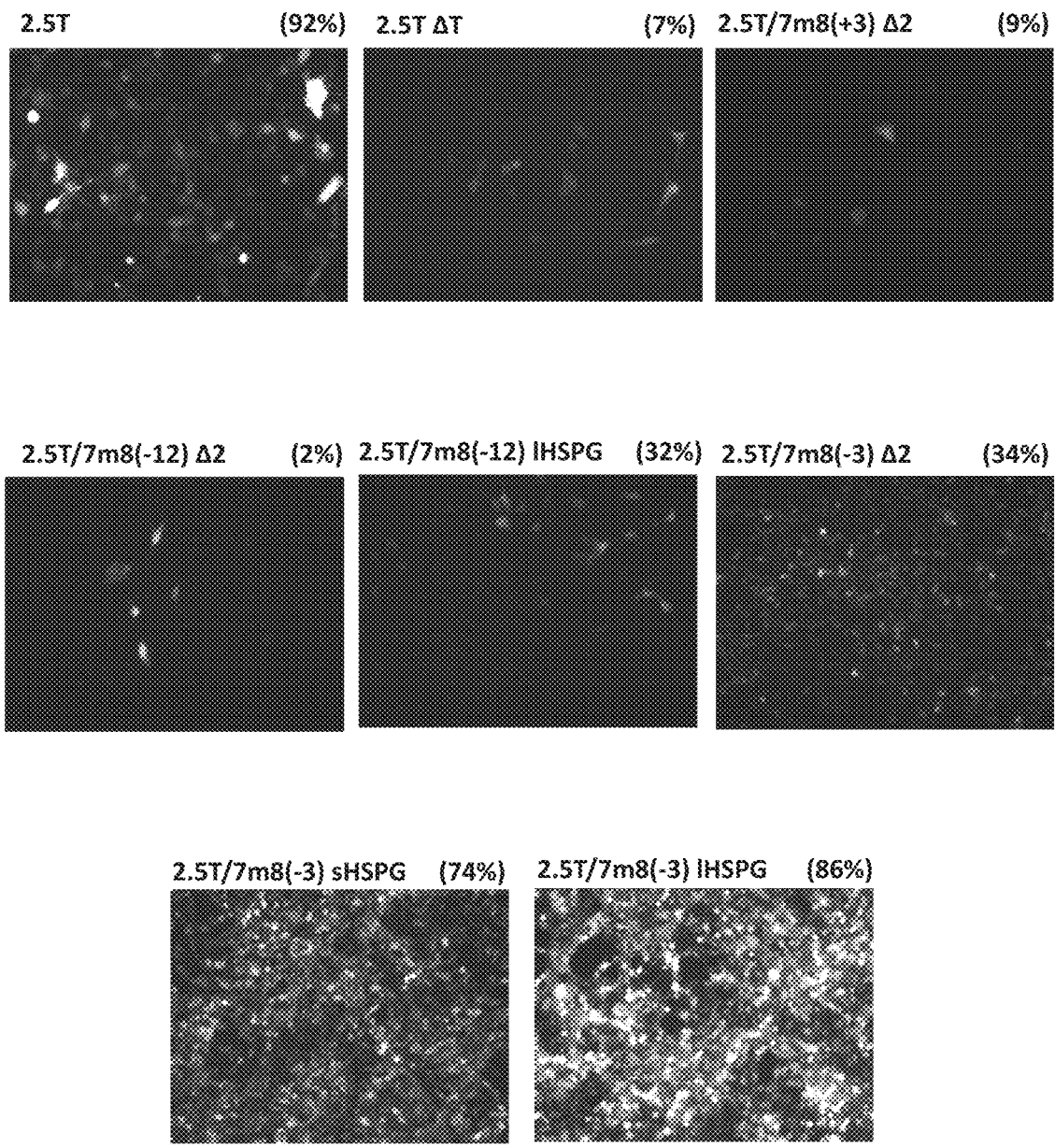

FIG. 6 shows live fluorescent images of GFP expression in HEK293 cells transduced with the indicated HSPG swap variants. The percentage of HEK293 cells expressing GFP is indicated in parenthesis above the image.

FIGS. 7A-7K show live images of GFP expression in pig retinal explants two weeks following infection with the indicated AAV vector expressing GFP. FIG. 7A shows GFP expression using the 2.5T vector; FIG. 7B shows GFP expression using the 2.5T/7m8(−3) vector; FIG. 7C shows GFP expression using the 2.5T-S576R vector; FIG. 7D shows GFP expression using the 2.5T-T579R vector; FIG. 7E shows GFP expression using the 2.5T/7m8(+3)−2pt vector; FIG. 7F shows GFP expression using the 2.5T/7m8 (0)-sHSPG vector; FIG. 7G shows GFP expression using the 2.5T/7m8(−12)−2pt vector; FIG. 7H shows GFP expression using the 2.5T/7m8(−1.2)-sHSPG-extra2 vector; FIG. 7I shows GFP expression using the 2.5T/7m8(−12)-lHSPG-extra8 vector; FIG. 7J shows GFP expression using the 2.5T/7m8(−12)-lHSPG-correct vector; and FIG. 7K shows GFP expression using the 2.5T/7m8(−12)-sHSPG-correct vector.

Figure 8A:
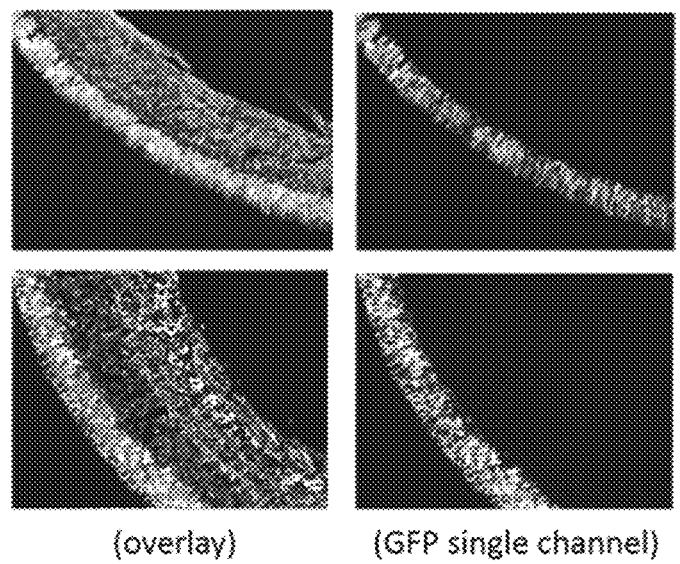
Figure 8B:
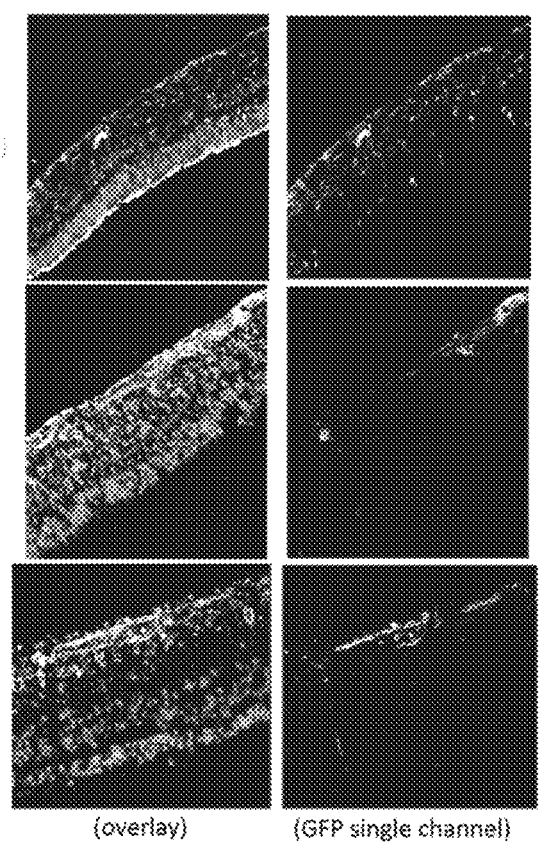
Figure 8C:
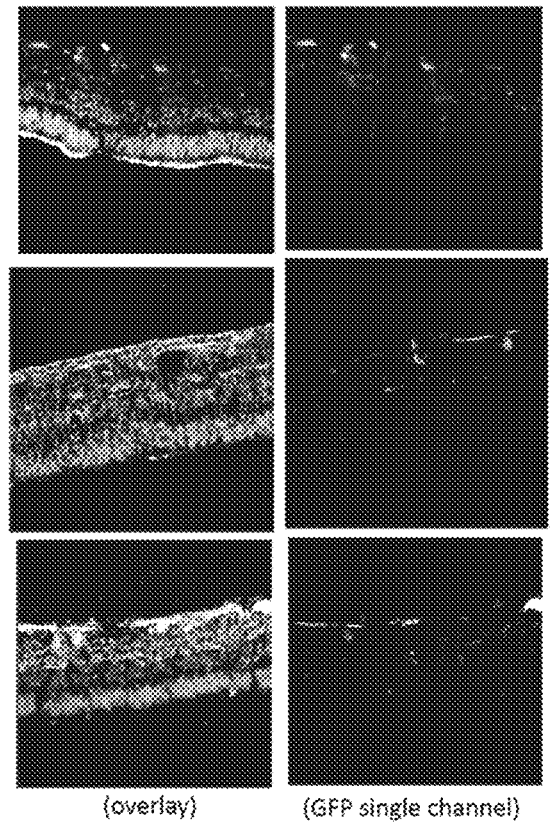
Figure 8D:
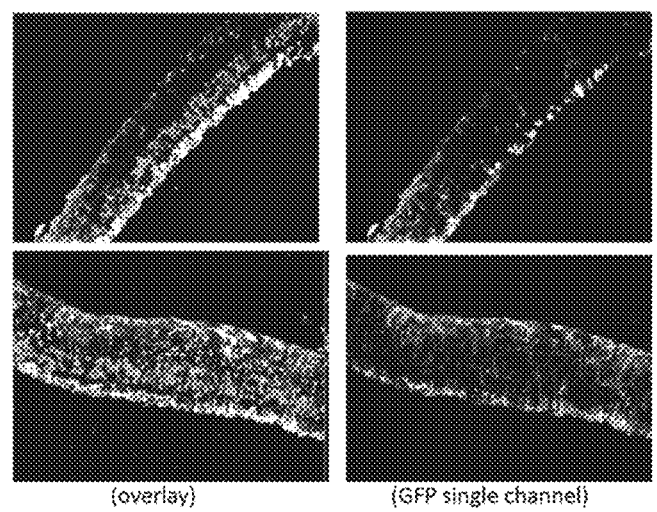
Figure 8E:
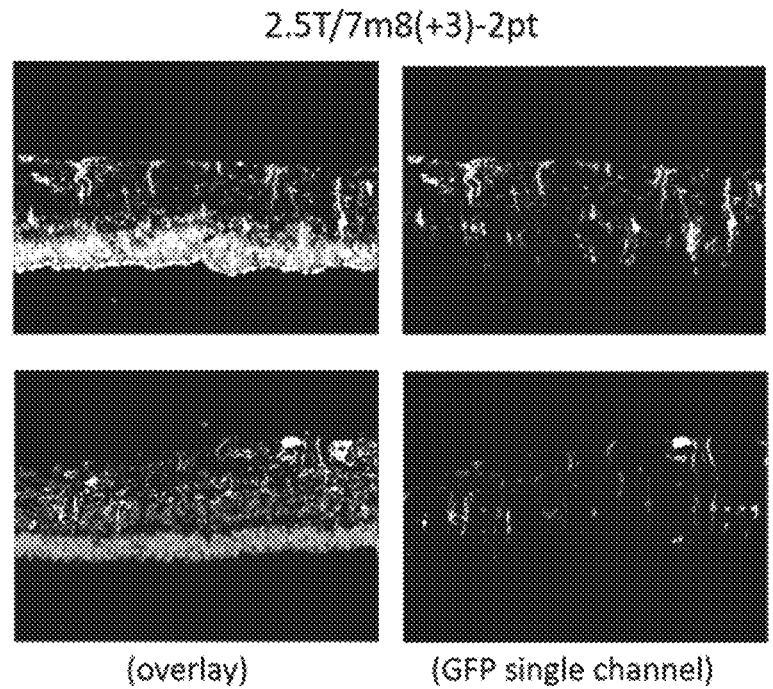
Figure 8F:
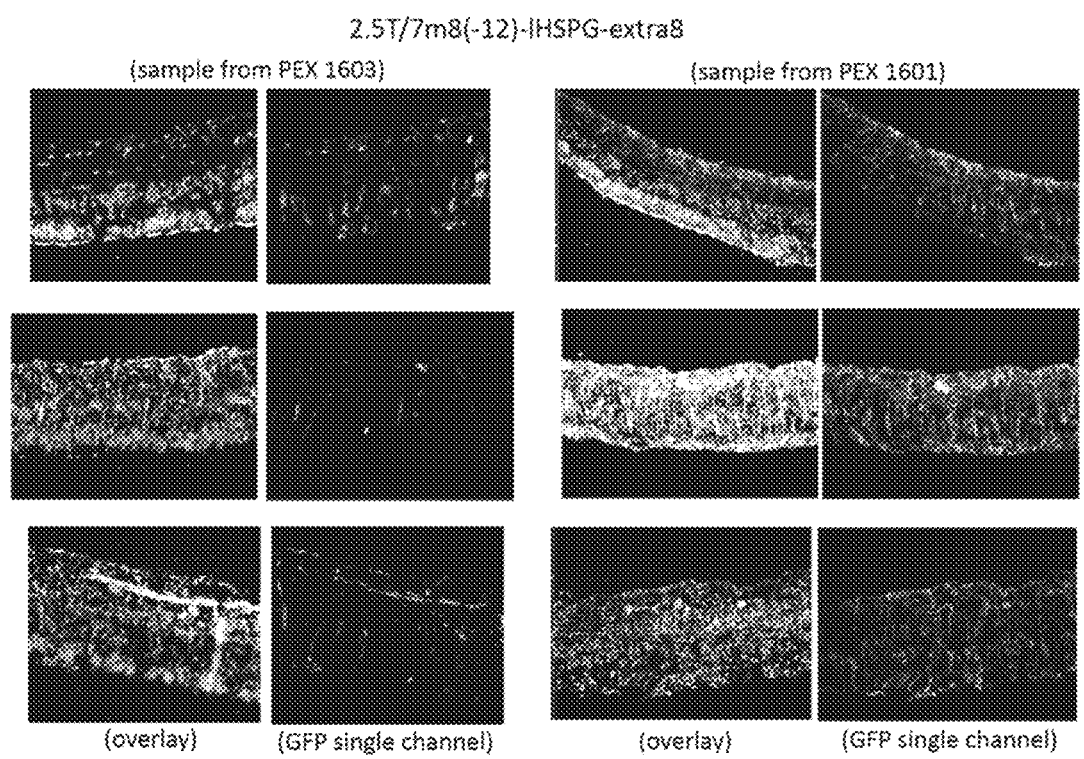

FIGS. 8A-8F provide immunofluorescence images of GFP expression in retinal cells of cryosectioned pig explants two weeks following infection with the indicated AAV viruses expressing GFP. In the immunofluorescence images, the cells are stained with DAPI, and probed with antibodies to detect the following proteins: Rho (to detect rod cells), Tuj1 (to detect RGC), GFAP (to detect Müller cells) and CX10 (to detect bipolar cells). In each pair of images, the left panel shows overlap of the stains, and the right panel shows GFP single channel staining. FIG. 8A shows cells infected with the 2.5T parent vector; FIG. 8B shows cells infected with the 2.5T-S576 vector; FIG. 8C shows cells infected with the T579R vector; FIG. 8D shows cells infected with the 2.5T/7m8(−3) vector; FIG. 8E shows cells infected with the 2.5T/7m8(+3)−2pt vector; and FIG. 8F shows cells transfected with the 2.5T/7m8(−12)-lHSPG-extra8 vector.

Figure 9:
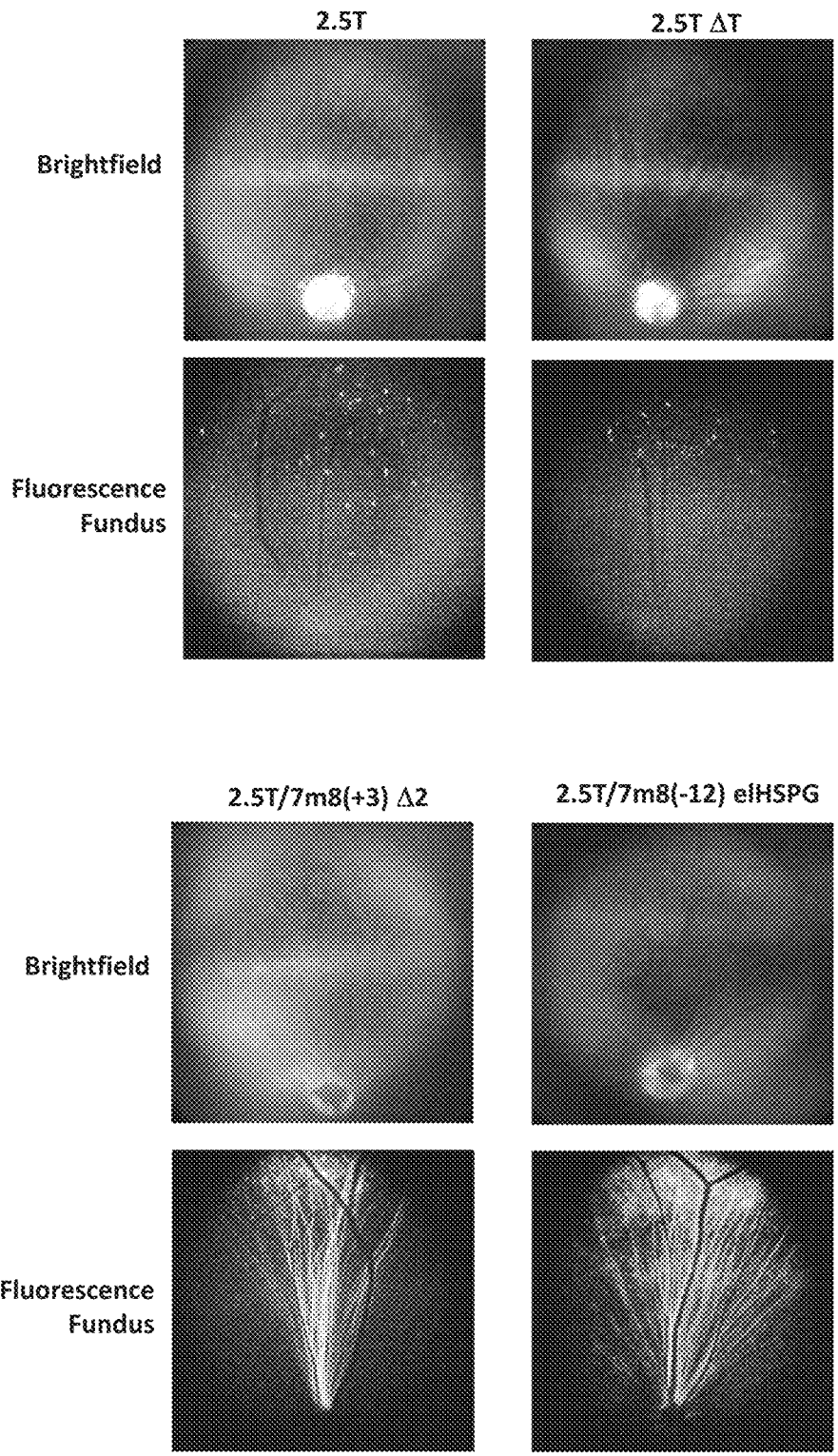
Figure 9:
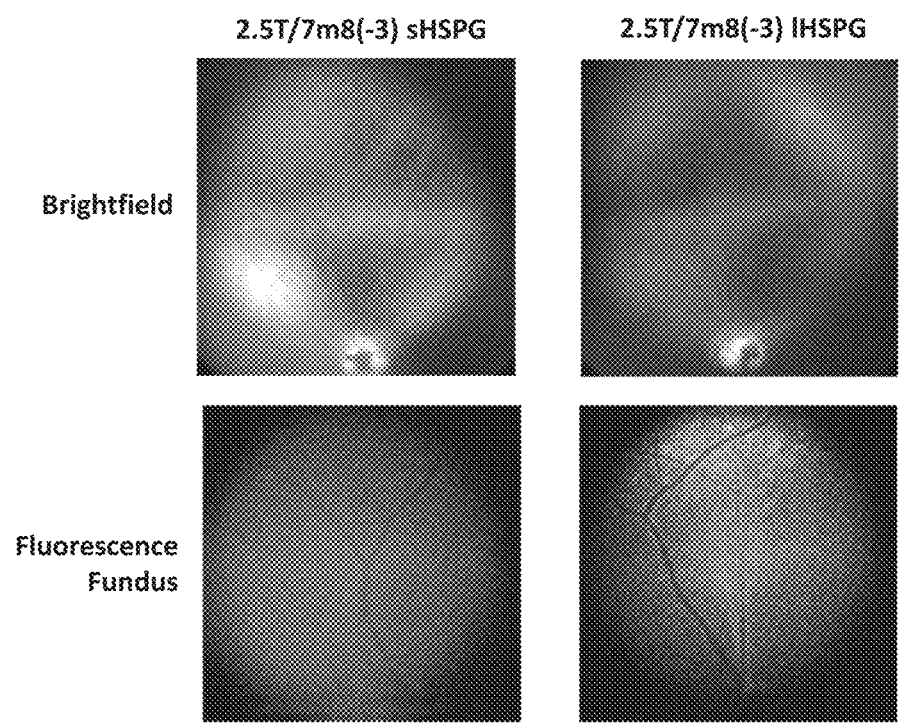
Figure 11A:
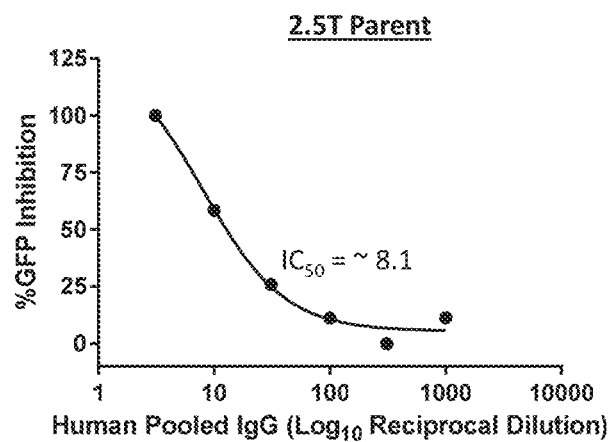
Figure 11B:
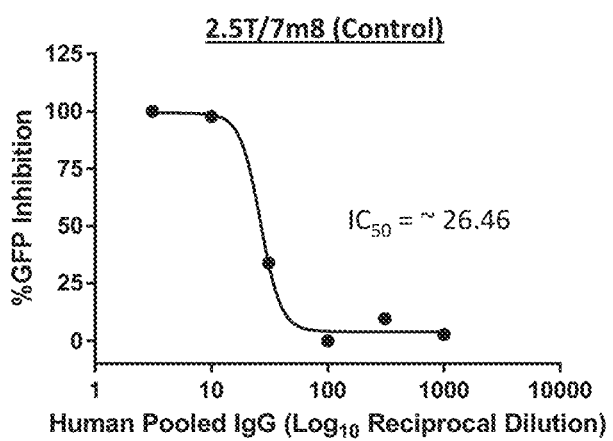
Figure 11C:
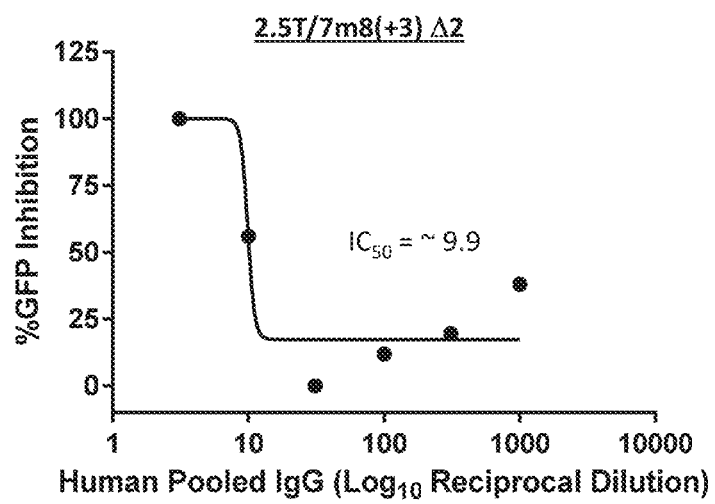
Figure 11D:
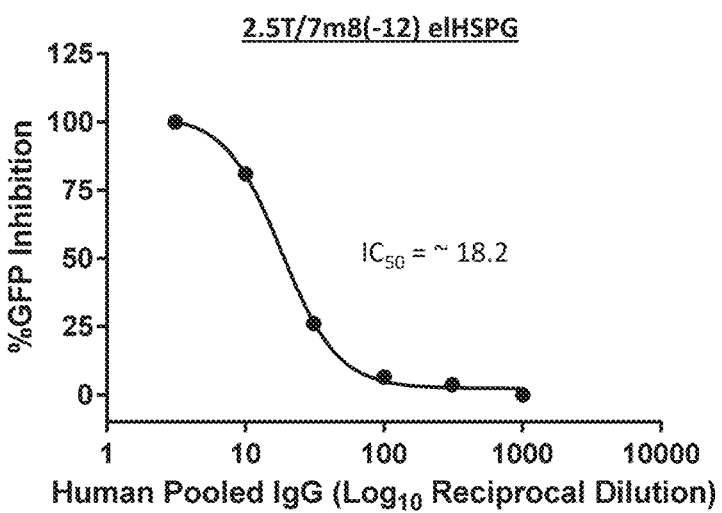
Figure 11E:
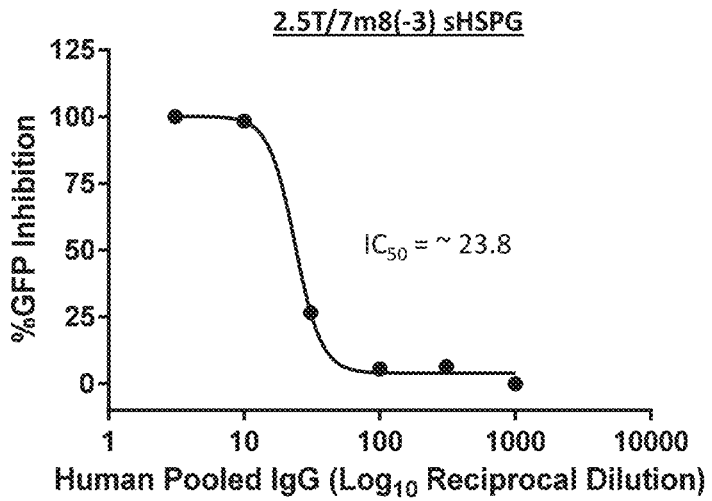

FIG. 9 shows brightfield images (top panels) and fluorescence fundus images (lower panels) of gerbil retina eight weeks following intravitreal administration of the indicated viruses expressing GFP.

FIG. 10 provides amino acid sequences corresponding to amino acids 570-610 of AAV2 of AAV capsid protein VP1 of various AAV serotypes (SEQ ID NOs: 69-76).

Figure 1A:
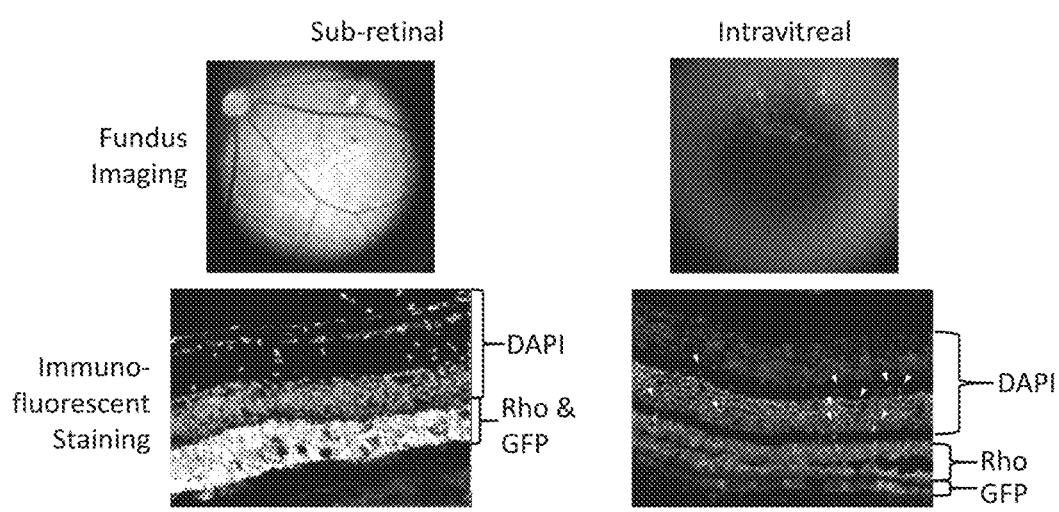
FIG. 1A provides fundus images (top panels) and immunofluorescent stains (bottom panels) of retina following sub-retinal (left panels) or intravitreal injection (right panels) of AAV2.5T virus encoding green fluorescent protein (GFP). GFP expression following sub-retinal injection colocalized with rhodopsin expression, indicating that photoreceptors were most effectively transduced, further, GFP expression was significantly greater than expression after intravitreal injection, which demonstrate that AAV2.5T efficiently transduces photoreceptors when injected sub-retinally, but is unable to efficiently transduce the outer retina when intravitreally injected.

FIGS. 11A-11E provide graphs showing the results of in vitro IVIg assays, which demonstrate that the indicated viruses have safe nAb profiles, similar to the parent 2.5T, as evidenced by the similarly low $IC_{50}$ values, and significantly lower than the C50 value of AAV2 (see FIG. 1B top panel). FIG. 11A show results from the 2.5T parent virus; FIG. 11B shows results from the 2.5T/7m8 (control) virus; FIG. 11C shows results from the 2.5T/7m8(÷3) Δ2 virus; FIG. 11D shows results from the 2.5T/7m8(−12) elHSPG virus; and FIG. 11E shows results from the 2.5T/7m8(−3) sHSPG virus.

FIG. 12A and FIG. 12B provide immunofluorescence images of GFP expression in gerbil retina eight weeks following intravitreal injections of AAV2.5T/7m8-12 elHSPG (also referred to as AAV2.5T/7m8(−12)−lHSPG (extra 8)) expressing GFP. In the immunofluorescence images, the cells are stained with DAPI, and also probed with antibodies to L/M Opsin (FIG. 12A), or stained with DAPI, and probed to detect parvalbumin, and rhodopsin (FIG. 12B). Fluorescence patterns that extend evenly across the transverse section are indicated in the margin of each immunofluorescence image. GFP expression colocalized with parvalbumin and DAPI staining.

FIG. 13 provides an immunofluorescence image of GFP expression in gerbil retina eight weeks following intravitreal injection of AAV2.5T/7m8-3 lHSPG expressing GFP. In the immunofluorescence image the cells are stained with DAPI, and probed to detect parvalbumin, and rhodopsin. Fluorescence patterns that extend evenly across the transverse section are indicated in the margin of each immunofluorescence image. White arrowheads indicate to points of GFP expression where expression is not uniform across a cell layer in the immunofluorescence image. GFP expression colocalized primarily with parvalbumin and DAPI.

FIG. 14A and FIG. 14B provide immunofluorescence images of GFP expression in gerbil retina eight weeks following intravitreal injection of AAV2.5T/7m8(+3)Δ2 expressing GFP. In the top immunofluorescence image (FIG. 14A), the cells are stained with DAPI, and probed to detect parvalbumin, and rhodopsin. Fluorescence patterns that extend evenly across the transverse section are indicated in the margin of each immunofluorescence image. White arrowheads indicate to points of GFP expression where expression is not uniform across a cell layer in the immunofluorescence image. IP the bottom immunofluorescence image (FIG. 14B), the cells are stained with DAPI, and probed to detect GFP and L/M opsin.

FIG. 15 provides an OTC autofluorescence image of the retina of a green monkey twelve weeks after intravitreal administration of 2.5E+12 vg/eye of AAV 2.5T/7m8(−12) elHSPG. Robust GFP expression can be observed in the macula (indicated by the black arrow) as well as inside the blood arcades (indicated by the white arrow). GFP expression FIG. 16 provides a live fluorescence image of a flat-mounted green monkey retina extracted twelve weeks following intravitreal administration of 2.5E+12 vg/eye of AAV 2.5T/7m8(−12) elHSPG. GFP expression is present in the macula, as well as within the blood arcades. Arrows indicate the location of the transverse sections depicted in FIGS. 17A-17C.

FIGS. 17A-17C provide immunofluorescence images of GFP expression in retinal cells of a cryosectioned green monkey retina twelve weeks following intravitreal administration of 2.5E+12 vg/eye of AAV 2.5T/7m8(−12) elHSPG. Sections were taken in the fovea (FIG. 17A), mid-periphery (FIG. 17B), and periphery (FIG. 17C). In FIG. 17A, a section of the fovea, the cells are stained with DAPI, and probed to detect GFP, Calbindin (bipolar cells), and S-opsin (S Cones). In FIG. 17B, a cross section of the mid-periphery of the retina, the cells are stained with DAPI, and probed to detect GFP, rhodopsin (rods), and L/M-opsin (L/M cones). In FIG. 17C, a cross section of the periphery of the retina, cells are stained with DAPI, and probed to detect GFP, glutamine synthetase (Müller cells), and L/M-opsin (L/M Cones). GFP expression is present in all three figures. GFP colocalizes with RGCs, cones, and Müller cells and is robustly expressed.

Figure 18:
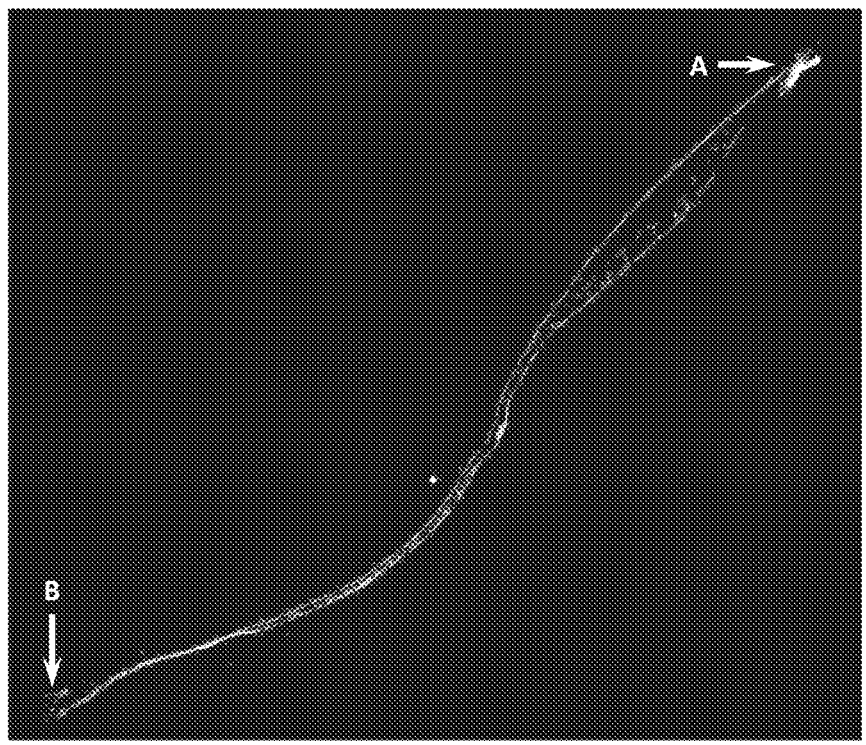

FIG. 18 provides an immunofluorescence image of GFP expression in a cross section of the temporal retinal petal of a green monkey, twelve weeks after intravitreal administration of 2.5E+12 vg/eye of AAV2.5T/7m8(−12) elHSPG. GFP expression is present from the fovea (marked A) to the ora serrata (marked B).

Figure 19:
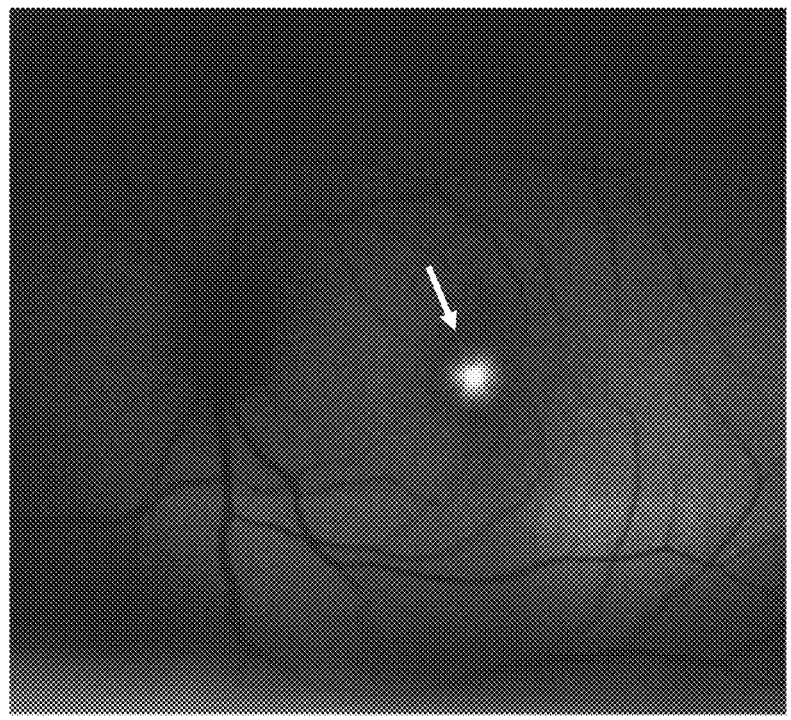

FIG. 19 provides an OTC autofluorescence image of a green monkey retina twelve weeks following intravitreal administration of 2.5E+12 vg/eye of AAV2.5T/7m8(+3)Δ2. Robust GFP expression can be observed in the macula (indicated by the white arrow).

FIG. 20 provides a live fluorescence image of a flat-mounted green monkey retina extracted twelve weeks following intravitreal administration of 2.5E+12 vg/eye of AAV2.5T/7m8(+3)Δ2. Arrow indicates the location of the transverse section depicted in FIG. 21. Expression GFP appears primarily in the macula.

FIG. 21 provides an immunofluorescence image of GFP expression in retinal cells of a cryosectioned green monkey retina twelve weeks after intravitreal administration of 2.5E+12 vg/eye of AAV2.5T/7m8(+3)Δ2. The sections was taken in the fovea. In the immunofluorescence images, the cells are stained with DAPI, and probed to detect GFP, PNA (cones), and vimentin (Müller cells). GFP expression colocalizes with vimentin in the fovea, indicating that transduction occurred primarily in this region.

DETAILED DESCRIPTION OF THE INVENTION

The present disclosure provides modified capsid proteins and virions and viral vectors having one or more modified or altered capsid protein, where in various embodiments, the virions exhibit: 1) increased infectivity of a retinal cell; 2) altered tropism; 3) increased binding to heparan or heparan sulfate proteoglycans and/or the inner limiting membrane (ILM); and/or 4) an increased ability to infect and/or deliver a therapeutic gene product across the ILM when administered intravitreally, as compared to a corresponding virion comprising its native or wild-type capsid protein instead of a modified capsid protein disclosed herein. Also provided are pharmaceutical compositions and methods for the use of any of the compositions disclosed herein for promoting the expression of a gene in cells, e.g., retinal cells, in an individual, e.g., for the treatment or prophylaxis of a disease or disorder. These and other objects, advantages, and features of the invention will become apparent to those persons skilled in the art upon reading the details of the compositions and methods as more fully described below.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "AAV" is an abbreviation for adeno-associated virus, and may be used to refer to the virus itself or derivatives thereof. The term covers all subtypes and both naturally occurring and recombinant forms, except where required otherwise. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The terms "AAV2.5T" and "2.5T" are used interchangeably, as are the terms "AAV2.5T/7m8" and "2.5T/7m8". The term "lHSPG(extra8)" and the term "elHSPG" refer to the same sequence and are used interchangeably. The term "2pt" and "Δ2" are used interchangeably, and refer to capsids containing both the S576R and T579R mutations in the AAV2.5T capsid.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077 (AAV-1), AF063497 (AAV-1), NC_001401 (AAV-2), AF043303 (AAV-2), NC_001729 (AAV-3), NC_-001829 (AAV-4), U89790 (AAV-4), NC_006152 (AAV-5), AF513851 (AAV-7), AF513852 (AAV-8), and NC_006261 (AAV-8); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73:1309; Bantel-Schaal et al. (1999) J. Virology 73:939; Xiao et al. (1999) J. Virology 73:3994; Muramatsu et al. (1996) Virology 221:208; Shade et al. (1986) J. Virol. 58:921; Gao et al. (2002) Proc. Nat. Acad. Sci. USA 99:11854; Moris et al. (2004) Virology 33:375-383; international patent publications WO 00/28061, WO 99/61601, WO 98/11244; and U.S. Pat. No. 6,156,303.

An "AAV virus" or "AAV viral particle" or "rAAV vector particle" or "rAAV particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as a "rAAV vector particle" or simply a "rAAV vector". Thus, production of rAAV particle necessarily includes production of rAAV vector, as such a vector is contained within a rAAV particle.

The term "replication defective" as used herein relative to an AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

An "AAV variant" or "AAV mutant" as used herein refers to a viral particle composed of: a) a variant AAV capsid protein, where the variant AAV capsid protein comprises at least one amino acid difference (e.g., amino acid substitution, amino acid insertion, amino acid deletion) relative to a corresponding parental AAV capsid protein, where the AAV capsid protein does not correspond to the amino acid sequence present of a naturally occurring AAV capsid protein; and, optionally, b) a heterologous nucleic acid comprising a nucleotide sequence encoding a heterologous gene product, wherein the variant AAV capsid protein confers increased binding to heparan or a heparan sulfate proteoglycan as compared to the binding by an AAV virion comprising the corresponding parental AAV capsid protein. In certain embodiments, the variant capsid protein confers: a) increased infectivity of a retinal cell compared to the infectivity of the retinal cell by an AAV virion comprising the corresponding parental AAV capsid protein; b) altered cellular tropism as compared to the tropism of an AAV virion comprising the corresponding parental AAV capsid protein; and/or c) an increased ability to bind and/or cross the ILM as compared to an AAV virion comprising the corresponding parental AAV capsid protein.

The abbreviation "rAAV" refers to recombinant adeno-associated virus, also referred to as a recombinant AAV vector (or "rAAV vector"). A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

An "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) Mol. Ther. 11:S337 (describing a TCID50 infectious titer assay); and Zolotukhin et al. (1999) Gene Ther. 6:973. See also the Examples.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0.

A "gene" refers to a polynucleotide containing at least one open reading frame that is capable of encoding a particular gene product after being transcribed, and sometimes also translated. The term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises additional, non-coding, sequence. For example, the gene may or may not include regions preceding and following the coding region, e.g. 5' untranslated (5' UTR) or "leader" sequences and 3' UTR or "trailer" sequences, as well as intervening sequences (introns) between individual coding segments (exons).

A "gene product" is a molecule resulting from expression of a particular gene. Gene products include, e.g., a polypeptide, an aptamer, an interfering RNA, an mRNA, and the like. In particular embodiments, a "gene product" is a polypeptide, peptide, protein or interfering RNA including short interfering RNA (siRNA), miRNA or small hairpin RNA (shRNA). In particular embodiments, a gene product is a therapeutic gene product, e.g., a therapeutic protein.

As used herein, a "therapeutic gene" refers to a gene that, when expressed, produces a therapeutic gene product that confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include, but are not limited to, genes that correct a genetic deficiency in a cell or mammal.

As used herein, a "transgene" is a gene that is delivered to a cell by a vector.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a gene product of interest, and is used for effecting the expression of the gene product in an intended target cell. An expression vector also comprises control elements operatively linked to the encoding region to facilitate expression of the gene product in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

As used herein, the terms "polypeptide," "peptide," and "protein" refer to polymers of amino acids of any length. The terms also encompass an amino acid polymer that has been modified; for example, disulfide bond formation, glycosylation, lipidation, phosphorylation, or conjugation with a labeling component.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter, and a polyadenylation sequence consists only of the promoter, polynucleotide sequence encoding the therapeutic polypeptide, and polyadenlyation sequence. As another example, a polypeptide "consisting of" a recited sequence contains only the recited sequence.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

An "enhancer" as used herein encompasses a cis-acting element that stimulates or inhibits transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "termination signal sequence" as used herein encompasses any genetic element that causes RNA polymerase to terminate transcription, such as for example a polyadenylation signal sequence.

A "polyadenylation signal sequence" as used herein encompasses a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, the terms "operatively linked" or "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained. As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wildtype virus or cell. The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an "immunoglobulin", "antibody" or fragment or variant thereof refers to the ability to bind an antigenic determinant and thereby facilitate immunological function. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g. promoter, enhancer, kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing", as used herein, refer to delivery of a vector for recombinant gene or protein expression to a cell, to cells and/or organs of a subject, or to a subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected"; "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

Unless otherwise indicated, all terms used herein have the same meaning as they would to one skilled in the art and the practice of the present invention will employ, conventional techniques of microbiology and recombinant DNA technology, which are within the knowledge of those of skill of the art.

Variant AAV Capsid Polypeptides

The present disclosure provides variant AAV capsid proteins, where the variant AAV capsid protein comprises one or more amino acid modifications as compared to the wild-type AAV or a corresponding parental AAV. In particular embodiments, the variant AAV capsid protein comprises one or more amino acid modifications as compared to a capsid protein of AAV2.5T, AAV7m8, or AAV2.5T/7m8. In particular embodiments, the variant AAV capsid protein comprises one or more amino acid modifications as compared to a capsid protein having at least 90%, at least 95%, at least 98%, or at least 99% sequence identity to an AAV2.5T, AAV7m8, or AAV2.5T/7m8 capsid protein. In particular embodiments, the variant AAV capsid protein comprises one or more amino acid modifications as compared to a capsid protein of AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, or ovine AAV. In particular embodiments, the variant AAV capsid protein comprises one or more amino acid modifications as compared to a capsid protein having at least 90%, at least 95%, at least 98%, or at least 99% sequence identity to a capsid protein of AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, or ovine AAV. While reference is made herein to amino acid modifications of capsid proteins (including specific amino acid substitutions and insertions) using the amino acid numbering corresponding to AAV2 or AAV2.5T capsid protein, it is understood that any of these amino acid modifications may also be introduced in the capsid protein of AAVs of other serotypes, e.g., at positions corresponding to those of AAV2 or AAV2.5T. FIG. 10 provides an alignment of amino acids corresponding to 570-610 of AAV2 for various AAV serotypes. These sequences share significant homology and similar amino acid numbering, and the skilled artisan can readily determine amino acid residues in other AAV serotypes that correspond to those specifically described herein for AAV2 or AAV2.5T.

In particular embodiments, the variant capsid protein, when present in an AAV virion, confers increased infectivity of a retinal cell as compared to the infectivity of the retinal cell by an AAV virion comprising the corresponding parental AAV capsid protein. In some cases, the retinal cell is a photoreceptor cell (e.g., rods; cones). In other cases, the retinal cell is an RGC. In other cases, the retinal cell is an RPE cell. In other cases, the retinal cell is a Müller cell. Other retinal cells include amacrine cells, bipolar cells, and horizontal cells. In particular embodiments, the variant capsid protein, when present in an AAV virion, confers altered tropism as compared to the tropism of the retinal cell by an AAV virion comprising the corresponding parental AAV capsid protein. In particular embodiments, the variant capsid protein, when present in an AAV virion, confers increased binding to heparan or heparan sulfate, and/or increased ability to bind and cross the inner limiting membrane following intravitreal injection, as compared to an AAV virion comprising the corresponding parental AAV capsid protein.

In certain embodiments, the parental AAV capsid protein is an AAV2.5T capsid protein, or a variant thereof having at least 90%, at least 95%, at least 98%, at least 99% sequence identity to an AAV2.5T capsid protein. AAV2.5T capsid proteins and virions are described in U.S. Pat. No. 9,233,131, in which the VP1-encoding amino acid sequences of AAV2.5T is provided as SEQ ID NO:42 and FIGS. 10A-B. An AAV2.5T VP-1 amino acid sequence is also provided herein as SEQ ID NO:41.

In certain embodiments, the parental AAV capsid protein is an AAV7m8 capsid protein, or a variant thereof having at least 90%, at least 95%, at least 98%, at least 99% sequence identity to an AAV7m8 capsid protein. AAV7m8 capsid proteins are described in U.S. Pat. No. 9,193,956. AAV7m8 includes an at least five amino acid insert (the "7m8 insert") within the capsid protein of AAV2, located between amino acids 587 and 588 of the wildtype AAV2 genome. In certain embodiment, the 7m8 amino acid insert comprises or consists of the following amino acid sequence: LGETTRP (SEQ ID NO:11). In particular embodiments, the 7m8 insert comprises or consists of the amino acid sequence: LALGETTRPA (SEQ ID NO:4), or a fragment comprising at least five, at least six, at least seven, at least eight, or at least nine consecutive amino acids thereof. In particular embodiments, the 7m8 insert comprises or consists of an amino acid sequence having at least 80%, at least 85%, or at least 90% homology to the amino acid sequence: LALGETTRPA (SEQ ID NO:4), or a fragment comprising at least five, at least six, at least seven, at least eight, or at least nine consecutive amino acids thereof. In one embodiment, the parental AAV capsid protein is an AAV2/7m8 capsid protein comprising or consisting of the following amino acid sequence:

(SEQ ID NO: 28)
MAADGYLPDWLEDTLSEGIRQWWKLKPGPPPPKPAERHKDDSRGLVLPG

YKYLGPFNGLDKGEPVNEADAAALEHDKAYDRQLDSGDNPYLKYNHADA

EFQERLKEDTSFGGNLGRAVFQAKKRVLEPLGLVEEPVKTAPGKKRPVE

HSPVEPDSSSGTGKAGQQPARKRLNFGQTGDADSVPDPQPLGQPPAAPS

GLGTNTMATGSGAPMADNNEGADGVGNSSGNWHCDSTWMGDRVITTSTR

TWALPTYNNHLYKQISSQSGASNDNHYFGYSTPWGYFDFNRFHCHFSPR

DWQRLINNNWGFRPKRLNFKLFNIQVKEVTQNDGTTTIANNLTSTVQVF

TDSEYQLPYVLGSAHQGCLPPFPADVFMVPQYGYLTLNNGSQAVGRSSF

YCLEYFPSQMLRTGNNFTFSYTFEDVPFHSSYAHSQSLDRLMNPLIDQY

LYYLSRTNTPSGTTTQSRLQFSQAGASDIRDQSRNWLPGPCYRQQRVSK

TSADNNNSEYSWTGATKYHLNGRDSLVNPGPAMASHKDDEEKFFPQSGV

LIFGKQGSEKTNVDIEKVMITDEEEIRTTNPVATEQYGSVSTNLQRGNL

ALGETTRPARQAATADVNTQGVLPGMVWQDRDVYLQGPIWAKIPHTDGH

FHPSPLMGGFGLKHPPPQILIKNTPVPANPSTTFSAAKFASFITQYSTG

QVSVEIEWELQKENSKRWNPEIQYTSNYNKSVNVDFTVDTNGVYSEPRP

IGTRYLTRNL, or a variant thereof having at least 90%, at least 95%, at least 98%, or at least 99% sequence identity to SEQ ID NO:28.

In certain embodiments, the parental capsid protein is an AAV2.5T/7m8 capsid protein, or a variant having at least 90%, at least 95%, at least 98%, at least 99% sequence identity to an AAV2.5T/7m8 capsid protein. AAV2.5T/7m8 capsid proteins correspond to AAV2.5T capsid proteins further comprising a 7m8 insert. In certain embodiment, the 7m8 amino acid insert comprises or consists of the following amino acid sequence: LGETTRP (SEQ ID NO:11). In particular embodiments, the 7m8 insert comprises or consists of the amino acid sequence: LALGETTRPA (SEQ ID NO:4), or a fragment comprising at least five, at least six, at least seven, at least eight, or at least nine consecutive amino acids thereof. In particular embodiments, the 7m8 insert comprises or consists of an amino acid sequence having at least 80%, at least 85%, or at least 90% homology to the amino acid sequence: LALGETTRPA (SEQ ID NO:4), or a fragment comprising at least five, at least six, at least seven, at least eight, or at least nine consecutive amino acids thereof. The 7m8 insert may be inserted at various sites within the AAV2.5T capsid protein. For example, it may be inserted between amino acid residues 587 and 588 of AAV2.5T as shown in FIG. 3B. Alternatively, it may be inserted either upstream or downstream, including, e.g., between any of: amino acid residues 574 and 575 (−12); amino acid residues 575 and 576 (−9); amino acid residues 576 and 577 (−6); amino acid residues 577 and 578 (−3); amino acid residues 578 and 579 (0); amino acid residues 579 and 580 (+3), as shown in FIGS. 3B and 3C. In addition, it may be inserted at other locations, including, e.g., between any of amino acid residues 571-585 of AAV2.5T.

In particular embodiments, the 7m8 insertion site is in the GH loop, or loop IV, of the AAV capsid protein, e.g., in a solvent-accessible portion of the GH loop, or loop IV, of the AAV capsid protein, such as AAV2.5T. For the GH loop/ loop IV of AAV capsid, see, e.g., van Vliet et al. (2006) Mol. Ther. 14:809; Padron et al. (2005) J. Virol. 79:5047; and Shen et al. (2007) Mol. Ther. 15:1955. For example, the insertion site can be within amino acids 411-650 of an AAV capsid protein. For example, the insertion site can be within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV8, within amino acids 571 to 612 of AAV9, or within amino acids 573 to 614 of AAV10.

In some embodiments, the insertion site is a single insertion site between two adjacent amino acids located between amino acids 570-614 of VP1 of any AAV serotype, e.g., the insertion site is between two adjacent amino acids located in amino acids 570-610, amino acids 580-600, amino acids 570-575, amino acids 575-580, amino acids 580-585, amino acids 585-590, amino acids 590-600, or amino acids 600-614, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600. For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10. As another example, the insertion site can be between amino acids 450 and 460 of an AAV capsid protein. For example, the insertion site can be at (e.g., immediately N-terminal to) amino acid 453 of AAV2, at amino acid 454 of AAV1, at amino acid 454 of AAV6, at amino acid 456 of AAV7, at amino acid 456 of AAV8, at amino acid 454 of AAV9, or at amino acid 456 of AAV10. In particular embodiments of AAV2.5T/7m8 capsid proteins disclosed herein, the 7m8 insert is present between the amino acid residues in AAV2.5T corresponding to any of those described herein for other AAV, such as AAV2.

In some embodiments, a capsid protein includes an 7m8 insertion comprising an amino acid sequence having at least about 85%, at least about 90%, at least about 95%, at least about 98%, at least about 99%, or 100%, amino acid sequence identity to an amino acid sequence selected from LGETTRP (SEQ ID NO:11) and LALGETTRPA (SEQ ID NO:4).

In various embodiments, modified capsid proteins disclosed herein comprise one or more amino acid modifications as compared to a capsid protein of an AAV, e.g., AAV2.5T, AAV7m8, AAV2.5T/7m8, or AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, or ovine AAV, optionally each also comprising a 7m8 insert. In certain embodiments, the one or more amino acid modification result in the modified capsid protein being capable of binding heparan or heparan sulfate proteoglycan, and certain of such variants may be referred to herein as AAV2.5T HSPG variants, AAV7m8 HSPG variants, or AAV2.5/7m8 HSPG variants, respectively.

In particular embodiments, the one or more amino acid modifications comprise introducing a heparan binding sequence of AAV2 into AAV2.5T, AAV7m8 or AAV2.5T/7m8, or any of the other AAV serotypes described herein, alone or in combination with a 7m8 insertion. In particular embodiments, the one or more amino acid modifications include one or more amino acid substitutions or insertions. In particular embodiments, variant capsid proteins disclosed herein comprise one or more amino acid substitutions corresponding to S576R or T579R when using the amino acid numbering shown in FIGS. 3A-3C for AAV2.5T.

In other embodiments, variant capsid proteins disclosed herein comprise an amino acid insertion comprising four or more, five or more, or all six consecutive amino acids within the sequence: RGNRQA (SEQ ID NO:5). In particular embodiments, the insertion comprises four or more, five or more, six or more, or all seven consecutive amino acids within the sequence: QRGNRQA (SEQ ID NO:12). In particular embodiments, the insertion comprises four or more, five or more, six or more, seven or more, eight or more, nine or more, ten or more, or all eleven consecutive amino acids within the sequence: NLQRGNRQAATA (SEQ ID NO:7) or the sequence: NLQRGNRQAATAAP (SEQ ID NO:8). In certain embodiments, the insertion comprises or consists of an amino acid sequence having at least 80%, at least 85%, or at least 90% homology to four or more, five or more, six or more, seven or more, eight or more, nine or more, ten or more, or all eleven consecutive amino acids within the sequence: NLQRGNRQAATA (SEQ ID NO:7) or NLQRGNRQAATAAP (SEQ ID NO:8). In certain embodiments, the insertion is located upstream or downstream of the 7m8 insertion. In certain embodiments, the insertion is divided, such that one or more amino acids of the insertion are located upstream of the 7m8 insertion, and one or more amino acids of the insertion are located downstream of the 7m8 insertion (see, e.g., FIGS. 3A-3C). Accordingly, in particular embodiments, a modified AAV capsid protein, e.g., a modified AAV2.5T/7m8 capsid protein, disclosed herein comprises one or more of the following amino acid sequences, wherein the underlined sequence corresponds to a 7m8 loop insert sequence, and the non-underlined sequence corresponds to the "swap residues" amino acid sequence:

NLQRGNRQAATA<u>LALGETTRPA</u>; (SEQ ID NO: 13)

NLQRGNRQAAT<u>LALGETTRPA</u>A; (SEQ ID NO: 14)

NLQRGNRQAA<u>LALGETTRPA</u>TA; (SEQ ID NO: 15)

NLQRGNRQA<u>LALGETTRPA</u>ATA; (SEQ ID NO: 16)

NLQRGNRQ<u>LALGETTRPA</u>AATA; (SEQ ID NO: 17)

NLQRGNR<u>LALGETTRPA</u>QAATA; (SEQ ID NO: 18)

NLQRGN<u>LALGETTRPA</u>RQAATA; (SEQ ID NO: 19)

NLQRG<u>LALGETTRPA</u>NRQAATA; (SEQ ID NO: 20)

NLQR<u>LALGETTRPA</u>GNRQAATA; (SEQ ID NO: 21)

NLQ<u>LALGETTRPA</u>RGNRQAATA; (SEQ ID NO: 22)

NL<u>LALGETTRPA</u>QRGNRQAATA; (SEQ ID NO: 23)

N<u>LALGETTRPA</u>LQRGNRQAATA; (SEQ ID NO: 24)
or

<u>LALGETTRPA</u>NLQRGNRQAATA. (SEQ ID NO: 25)

In certain aspects, the modified AAV2.5T capsid protein comprises at least one of the one or more of the following amino acid modifications: a S576R point mutation; a T579R point mutation; a substitution of amino acid residues 576-579 or amino acid residues 576-581 with the following amino acid residues: RGNRQA (SEQ ID NO:5); a substitution of amino acid residues 576-581 with the following amino acid residues: RGNRQAAP (SEQ ID NO:6); a substitution of amino acid residues 573-581 or amino acid residues 573-584 with the following amino acid residues: NLQRGNRQAATA (SEQ ID NO:7); or a substitution of amino acid amino acid residues 573-581 or amino acid residues 573-584 with the following amino acid residues: NLQRGNRQAATAAP (SEQ ID NO:8). In particular embodiments, it comprises both a S576R point mutation and a T579R point mutation.

In particular aspects, the modified AAV2.5T/7m8 capsid protein comprises at least one of the one or more of the following amino acid modifications: a point mutation corresponding to a S576R point mutation in AAV2.5T; a point mutation corresponding to a T579R point mutation in AAV2.5T; a substitution corresponding to a substitution of amino acid residues 576-579 or amino acid residues 576-581 in AAV2.5T with the following amino acid residues: RGNRQA (SEQ ID NO:5); a substitution corresponding to a substitution of amino acid residues 576-579 or amino acid residues 576-581 in AAV2.5T with the amino acid residues: RGNRQAAP (SEQ ID NO:6) or NLQRGNRQAATA (SEQ ID NO:7); a substitution corresponding to a substitution of amino acid residues 573-579, amino acid residues 573-581, amino acid residues 573-583, or amino acid residues 573-584 in AAV2.5T with the following amino acid residues: NLQRGNRQAATA (SEQ ID NO:7); or a substitution corresponding to a substitution of amino acid residues 573-579, amino acid residues 573-581, amino acid residues 573-583, amino acid residues 573-584, or amino acid residues 576-583 in AAV2.5T with the following amino acid residues: NLQRGNRQAATAAP (SEQ ID NO:8). In particular embodiments, it comprises both a point mutation corresponding to a S576R point mutation in AAV2.5T and a point mutation corresponding to a T579R point mutation in AAV2.5T. As described herein, an AAV2.5T/7m8 capsid protein corresponds to an AAV2.5T capsid protein with an insertion of a 7m8 insertion sequence. Therefore, for convenience, modifications (e.g., amino acid substitutions or insertions) in AAV2.5T/7m8 are referred to as modifications "corresponding to" modifications in AAV2.5T, and the amino acid positions of modifications to AAV2.5T/7m8 are described by reference to the numbering of the corresponding amino acid position of AAV2.5T. The corresponding amino acid positions between AAV2.5T and AAV2.5T/7m8 can be readily determined by comparing the sequences of the capsid proteins and taking into account the presence of the 7m8 insertion in the AAV2.5T/7m8. Therefore, it is understood that the actual amino acid position number of a modification in AAV2.5T/7m8 may be different than the corresponding amino acid position number of a corresponding modification in AAV2.5T.

In certain embodiments, the modified AAV2.5T/7m8 capsid is present in a AAAV2.5T/7m8(+3), AAV2.5T/7m8 (0), AAV2.5T/7m8(-3), or AAV2.5T/7m8(-12) backbone.

In particular embodiments, the modified AAV capsid comprises an amino acid sequence depicted in FIGS. 3A-3C or FIGS. 4A-4C. In particular embodiments, the modified AAV capsid comprises an amino acid sequence corresponding to any other AAV serotype having a modification corresponding to any of those depicted in FIGS. 3A-3C or FIGS. 4A-4C.

In certain embodiments, the variant AAV capsid protein is an AAV2.5T T579R capsid protein comprising or consisting of the following amino acid sequence:

(SEQ ID NO: 29)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNNQSSTRAPTTGTYNL
QEIVPGSVWMERDVYLQGPIWAKIPETGAHFHPSPAMGGFGLKHPPPMM
LIKNTPVPGNITSFSDVPVSSFITQYSTGQVTVEMEWELKKENSKRWNP
EIQYTNNYNDPQFVDFAPDSTGEYRTTRPIGTRYLTRPL, or a variant thereof having at least 90%, at least 95%, at least 98%, or at least 99% sequence identity to SEQ ID NO:29.

In certain embodiments, the variant AAV capsid protein is an AAV2.5T-2pt capsid protein comprising or consisting of the following amino acid sequence:

(SEQ ID NO: 30)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNNQRSTRAPTTGTYNL
QEIVPGSVWMERDVYLQGPIWAKIPETGAHFHPSPAMGGFGLKHPPPMM
LIKNTPVPGNITSFSDVPVSSFITQYSTGQVTVEMEWELKKENSKRWNP
EIQYTNNYNDPQFVDFAPDSTGEYRTTRPIGTRYLTRPL, or a variant thereof having at least 90%, at least 95%, at least 98%, or at least 99% sequence identity to SEQ ID NO:30.

In certain embodiments, the variant AAV capsid protein is an AAV2.5T-sHSPG(correct) capsid protein comprising or consisting of the following amino acid sequence:

(SEQ ID NO: 31)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNNQRGNRQATTGTYNL
QEIVPGSVWMERDVYLQGPIWAKIPETGAHFHPSPAMGGFGLKHPPPMM
LIKNTPVPGNITSFSDVPVSSFITQYSTGQVTVEMEWELKKENSKRWNP
EIQYTNNYNDPQFVDFAPDSTGEYRTTRPIGTRYLTRPL, or a variant thereof having at least 90%, at least 95%, at least 98%, or at least 99% sequence identity to SEQ ID NO:31.

In certain embodiments, the variant AAV capsid protein is an AAV2.5T-lHSPG(correct) capsid protein comprising or consisting of the following amino acid sequence:

(SEQ ID NO: 32)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS

-continued

TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNLQRGNRQAATATYNL
QEIVPGSVWMERDVYLQGPIWAKIPETGAHFHPSPAMGGFGLKHPPPMM
LIKNTPVPGNITSFSDVPVSSFITQYSTGQVTVEMEWELKKENSKRWNP
EIQYTNNYNDPQFVDFAPDSTGEYRTTRPIGTRYLTRPL, or a variant thereof having at least 90%, at least 95%, at least 98%, or at least 99% sequence identity to SEQ ID NO:32.

In certain embodiments, the variant AAV capsid protein is an AAV2.5T/7m8(0)-sHSPG(correct) capsid protein comprising or consisting of the following amino acid sequence:

(SEQ ID NO: 33)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNNQRGLALGETTRPAN
RQATTGTYNLQEIVPGSVWMERDVYLQGPIWAKIPETGAHFHPSPAMGG
FGLKHPPPMMLIKNTPVPGNITSFSDVPVSSFITQYSTGQVTVEMEWEL
KKENSKRWNPEIQYTNNYNDPQFVDFAPDSTGEYRTTRPIGTRYLTRPL, or a variant thereof having at least 90%, at least 95%, at least 98%, or at least 99% sequence identity to SEQ ID NO:33.

In certain embodiments, the variant AAV capsid protein is an AAV2.5T/7m8(0)-lHSPG(correct) capsid protein comprising or consisting of the following amino acid sequence:

(SEQ ID NO: 34)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNLQRGNLALGETTRPA
RQAATATYNLQEIVPGSVWMERDVYLQGPIWAKIPETGAHFHPSPAMGG
FGLKHPPPMMLIKNTPVPGNITSFSDVPVSSFITQYSTGQVTVEMEWEL
KKENSKRWNPEIQYTNNYNDPQFVDFAPDSTGEYRTTRPIGTRYLTRPL, or a variant thereof having at least 90%, at least 95%, at least 98%, or at least 99% sequence identity to SEQ ID NO:34.

In certain embodiments, the variant AAV capsid protein is an AAV2.5T/7m8(−12)-sHSPG(extra2) capsid protein comprising or consisting of the following amino acid sequence:

(SEQ ID NO: 35)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF
ATTNRMELEGASYQVPPQPNGMTNNLQGSNTYALENTMIFNSQPANPGT
TATYLEGNMLITSESETQPVNRVAYNVGGQMATNNLALGETTRPAQRGN
RQAAPTTGTYNLQEIVPGSVWMERDVYLQGPIWAKIPETGAHFHPSPAM
GGFGLKHPPPMMLIKNTPVPGNITSFSDVPVSSFITQYSTGQVTVEMEW
ELKKENSKRWNPEIQYTNNYNDPQFVDFAPDSTGEYRTTRPIGTRYLTR
PL, or a variant thereof having at least 90%, at least 95%, at least 98%, or at least 99% sequence identity to SEQ ID NO:35.

In certain embodiments, the variant AAV capsid protein is an AAV2.5T/7m8(+3)-2pt capsid protein comprising or consisting of the following amino acid sequence:

(SEQ ID NO: 1)
MAADGYLPDWLEDTLSEGIRQWWKLKPGPPPPKPAERHKDDSRGLVLPG
YKYLGPFNGLDKGEPVNEADAAALEHDKAYDRQLDSGDNPYLKYNHADA
EFQERLKEDTSFGGNLGRAVFQAKKRVLEPFGLVEEGAKTAPTGKRIDD
HFPKRKKARTEEDSKPSTSSDAEAGPSGSQQLQIPAQPASSLGADTMSA
GGGGPLGDNNQGADGVGNASGDWHCDSTWMGDRVVTKSTRTWVLPSYNN
HQYREIKSGSVDGSNANAYFGYSTPWGYFDFNRFHSHWSPRDWQRLINN
YWGFRPRSLRVKIFNIQVKEVTVQDSTTTIANNLTSTVQVFTDDDYQLP
YVVGNGTEGCLPAFPPQVFTLPQYGYATLNRDNTENPTERSSFFCLEYF
PSKMLRTGNNFEFTYNFEEVPFHSSFAPSQNLFKLANPLVDQYLYRFVS
TNNTGGVQFNKNLAGRYANTYKNWFPGPMGRTQGWNLGSGVNRASVSAF

```
ATTNRMELEGASYQVPPQPNGMTNNLQGSNTYALENTMIFNSQPANPGT

TATYLEGNMLITSESETQPVNRVAYNVGGQMATNNQRSTRLALGETTRP

AAPTTGTYNLQEIVPGSVWMERDVYLQGPIWAKIPETGAHFHPSPAMGG

FGLKHPPPMMLIKNTPVPGNITSFSDVPVSSFITQYSTGQVTVEMEWEL

KKENSKRWNPEIQYTNNYNDPQFVDFAPDSTGEYRTTRPIGTRYLTRPL,
``` or a variant thereof having at least 90%, at least 95%, at least 98%, or at least 99% sequence identity to SEQ ID NO:1.

In particular embodiments, the modified capsid protein is not disclosed in U.S. Pat. Nos. 9,441,244, 9,233,131, U.S. 200160017295, U.S. Pat. No. 7,220,577, WO 2015/168666, U.S. Pat. Nos. 7,867,484, 8,802,080, U.S. 20150005369, U.S. Pat. No. 7,172,893, WO 2015/134643, U.S. Pat. Nos. 6,962,815, 7,749,492, U.S. 20160040137, U.S. 20090317417, U.S. 20140336245, U.S. Pat. No. 7,629,322, WO 2016/133917, WO 2015/121501, U.S. Pat. Nos. 9,409,953, 8,889,641, or U.S. 20150152142.

The present disclosure also includes polynucleotides that encode one or more variant capsids described herein. In particular embodiments, the polynucleotide is an expression vector, and the expression vector comprises a polynucleotide sequence encoding a variant capsid described herein operably linked to a promoter sequence, e.g., a promoter sequence that drives expression of the polynucleotide in a cell.

The present disclosure also includes cells comprising a polynucleotide or vector that encodes a variant capsid described herein. In particular embodiments, the polynucleotide is an expression vector, and the expression vector comprises a polynucleotide sequence encoding a variant capsid described herein operably linked to a promoter sequence, e.g., a promoter sequence that drives expression of the polynucleotide in the cell. In certain embodiments, the polynucleotide or vector further comprises a sequence that encodes a rep protein, e.g., an AAV2 rep protein. In certain embodiments, the cell is a helper cell or host cell, such as, e.g., an HEK293 cell that may be used to produce virions comprising the variant capsid protein. In preparing the subject rAAV compositions, any host cells for producing rAAV virions may be employed, including, for example, mammalian cells (e.g. 293 cells), insect cells (e.g. SF9 cells), microorganisms and yeast. Host cells can also be packaging cells in which the AAV rep and cap genes are stably maintained in the host cell or producer cells in which the AAV vector genome is stably maintained and packaged. Exemplary packaging and producer cells are derived from SF-9, 293, A549 or HeLa cells. AAV vectors are purified and formulated using standard techniques known in the art.

Recombinant Virions and Viral Vectors

The present invention includes recombinant viruses or virions, e.g., gene delivery vectors or gene therapy vectors, that comprise a variant capsid protein of the present disclosure.

In certain embodiments, the virus or virion is a viral vector derived from a virus, e.g., an adenovirus, an adeno-associated virus (AAV), a lentivirus, a herpes virus, an alpha virus or a retrovirus, e.g., Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) or lentivirus. While embodiments encompassing the use of adeno-associated virus are described in greater detail below, it is expected that the ordinarily skilled artisan will appreciate that similar knowledge and skill in the art can be brought to bear on non-AAV gene therapy vectors as well. See, for example, the discussion of retroviral vectors in, e.g., U.S. Pat. Nos. 7,585,676 and 8,900,858, and the discussion of adenoviral vectors in, e.g. U.S. Pat. No. 7,858,367, the full disclosures of which are incorporated herein by reference. In certain embodiments, the recombinant virus or virion is infectious. In certain embodiments, the recombinant virion or virus is replication-competent. In certain embodiments, the recombinant virus or virion is replication-incompetent. In particular embodiments, the virion is an AAV2.5T, an AAV7m8 or an AAV2.5T/7m8 comprising a modified capsid protein described herein.

In some embodiments, the recombinant virion or virus, e.g., an AAV, further comprises a polynucleotide cassette comprising a sequence that encodes a gene product, e.g., a therapeutic gene product. In certain embodiments, the polynucleotide cassette is flanked on the 5' and 3' ends by functional AAV inverted terminal repeat (ITR) sequences. By "functional AAV ITR sequences" is meant that the ITR sequences function as intended for the rescue, replication and packaging of the AAV virion. Hence, AAV ITRs for use in the gene delivery vectors of the invention need not have a wild-type nucleotide sequence, and may be altered by the insertion, deletion or substitution of nucleotides or the AAV ITRs may be derived from any of several AAV serotypes, e.g. AAV1, AAV2, AAV3, AAV4, AAV5, AAV6, AAV7, AAV8, AAV9, AAV10. Preferred AAV vectors have the wild type REP and CAP genes deleted in whole or part, but retain functional flanking ITR sequences.

Recombinant viral vectors (e.g., rAAV virions) comprising variant capsid proteins described herein, and optionally encapsulating polynucleotide cassettes of the present disclosure, may be produced using standard methodology. For example, in the case of rAAV virions, an AAV expression vector comprising a polynucleotide cassette may be introduced into a producer cell, followed by introduction of an AAV helper construct comprising a polynucleotide sequence encoding a variant capsid protein disclosed herein, and where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions comprising variant capsid proteins described herein are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

As disclosed in the accompanying Example, variant capsid proteins described herein confer enhanced or altered cellular tropism to virions comprising the variant capsid proteins. Accordingly, the variant capsids may be used to enhance or alter the tropism of a virus or virion in order to enhance its tropism for a desired cell type.

In particular embodiments, the virions or viral vectors comprising a variant capsid protein described herein bind to heparan or heparan sulfate proteoglycans (HSPGs), e.g., with an affinity at least 2-fold, at least 3-fold, at least 4-fold, at least 5-fold, at least 10-fold, at least 20-fold, at least 50-fold, or at least 100-fold as compared to a corresponding virion or viral vector that does not include a variant capsid protein disclosed herein.

In particular embodiments, the virions or viral vectors comprising a variant capsid protein described herein bind to ILM, e.g., with an affinity at least 2-fold, at least 3-fold, at least 4-fold, at least 5-fold, at least 10-fold, at least 20-fold, at least 50-fold, or at least 100-fold as compared to a corresponding virion or viral vector that does not include a variant capsid protein disclosed herein.

In particular embodiments, the virions or viral vectors comprising a variant capsid protein described herein are capable of delivering a gene product to the retina when delivered via intravitreal injection, e.g., wherein they result in the expression of at least 2-fold, at least 3-fold, at least 4-fold, at least 5-fold, at least 10-fold, at least 20-fold, at least 50-fold, or at least 100-fold gene product as compared to a corresponding virion or viral vector that does not include a variant capsid protein disclosed herein.

In certain embodiments, the virions or viral vectors bind heparan or heparan sulfate with a binding affinity such that they are eluted from a heparan column at a salt concentration of about 0.2 M to about 0.4 M, e.g., as described in the accompanying Examples.

Pharmaceutical Compositions

Pharmaceutical compositions comprising a virion or viral vector comprising a variant capsid protein described herein and one or more pharmaceutically acceptable diluent, carrier, or excipient are also disclosed. The subject virions or vector can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile. For instances in which ocular cells are to be contacted in vivo, the subject polynucleotide cassettes or gene delivery vectors comprising the subject polynucleotide cassette can be treated as appropriate for delivery to the eye.

Pharmaceutical compositions may further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the vector or virion in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the pharmaceutical compositions are prepared with carriers that will protect the virion or vector against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It may be advantageous to formulate oral, ocular or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Any concentration of viral particles suitable to effectively transducer mammalian cells can be prepared. For example, the viral particles may be formulated at a concentration of $10^8$ vector genomes per ml or more, for example, $5 \times 10^8$ vector genomes per mL; $10^9$ vector genomes per mL; $5 \times 10^9$ vector genomes per mL, $10^{10}$ vector genomes per mL, $5\times10^{10}$ vector genomes per mL; $10^{11}$ vector genomes per mL; $5\times10^{11}$ vector genomes per mL; $10^{12}$ vector genomes per mL; $5\times10^{12}$ vector genomes per mL; $10^{13}$ vector genomes per mL; $1.5\times10^{13}$ vector genomes per mL; $3\times10^{13}$ vector genomes per mL; $5\times10^{13}$ vector genomes per mL; $7.5\times10^{13}$ vector genomes per mL; $9\times10^{13}$ vector genomes per mL; $1\times10^{14}$ vector genomes per mL, $5\times10^{14}$ vector genomes per mL or more, but typically not more than $1\times10^{15}$ vector genomes per mL.

The subject viral vector may be formulated into any suitable unit dosage, including, without limitation, $1\times10^{8}$ vector genomes or more, for example, $1\times10^{9}$, $1\times10^{10}$, $1\times10^{11}$, $1\times10^{12}$, or $1\times10^{13}$ vector genomes or more, in certain instances, $1\times10^{14}$ vector genomes, but usually no more than $4\times10^{15}$ vector genomes. In some cases, the unit dosage is at most about $5\times10^{15}$ vector genomes, e.g. $1\times10^{14}$ vector genomes or less, for example $1\times10^{13}$, $1\times10^{12}$, $1\times10^{11}$, $1\times10^{19}$, or $1\times10^{9}$ vector genomes or less, in certain instances $1\times10^{8}$ vector genomes or less, and typically no less than $1\times10^{8}$ vector genomes. In some cases, the unit dosage is $1\times10^{10}$ to $1\times10^{"}$ vector genomes. In some cases, the unit dosage is $1\times10^{10}$ to $3\times10^{12}$ vector genomes. In some cases, the unit dosage is $1\times10^{9}$ to $3\times10^{13}$ vector genomes. In some cases, the unit dosage is $1\times10^{8}$ to $3\times10^{14}$ vector genomes.

In some cases, the unit dosage of a pharmaceutical composition may be measured using multiplicity of infection (MOI). By MOI it is meant the ratio, or multiple, of vector or viral genomes to the cells to which the nucleic acid may be delivered. In some cases, the MOI may be $1\times10^{6}$. In some cases, the MOI may be $1\times10^{5}$-$1\times10^{7}$. In some cases, the MOI may be $1\times10^{4}$-$1\times10^{8}$. In some cases, recombinant viruses of the disclosure are at least about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^{8}$ to $3\times10^{14}$ MOI. In some cases, recombinant viruses of the disclosure are at most about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$, $1\times10^{16}$, $1\times10^{17}$ and $1\times10^{18}$ MOI.

In some aspects, the amount of pharmaceutical composition comprises about $1\times10^{8}$ to about $1\times10^{15}$ recombinant viruses, about $1\times10^{9}$ to about $1\times10^{14}$ recombinant viruses, about $1\times10^{10}$ to about $1\times10^{13}$ recombinant viruses, or about $1\times10^{11}$ to about $3\times10^{12}$ recombinant viruses.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active metabolite or residue thereof.

The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The subject polynucleotide cassette or gene delivery vector, e.g., recombinant virus (virions), can be incorporated into pharmaceutical compositions for administration to mammalian patients, particularly primates and more particularly humans. The subject polynucleotide cassette or gene delivery vector, e.g. virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

Method of Enhancing or Altering Viral Tropism

As disclosed in the accompanying Examples, variant capsid proteins described herein confer enhanced or altered cellular tropism to virions comprising the variant capsid proteins. For example, certain variant capsid proteins described herein are associated with increased infectivity of the retina or increased expression levels of gene product in the retina, increased binding to the ILM, increased infectivity of the retina following intravitreal injection or increased expression of gene product in the retina following intravitreal injection, and/or increased infectivity of or increased expression of gene products in particular ocular cells, such as, e.g., retinal cells, RGC or Müller cells.

Examples of retinal cell components that may be transfected by vectors of the instant invention can include, but are not limited to, astrocytes, Müller Cells, RGC, RGC axons, photoreceptors, bipolar cells, amacrine cells, horizontal cells and combinations thereof. In some instances, cell markers are used to measure transduction of a transgene into a retinal cell component. Cell markers can include, but are not limited to, GFAP, Vimetin, Fox, β-tubulin, rhodopsin, PKCa, parvalbumin, calbinding and combinations thereof. Table 1 below depicts each cell marker with the corresponding retinal cell component.

TABLE 1

Summary of cell markers and cell types

| Marker | Cell Type |
| --- | --- |
| GFAP | Astrocytes |
| Vimentin | Müller Cells |
| Fox | RGC |
| B-tubulin | RGC axons |
| Rhodopsin (Rho) | Photoreceptors |
| PKCa | Bipolar cells |
| Parvalbumin | Amacrine cells |
| Calbindin | Horizontal cells |

In some instances, the ability of an rAAV virion to transduce a transgene can be measured by the expression of a reporter protein. In some embodiments, the reporter protein can include GFP, YFP, red cherry, β-galactosidase, or other reporter proteins known in the art.

In some instances, the expression of the reporter protein over time can be determined through a capture of an image of an eye at various time points. As an exemplary example, the expression of GFP can be correlated to an increase in fluorescence. FIG. 7 (lower panels) depicts expression of GFP in the fundus of gerbils at eight weeks after intravitreal injection of various rAAV virions. The amount of fluorescence at a given time point can be used to quantitate expression of a transgene.

In some embodiments, immunofluorescence can be used to determine localization of a transduced gene in a retinal cell compartment described herein. The retinal cell compartment can be labeled by use of an antibody specific for a cell marker disclosed herein. In some instances, the antibody is coupled to a fluorophore. In some instances, a secondary antibody can be used to detect binding of the first antibody. The transduced retina can be cyrosectioned prior to incubation with an antibody against the cell marker of interest, thereby allowing imaging of the bound antibody. The cryosection can then be labeled using antibodies to detect the transduction of a transgene, the presence of a cell maker of interest, and regions of overlap between the two.

The variant capsids disclosed herein may be used to enhance or alter the tropism of a virus or virion in order to enhance its tropism for a desired cell type.

In particular embodiments, the virions or viral vectors comprising a variant capsid protein described herein are used to deliver a gene product to the retina.

In particular embodiments, the virions or viral vectors comprising a variant capsid protein described herein are used to deliver a gene product across the ILM.

In particular embodiments, the virions or viral vectors comprising a variant capsid protein described herein are used to deliver a gene product to the retina by intravitreal injection.

In certain embodiment, the disclosure provides a method of altering the tropism of a virus, e.g., an AAV2.5T or AAV2.5T/7m8 virus, comprising introducing one or more amino acid modifications that confers heparan sulfate binding to a capsid protein of the virus. In related embodiments, the method comprises a method of altering the tropism of a virus, comprising incorporating a variant capsid protein disclosed herein into the virus. In particular embodiments, the alteration comprises one or more amino acid modification introduces one or more amino acids of AAV2 into the capsid protein, including, e.g., any of the modifications described herein. In certain embodiments, the one of the one or more amino acid modifications comprises: (a) a point mutation corresponding to a S576R point mutation in AAV2.5T; (b) a point mutation corresponding to a T579R point mutation in AAV2.5T; (c) a substitution corresponding to a substitution of amino acid residues 576-581 in AAV2.5T with the following amino acid residues: RGNRQA (SEQ ID NO:5); or (d) a substitution corresponding to a substitution of amino acid residues 573-584 in AAV2.5T with the following amino acid residues: NLQRGNRQAATA (SEQ ID NO:7).

In certain embodiments, the method comprises altering the tropism of a virion or viral vector to increase infectivity of RGC as compared to AAV2.5T or AAV2.5T/7m8, wherein the amino acid modification comprises: (a) a S576R point mutation; or (b) a T579R point mutation, e.g., an amino acid mutation corresponding to S576R or T579R in AAV2.5T. Accordingly, the present disclosure comprises a method for selectively delivering a gene product, e.g., a polypeptide, to RGC of a subject, comprising administering to the subject an AAV2.5T virion comprising a capsid protein comprising a S576R point mutation or a T579R point mutation. In certain embodiments, the viral vector is AAV2.5T-S576R or AAV2.5T-T579R.

In certain embodiments, the method comprises altering the tropism of a virion or viral vector to increase infectivity of Müller cells as compared to AAV2.5T or AAV2.5/7m8, wherein the amino acid modification comprises: (a) a S576R point mutation; and (b) a T579R point mutation, e.g., amino acid mutation corresponding to S576R and T579R in AAV2.5T. Accordingly, the present disclosure comprises a method for selectively delivering a gene product, e.g., polypeptide, to Müller cells of a subject, comprising administering to the subject an AAV2.5T/7m8 virus comprising a polynucleotide that encodes the polypeptide, where the virus comprises a capsid protein comprising: (a) a S576R point mutation; and (b) a T579R point mutation. In certain embodiments, the viral vector is AAV2.5T/7m8(+3)Δ2, as described herein.

In certain embodiments, the method comprises altering the tropism of a virion or viral vector to increase infectivity of retinal cells as compared to AAV2.5T or AAV2.5T/7m8 (or variants thereof), wherein the amino acid modification comprises a substitution of amino acid residues corresponding to 576-579 in AAV2.5T with the following amino acid residues: NLQRGNRQAATA (SEQ ID NO:7) or substitution of amino acid residues corresponding to 573-579 or 573-584 with the following amino acid residues: TNQNLQRGNRQAATA (SEQ ID NO:9). Accordingly, in certain embodiments, the present disclosure provides a method for increasing delivery of a gene product, e.g., polypeptide, to retinal cells of a subject, comprising administering to the subject an AAV2.5T/7m8 virus comprising a polynucleotide that encodes the polypeptide, where the virus comprises a capsid protein comprising a substitution of amino acid residues corresponding to 576-579 in AAV2.5T with the following amino acid residues: NLQRGNRQAATA (SEQ ID NO:7) or substitution of amino acid residues corresponding to 573-579 or 573-584 with the following amino acid residues: TNQNLQRGNRQAATA (SEQ ID NO:9). In certain embodiments, the viral vector is AAV2.5T/7m8(–12)-elHSPG (also referred to as AAV2.5T/7m8-12-lHSPG(extra8)), as described herein.

Methods of Expressing Gene Products and Treating Diseases and Disorders

Virions and viral vectors described herein, comprising a variant capsid protein described herein, may be used in delivering a transgene to a cell, e.g., cells of an animal. For example, they may be used in research, e.g., to determine the effect that the gene has on cell viability and/or function. As another example, they may be used in medicine, e.g. to treat a disorder, for example, by delivering a therapeutic gene product to a cell or tissue. Thus, in some aspects of the invention, methods are provided for the expression of a gene in cells, the method comprising contacting cells with a composition of the present disclosure. In some embodiments, contacting occurs in vitro. In some embodiments, contacting occurs in vivo, i.e., the subject composition is administered to a subject. In particular embodiments, a viral vector is administered parenterally, e.g., intravenously, orally, or by injection. In certain embodiments, it is administered to the eye by injection, e.g., administered to the retina, sub-retina or vitreous. In certain embodiments, it is administered by retinal injection, sub-retinal injection, or intravitreal injection.

For instances in particular embodiments in which mammalian cells are to be contacted in vitro with a subject virion or vector comprising a variant capsid protein disclosed herein, the cells may be from any mammalian species, e.g. rodent (e.g. mice, rats, gerbils, squirrels), rabbit, feline, canine, goat, ovine, pig, equine, bovine, primate, human. Cells may be from established cell lines, e.g. WERI cells, 661W cells, or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present disclosure are maintained for fewer than 10 passages in vitro.

If the cells are primary cells, they may be harvested from a mammal by any convenient method, e.g. whole explant, biopsy, etc. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

In certain embodiments, to promote expression of the transgene, the subject virion or gene delivery vector comprising a variant capsid protein is contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc. The subject virion or gene delivery vector comprising a variant capsid protein may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

In certain embodiments, an effective amount of a virion or gene delivery vector comprising a variant capsid protein is provided to produce the expression of the transgene in cells. In particular embodiments, the effective amount may be readily determined empirically, e.g., by detecting the presence or levels of transgene gene product, by detecting an effect on the viability or function of the cells, etc. In certain embodiments, an effect amount of subject virion or gene delivery vector comprising a variant capsid protein will promote equal or greater expression of the transgene in cells than the same amount of a reference virion or viral vector known in the art, e.g., AAV2.5T or AAV7m8. In certain embodiments, expression is enhanced 2-fold or more relative to the expression from a reference, or control virion or viral vector, for example 3-fold, 4-fold, or 5-fold or more, in some instances 10-fold, 20-fold or 50-fold or more, e.g. 100-fold. In certain embodiments, the enhanced expression occurs is a particular cell type, e.g., any of the ocular cells described herein.

For instances in which cells are contacted in vivo with a subject virion or gene delivery vector comprising a variant capsid protein described herein, the subject may be any mammal, e.g. rodent (e.g. mice, rats, gerbils), rabbit, feline, canine, goat, ovine, pig, equine, bovine, or primate (e.g. human, or non-human primate). The methods and compositions of the present disclosure find use in the treatment of any condition that can be addressed, at least in part, by gene therapy of cells. Thus, the compositions and methods of the present disclosure find use in the treatment of individuals in need of a cell therapy. Cells include but are not limited to blood, eye, liver, kidney, heart, muscle, stomach, intestine, pancreas, and skin.

In certain embodiments, the disclosure provides a method of providing a gene product to a retina of a subject, comprising administering to the subject by intravitreal injection a pharmaceutical composition comprising a recombinant virion or vector described herein, wherein the recombinant virus comprises a variant capsid provide disclosed herein and a polynucleotide sequence that encodes the gene product.

In particular embodiments, the subject has been diagnosed with or is suspected of having one or more diseases or disorders selected from the group consisting of: age-related macular degeneration (AMD), wet-AMD, dry-AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, and diabetic retinal edema.

In certain embodiments, the gene product inhibits neovascularization, e.g., choroidal neovascularization (CNV), in the retina of the subject. It has been found that many cellular factors play important roles in regulation in CNV generation, among which may include but are not limited to vascular endothelial growth factor (VEGF), VEGF receptor (VEGFR), platelet-derived growth factor (PDGF), hypoxia inducible factor (HIF), angiopoietin (Ang) and other cytokines, mitogen-activated protein kinases (MAPK). In particular embodiments, the gene product inhibits one or more of these cellular factors.

In particular embodiments, the gene product is an anti-VEGF protein, such as, but not limited to the VEGF-binding proteins or functional fragments thereof disclosed in U.S. Pat. Nos. 5,712,380, 5,861,484 and 7,071,159 and VEGF-binding fusion proteins disclosed in U.S. Pat. No. 7,635,474. An anti-VEGF protein may also include the soluble Fms-related tyrosine kinase-1 (sFLT-1) protein as described in U.S. Patent Application Publication No. 2013/0323302.

The recombinant virions and viral vectors of the present disclosure may comprise a sequence encoding an anti-VEGF protein, including but not limited to anti-VEGF antibodies or fragments thereof, such as aflibercept, ranibizumab, and bevacizumab, and the naturally occurring protein sFlt-1, as described in U.S. Pat. No. 5,861,484 and the sequence disclosed by SEQ ID NO: 109 in US2013/0323302. An sFlt-1 amino acid sequence is disclosed herein as SEQ ID NO:42. It also includes, but is not limited to functional fragments thereof, including sequences of sFlt-1 domain 2 or those set forth in SEQ ID NO: 121 of U.S. Patent Application Publication No. 2013/0323302, as well as related constructs, such as the VEGF-binding fusion proteins disclosed in U.S. Pat. No. 7,635,474. An s-Flt-1 functional fragment is disclosed herein as SEQ ID NO:43. An anti-VEGF protein may also include any of the sFLT-1 proteins, variants or fragments thereof described in U.S. Patent Application Publication No. 2013/0323302. In some embodiments, the anti-VEGF protein is ranibizumab (commercially available under the trademark Lucentis® (Genentech, San Francisco, Calif.), see FIG. 1 of U.S. Pat. No. 7,060,269 for the heavy chain and light chain variable region sequences of ranibizumab); bevacizumab (commercially available under the trademark Avastin® (Genentech, San Francisco, Calif.), see FIG. 1 of U.S. Pat. No. 6,054,297 for the heavy chain and light chain variable region sequences of bevacizumab); or aflibercept (commercially available under the trademark Eylea® (Regeneron, Tarrytown, N.Y.). In certain embodiments, bevacizumab includes the following heavy and light chain variable domain sequences, respectively:

(SEQ ID NO: 36)
EVQLVESGGGLVQPGGSLRLSCAASGYTFTNYGMNWVRQAPGKGLEWVG

WINTYTGEPTYAADFKRRFTFSLDTSKSTAYLQMNSLRAEDTAVYYCAK

YPHYYGSSHWYFDVWGQGTL;
and (SEQ ID NO: 37)
DIQMTQSPSSLSASVGDRVTITCSASQDISNYLNWYQQKPGKAPKVLIY

FTSSLHSGVPSRFSGSGSGTDFTLTISSLQPEDFATYYCQQYSTVPWTF

GQGTKVEIKRTV.

In certain embodiments, ranibizumab includes the following heavy and light chain variable domain sequences, respectively:

(SEQ ID NO: 38)
EVQLVESGGGLVQPGGSLRLSCAASGYDFTHYGMNWVRQAPGKGLEWVG

WINTYTGEPTYAADFKRRFTFSLDTSKSTAYLQMNSLRAEDTAVYYCAK

YPYYYGTSHWYFDVWGQGTL;
and (SEQ ID NO: 39)
DIQLTQSPSSLSASVGDRVTITCSASQDISNYLNWYQQKPGKAPKVLIY

FTSSLHSGVPSRFSGSGSGTDFTLTISSLQPEDFATYYCQQYSTVPWTF

GQGTKVEIKRTV.

In certain embodiments, aflibercept includes the following amino acid sequence:

(SEQ ID NO: 40)
MVSYWDTGVLLCALLSCLLLTGSSSGSDTGRPFVEMYSEIPEIIHMTEG

RELVIPCRVTSPNITVTLKKFPLDTLIPDGKRIIWDSRKGFIISNATYK

EIGLLTCEATVNGHLYKTNYLTHRQTNTIIDVVLSPSHGIELSVGEKLV

LNCTARTELNVGIDFNWEYPSSKHQHKKLVNRDLKTQSGSEMKKFLSTL

TIDGVTRSDQGLYTCAASSGLMTKKNSTFVRVHEKDKTHTCPPCPAPEL

LGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGK.

These sequences can be expressed from DNA encoding such sequences using the genetic code, a standard technique that is understood by those skilled in the art. As can be appreciated by those with skill in the art, due to the degeneracy of the genetic code, anti-VEGF protein sequences can be readily expressed from a number of different DNA sequences.

"sFlt-1 protein" herein refers to a polypeptide sequence, or functional fragment thereof, with at least 90%, or more, homology to the naturally occurring human sFLT-1 sequence, such that the sFlt-1 protein or polypeptide binds to VEGF and/or the VEGF receptor. Homology refers to the % conservation of residues of an alignment between two sequences (e.g. as Naturally occurring human sFLT-1 protein may include any suitable variants of sFLT-1, including, but not limited to functional fragments, sequences comprising insertions, deletions, substitutions, pseudofragments, pseudogenes, splice variants or artificially optimized sequences. In some cases, "sFLT-1 protein" may be at least about 90%, 91%, 92%, 93%, 94%, 95%, 96%, 97%, 98%, 99%, 99.9%, 99.99% or 100% homologous to the naturally occurring human sFLT-1 protein sequence. In some cases, "sFLT-1 protein" may be at most about 90%, 91%, 92%, 93%, 94%, 95%, 96%, 97%, 98%, 99%, 99.9%, 99.99% or 100% homologous to the naturally occurring human sFLT-1 protein sequence. In some cases, "sFLT-1 protein" may be at least about 90%, 91%, 92%, 93%, 94%, 95%, 96%, 97%, 98%, 99%, 99.9%, 99.99% or 100% spatially homologous to the naturally occurring human sFLT-1 protein conformation. In some cases, "sFLT-1 protein" may be at most about 90%, 91%, 92%, 93%, 94%, 95%, 96%, 97%, 98%, 99%, 99.9%, 99.99% or 100% spatially homologous to the naturally occurring human sFLT-1 protein conformation.

Further, the soluble truncated form of the VEGF receptor FLT-1, sFLT-1, is the only known endogenous specific inhibitor of VEGF. In nature, it is generated by alternative mRNA splicing and lacks the membrane-proximal immunoglobulin-like domain, the transmembrane spanning region and the intracellular tyrosine-kinase domain. Structurally, FLT-1 and sFLT-1 protein may both comprise multiple functional domains. In some variants, FLT and sFLT proteins commonly share 6 interlinked domain; 3 domains involved in dimerization of the protein and 3 domains involved in the binding of a ligand, such as VEGF.

sFLT-1 is a soluble truncated form of the FLT-1 and it is expressed endogenously. As described herein, "soluble" FLT-1, or sFLT-1 refers to FLT-1 that is not restricted to the cellular membrane. Unbound sFLT-1 may diffuse freely in extracellular space or solution.

sFLT-1 is the only known endogenous specific inhibitor of VEGF. This interaction is specific and can be competed away with 100-fold excess unlabeled VEGF. In some cases, the angiostatic activity of sFLT-1 may result from inhibition of VEGF by two mechanisms: i) sequestration of VEGF, to which it binds with high affinity, and ii) formation of inactive heterodimers with membrane-spanning isoforms of the VEGF receptors FLTt-1 and FLK-1/KDR. As known in the art, in vitro binding assays have indicated that sFLT-1 binds VEGF with high affinity and may also inhibit VEGF driven proliferation of human umbilical vein endothelial cells. In animal models for cancer, sFLT-1 inhibits tumor growth. In some cases, sFLT-1 may function in a substoichiometric or dominant negative manner, as excess VEGF in the extracellular space may be prevented from binding and subsequently activating the VEGF receptor. These properties of sFLT-1 have been described in Kendall and Thomas, 1993; Proc Natl Acad Sci. 90: 10705-10709, which is incorporated herein by reference in its entirety. As is known in the art, functional fragments of sFLT-1 can be used in place of the full-length protein. More specifically, the VEGF binding domain (domain 2), or alternatively domain 2 of sFLT-1 plus domain 3 from sFLT1, KDR, or another family member, can be used to bind and inactivate VEGF. Such functional fragments are described in Wiesmann et al., 1997; Cell, 91: 695-704, which is incorporated herein by reference in its entirety. The terms "sFLT-1" and "a functional fragment of sFLT-1" are equivalent and used here interchangeably.

In certain embodiments, virions and viral vectors comprising a variant capsid protein that confers altered tropism to the virion or viral vector is used to treat a disease or disorder of the cells for which tropism or the virion or viral vector is increased.

In certain embodiments, a virion or viral vector comprising a variant capsid protein comprising a S576R point mutation or a T579R point mutation is administered (e.g., via intravitreal injection) to a subject to treat a disease or disorder associated with retinal ganglial cells (RGC), or to deliver a therapeutic gene product to RGC. In particular embodiments, the virion or viral vector is an AAV2.5T or AAV2.5T/7m8 virion comprising a capsid protein comprising a S576R point mutation or a T579R point mutation. In certain embodiments, the virion or viral vector comprises a S576R point mutation or a T579R point mutation, but not both. In certain embodiments, the disease or disorder is glaucoma or a neurodegenerative disease.

In certain embodiments, a virion or viral vector comprising a variant capsid protein comprising a S576R point mutation and a T579R point mutation is administered (e.g., via intravitreal injection) to a subject to treat a disease or disorder associated with Müller cells, or to deliver a therapeutic gene product to Müller cells. In particular embodiments, the virion or viral vector is an AAV2.5T or AAV2.5T/7m8 virion comprising a capsid protein comprising a S576R point mutation and a T579R point mutation. In certain embodiments, the disease or disorder is a retinal disease.

In certain embodiments, a virion or viral vector comprising a substitution of amino acid residues corresponding to 573-584 in AAV2.5T/7m8 with the following amino acid residues: NLQRGNRQAATA (SEQ ID NO:7) is administered (e.g., via intravitreal injection) to a subject to treat a disease or disorder associated with retinal cells. In particular embodiments, the virion or viral vector is an AAV2.5T or AAV2.5T/7m8 virion comprising a capsid protein comprising a substitution of amino acid residues corresponding to 573-584 in AAV2.5T/7m8 with the following amino acid residues: NLQRGNRQAATA (SEQ ID NO:7). In particular embodiments, the disease or disorder is a retinal disease.

In some embodiments, the subject method results in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

In some instances, the expression of the transgene, e.g. as detected by measuring levels of gene product, by measuring therapeutic efficacy, etc., may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g., as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In particular embodiments, a subject is administered to one eye or to each of both eyes about $1 \times 10^8$ vector genomes or more, in some cases $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes or more. In some cases, the amount of vector genomes that is delivered is at most about $1 \times 10^{15}$ vector genomes, e.g. $1 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes, and sometimes no less than $1 \times 10^8$ vector genomes. In some cases, the amount of vector genomes that is delivered is $1\times10^{10}$ to $1\times10^{11}$ vector genomes. In some cases, the amount of vector genomes that is delivered is $1\times10^{10}$ to $3\times10^{12}$ vector genomes. In some cases, the amount of vector genomes that is delivered is $1\times10^{9}$ to $3\times10^{13}$ vector genomes. In some cases, the amount of vector genomes that is delivered is $1\times10^{8}$ to $3\times10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be $1\times10^{6}$. In some cases, the MOI may be $1\times10^{5}$-$1\times10^{7}$. In some cases, the MOI may be $1\times10^{4}$-$1\times10^{8}$. In some cases, recombinant viruses of the disclosure are at least about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$, $1\times10^{16}$, $1\times10^{7}$, and $1\times10^{18}$ MOI. In some cases, recombinant viruses of this disclosure are $1\times10^{8}$ to $3\times10^{14}$ MOI. In some cases, recombinant viruses of the disclosure are at most about $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times10^{8}$ to about $1\times10^{15}$ particles of recombinant virions or viruses, about $1\times10^{9}$ to about $1\times10^{14}$ particles of recombinant virions or viruses, about $1\times10^{10}$ to about $1\times10^{13}$ particles of recombinant virions or viruses, or about $1\times10^{11}$ to about $3\times10^{12}$ particles of recombinant virions or viruses.

In some aspects, no virion or vector is detected in the human subject's tear, blood, saliva or urine samples 7, 14, 21 or 30 days after administering said pharmaceutical composition. In some aspects, the presence of the viral vector is detected by qPCR or ELBA as known in the art.

In some aspects, a subject's best corrected visual acuity (BCVA) improves by 1, 2 3, 4, 5 or more lines following a method of treatment described herein.

In some aspects, a reduction in neovascularization as assessed by Fluorscein Angiography (FA) follows the administering step.

In some cases, retinal thickness may be measured to examine the effects of treatment. In some cases, the central retinal thickness of the human subject does not increase by more than 50 microns, 100 microns, or 250 microns within 12 months following treatment with the pharmaceutical composition of the disclosure. In some cases, the central retinal thickness of the human subject decreases by at least 50 microns, 100 microns, 200 microns, 250 microns, 300 microns, 400 microns, 500 microns, 600 microns within 3 months, 6 months or 9 months 12 months following treatment with the pharmaceutical composition of the disclosure. The decrease in the central retinal thickness of the human subject may be measured comparing the central retinal thickness at point in time to a baseline measurement taken at or within 1, 3, 7 or 10 days of the administration of the pharmaceutical composition of the disclosure.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Construction of AAV2.5T Swap Mutants

AAV2.5T is a hybrid capsid containing regions from AAV2 and AAV5. AAV2.5T is capable of transducing the retina when delivered subretinally, but not when injected intravitreally, see FIG. 1A. AAV2.5T transduction may be blocked by the ILM, which is enriched with heparin sulfate. The heparan sulfate proteoglycan (HSPG) binding region of AAV2.5T is identical to that of AAV5 except for a single substitution of A to T in aa582 of AAV2.5T (aa581 of AAV5) (see FIG. 3A (i-iii)). AAV5 has negligible heparin sulfate binding, where AAV2 has high affinity for heparin sulfate. In order to generate an AAV vector capable of transfecting cells of the retinal following intravitreal injection, a series of swap-variants were created incorporating portions of the AAV2 HSPG binding region into the HSPG binding region of AAV2.5T.

AAV7m8 vectors also have enhanced ability to transduce the retina. In order to further improve the ability of AAV2.5T capsids to transduce the retina, a series of mutants were made that include the 7m8 insert at various positions within the HSPG binding region.

Figures 2, 3A:
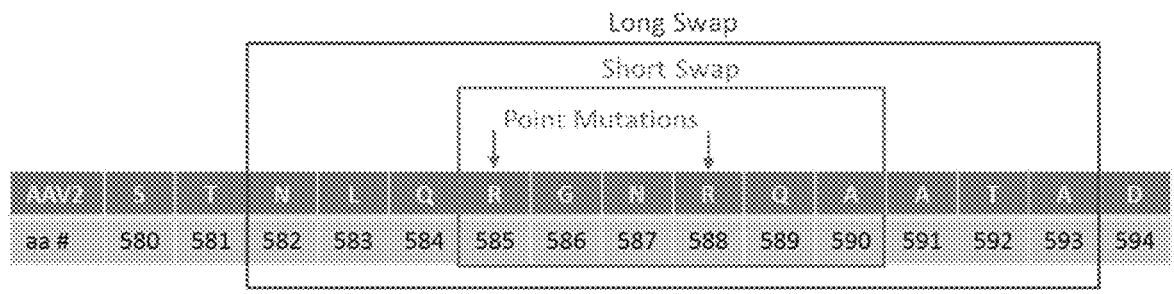
FIG. 2 is a diagram showing amino acid residues 580-594 of the AAV2 capsid protein (SEQ ID NO:44), and indicating the amino acid residues modified by various point mutations and swaps in illustrative modified capsid proteins described herein.
FIG. 3A provides a sequence alignment of the HSPG binding region of the indicated capsids (SEQ ID NOs: 44-53). Sequences from the parental AAV2 sequence are indicated in grey. AAV2.5T-2pt (SEQ ID NO:49) includes the indicated point mutations at amino acid residues 576 and 579. AAV2.5T-sHSPG(correct) (SEQ ID NO:50) includes a replacement of amino acid residues 576-581 of AAV2.5 by amino acid residues 585-590 of AAV2. AAV2.5T-sHSPG (extra2) (SEQ ID NO:51) includes a replacement of amino acid residues 576-580 of AAV2.5 by amino acid residues 585-590 of AAV2, resulting in an increase in total length of 2 amino acids. AAV2.5T-lHSPG(correct) (SEQ ID NO:52) includes a replacement of amino acid residues 573-584 of AAV2.5T by the amino acid residues 582-593 of AAV2. AAV2.5T-lHSPG(extra8) (SEQ ID NO:53) includes a replacement of amino acid residues 576-579 of AAV2.5T by the amino acid residues 582-593 of AAV2, resulting in an increase in the total length of 8 amino acids.

Site-directed mutagenesis and recombinant DNA techniques were used to generate a series of "swap" variants of AAV2.5T, which introduced amino acid residues from the heparan sulfate proteoglycan (HSPG) binding region of AAV2 into AAV2.5T or AAV2.5/7m8 hybrid backbones. The HSPG binding region of AAV2.5T/7m8 variants are shown in FIG. 3B (iv)-(ix). Three types of swap variants were generated: (1) point mutants; (2) short swap variants (sHPSG); and (3) long swap variants (lHSPG). The location of the point mutations and the amino acids transferred in the short swap and long swap mutants are depicted in FIG. 2. FIG. 3A provides a sequence alignment of regions of HSPG swap variants on the 2.5T backbone. FIG. 3B provides alignments of regions of HSPG swap variants on 2.5T/7m8 backbones.

The short AAV2.5T swap variants (sHSPG) were made by replacing amino acid residues corresponding to 576-SST-TAP-581 (SEQ ID NO:26) (sHSPG(correct)) (FIG. 3A(vii)) or 576-SSTT-579 (SEQ ID NO:27) (sHSPG(extra2)) (FIG. 3A(viii)) of 2.5T with amino acid residues 585-RNGRQA-590 (SEQ ID NO:5) of AAV2. The long swap variants (lHSPG) were made by replacing amino acid residues corresponding to 573-584 (lHSPG(correct)) or 576-579 (lHSPG(extra 8) of 2.5T with amino acid residues 582-593 of AAV2. Illustrative swap mutants are shown in FIGS. 3A-3B. The double point mutation (S575R+T579R), the sHSPG, and the lHSPG swap variants were made on 2.5T backbone (FIG. 3A), 2.5T/7m8(0) and 2.5T/7m8(−12) backbone (FIG. 3B). Two single mutants, S575R and T579R, were also made to determine if one of the sites was detrimental to the capsid. FIGS. 4A-4C provide the amino acid sequences of the capsid proteins of selected swap variants.

Variants were generated using a triple transfection method of plasmid with ITRs carrying the GFP transgene, a plasmid with the Rep/Cap genes, and a plasmid containing adenovirus-helper functions, followed by ultracentrifugation to separate the empty and full capsids.

The swap variant viruses were characterized by quantitative PCR to establish titer and packaging, and western blot was conducted to ensure the correct ratio of the VP1, VP2 and VP3 capsid proteins.

The majority of the swap variants packaged, resulting in a titer greater than $1 \times 10^{12}$ vector genomes (vg)/ml, and western blots showed the correct ratio of VP1, VP2 and VP3. However, four swap variants did not package and showed much lower titer as compared to others. Table 2 indicates the titer of 13 swap variants, with those exhibiting low titer marked with an asterisk.

TABLE 2

Titer of 2.5T HSPG swap variants

| Vector | Titer (vg/ml) |
| --- | --- |
| 2.5T-S576R | 4.04E+13 |
| 2.5T-T579R | 5.17E+13 |
| *2.5T-2pt | 1.94E+10, 4.44E+10 |
| *2.5T-sHSPG | 1.75E+10, 1.12E+11 |
| *2.5T-lHSPG | 5.11E+11, 1.45E+11 |
| 2.5T/7m8(+3)- Δ2 | 7E+13 |
| 2.5T/7m8(0)-sHSPG | 6.62E+12 |
| *2.5T/7m8(0)-lHSPG | 4.15E+11, 2.34E+11 |
| 2.5T/7m8(−12)-Δ2 | 4.6E+12 |
| 2.5T/7m8(−12)-sHSPG2 | 5.01E+12 |
| 2.5T/7m8(−12)-elHSPG | 1.86E+13 |
| 2.5T/7m8(−12)-sHSPG | 9.64E+12 |
| 2.5T/7m8(−12)-lHSPG | 7.76E+12 |

Example 2

Heparan Binding Affinity of AAV2.5T Swap Variants

The ability of the swap variants to bind HSPG was determined by performing a heparan binding assay using a pre-packed GE heparan column. Vector was loaded on the column, which was then washed, and finally eluted with increasing concentrations of NaCl (100 mM-1 M). Fractions of Load, Flow-through, Wash, and Elution were collected and analyzed by dot-blot using the B1 antibody.

The swap variants demonstrated varying levels of binding affinity to the heparan column. Except for the single mutant, 2.5T-S576R, all of the swap variants gained HSPG binding affinity as compared to 2.5T parent. FIG. 5 shows the binding elution profile as determined by dot-blot.

Example 3

Transduction of HEK293 and CHOK1 Cells

In vitro transductions were performed on HEK293 cells or CHOK1 cells at an MOI of $3 \times 10^5$ for five days. Images were captured and flow cytometry was performed at the end of the study.

Table 3 provides the in vitro transduction profile of the indicated swap mutants in HEK293 and CHOK1 cells, with the result of a paired AAV2.5T transduction given in parenthesis, and FIG. 6 shows the percent transduction of HEK293 cells achieved by the indicated swap variants. Although the resulting transgene expression was lower as compared to the 2.5T parent, all of the swap variants tested were able to transduce both HEK293 and CHOK1 cells.

TABLE 3

In vitro transduction profile of 2.5T HSPG swap variants

| Vector | Titer (vg/ml) | Transduction in HEK293* | Transduction in CHOK1 |
| --- | --- | --- | --- |
| 2.5T-S576R | 4.04E+13 | 65.95% (97.95%) | 93.4% (91.55%) |
| 2.5T-T579R | 5.17E+13 | 7.32% (97.95%) | 48.9% (91.55%) |
| 2.5T/7m8(+3)-Δ2 | 7E+13 | 9% (80%) | 23.1% (41.2%) |
| 2.5T/7m8(0)-sHSPG | 6.62E+12 | 14% (96%) | 12% (29%) |
| 2.5T/7m8(−12)-Δ2 | 4.6E+12 | 22% (96%) | 4% (29%) |
| 2.5T/7m8(−12)-sHSPG2 | 5.01E+12 | 21% (96%), 5% (97.95%) | 4% (29%), 15.85% (91.55%) |
| 2.5T/7m8(−12)-elHSPG | 1.86E+13 | 69% (96%), 23.1% (80%), 36.18% (97.95%) | 11% (29%), 10.55% (41.2%), 46.7% (91.55%) |
| 2.5T/7m8(−12)-sHSPG | 9.64E+12 | 3.89% (97.95%) | 20.25% (91.55%) |
| 2.5T/7m8(−12)-lHSPG | 7.76E+12 | 7.86% (97.95%) | 24.55% (91.55%) |

*results of paired AAV2.5T transduction are given in parenthesis.

Example 4

Expression and Tropism in Pig Retinal Explants

Ex vivo pig retinal explants were maintained on transwells as described in PCT/US2017/030636, the disclosure of which is incorporated in its entirety, and were transduced with the swap variant viruses at an MOI of $4 \times 10^4$ for two weeks. Live fluorescent images were captured at one and two weeks following transduction.

Swap variants displayed variable amounts of gene expression and altered tropism to retinal cells in the pig explants. FIGS. 7A-7K show live imaging of pig retinal explants for the indicated swap mutants. The pig explant samples with higher GFP expression were cryo-sectioned and stained to identify different retinal cell types (FIGS. 8A-8F). Interestingly, all the examined variants showed different tropism from 2.5T parent, even the single point mutants. 2.5T parent restrictedly only infect photoreceptor cells in pig explants (FIG. 8A). Single point mutations 2.5T-S576R and 2.5T-T579R exhibited reduced photoreceptor cell transduction, but were able to transduce RGC cells (FIGS. 8B and 8C). The 2.5T/7m8(+3)-Δ2 vector retained the ability of AAV2.5T to transduce photoreceptor cells, and also exhibited the ability to transduce Müller cells (FIG. 8E). The 2.5T/7m8(−12)-elHSPG vector exhibited variable transduction ability (FIG. 7 panel (I)). Of the four explants transduced by 2.5T/7m8(−12)-elHSPG, only one showed strong transduction of almost all the retinal cells (FIG. 8F, right hand side labeled PEX 1601). However, the other three explants (two from PEX1603 and one from PEX1601) showed much lower transduction levels (a representative image set is shown in FIG. 8F, left hand side).

It was interesting that some swap variants were able to transduce pig retinal explant and actually showed different tropism than the 2.5T parent. For example, 2.5T/7m8(+3)-Δ2 showed a much higher tropism in Müller cells than 2.5T parent, which makes it a potential vector candidate for targeting Müller cells. 2.5T/7m8(−3) had high expression levels in pig explants, and it transduced almost all the retinal cells stained. Therefore, 2.5T/7m8(−3) was chosen as the backbone to build the HSPG double mutant (S576R+T579R), sHSPG swap, and lHSPG swap variants. In addition, HSPG swap variants were also built upon 2.5T/7m8(−12). In particular the 2.5T/7m8(−12) elHSPG showed promising transduction in the pig retinal explants.

Example 5

Expression Following Intravitreal Administration to Gerbil Retina

In vivo studies were performed in gerbils, which were intravitreally (IVT) injected with 2E+10 vg/eye of swap variant virus. Fluorescence fundus images were captured at eight weeks following IVT injection (FIG. 9).

Certain swap variants showed significantly improved gene expression in the gerbil retina at eight weeks following IVT administration as compared to parent 2.5T. These results show that certain swap variants may be used to efficiently cross the ILM following IVT administration. As expected, AAV2.5T did not efficiently cross the ILM. AAV2.5T/7m8(+3)Δ and AAV2.5T/7m8(−12)elHSPG were able to efficiently cross the ILM and transduce retinal cells following intravitreal injection, and AAV2.5T/7m8(−3) lHSPG exhibited a moderate ability to traverse the ILM.

Figure 12A:
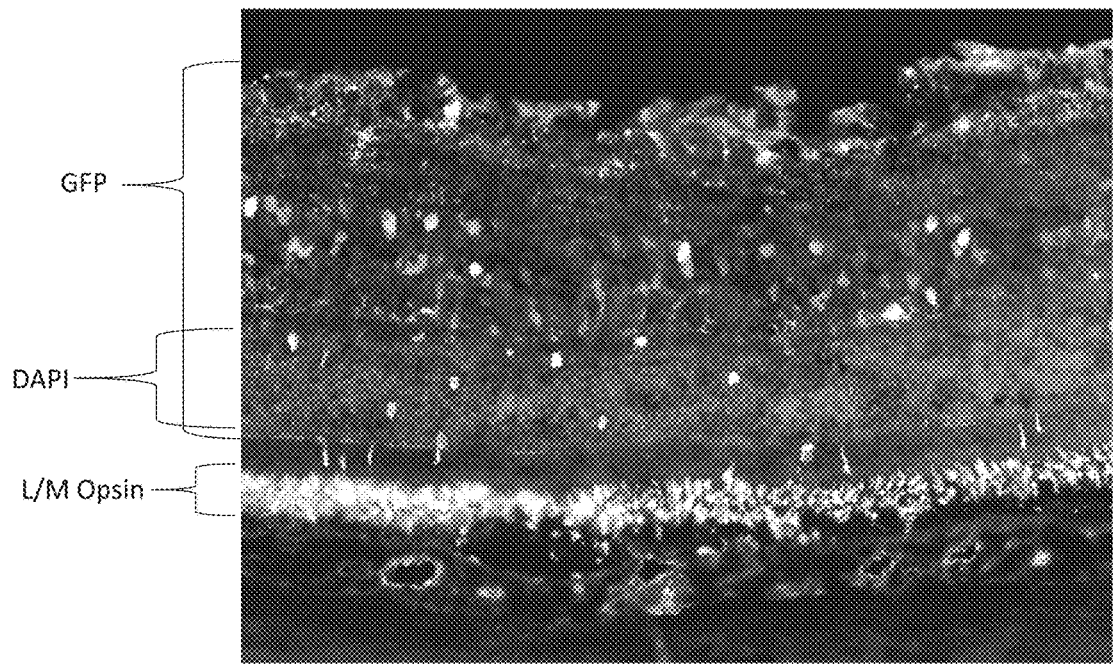
Figure 12B:
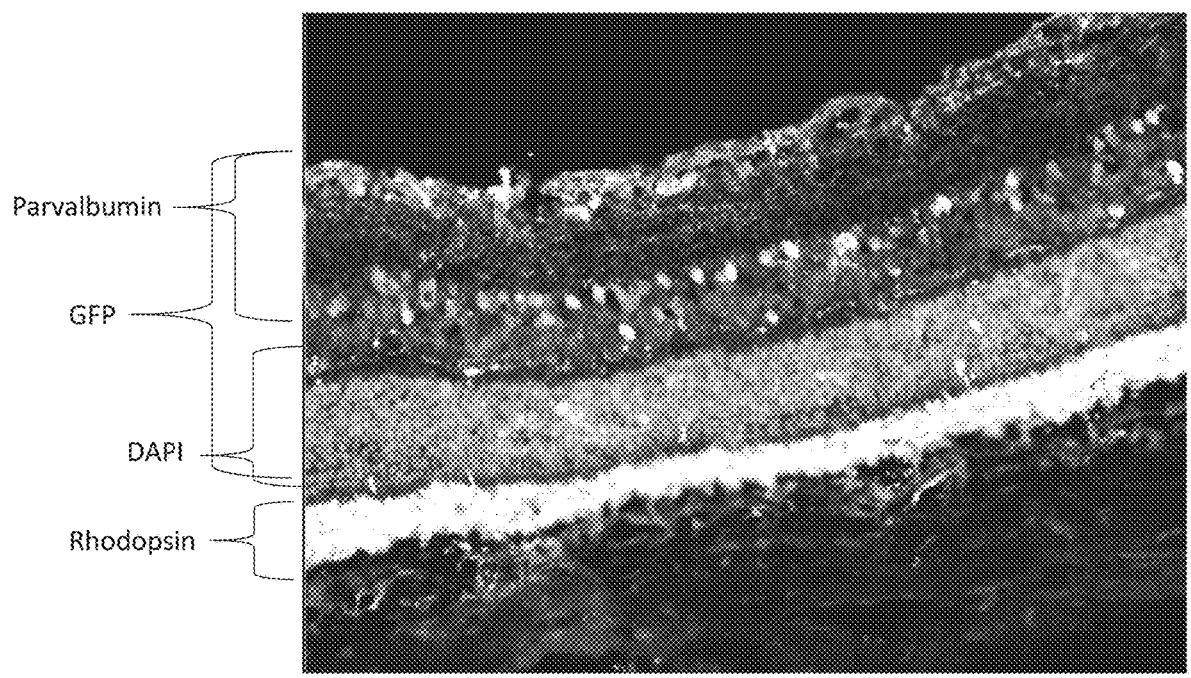
Figure 13:
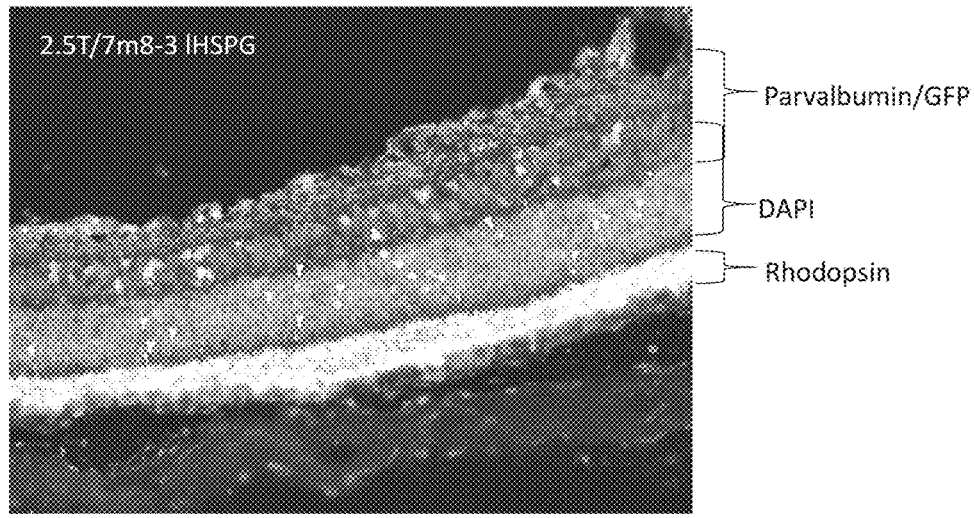
Figure 14A:
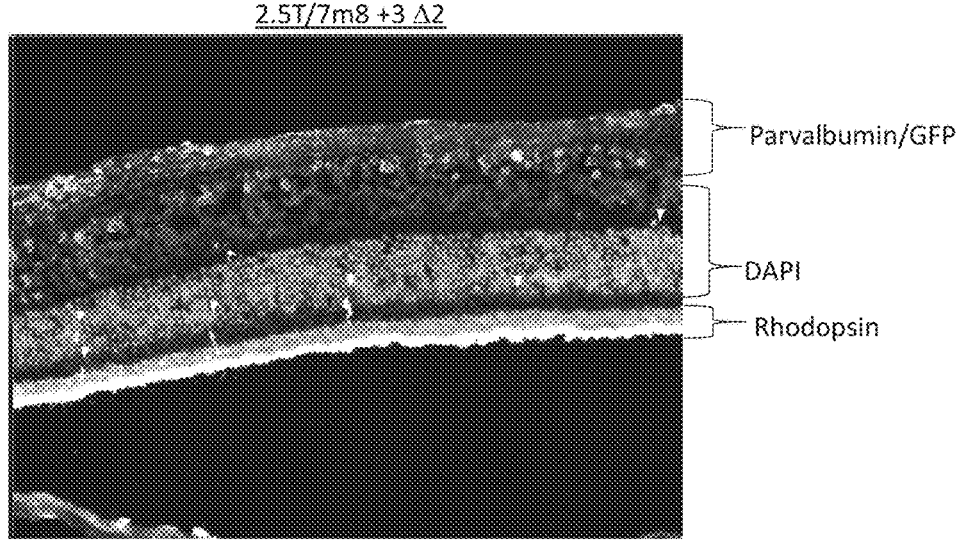
Figure 14B:
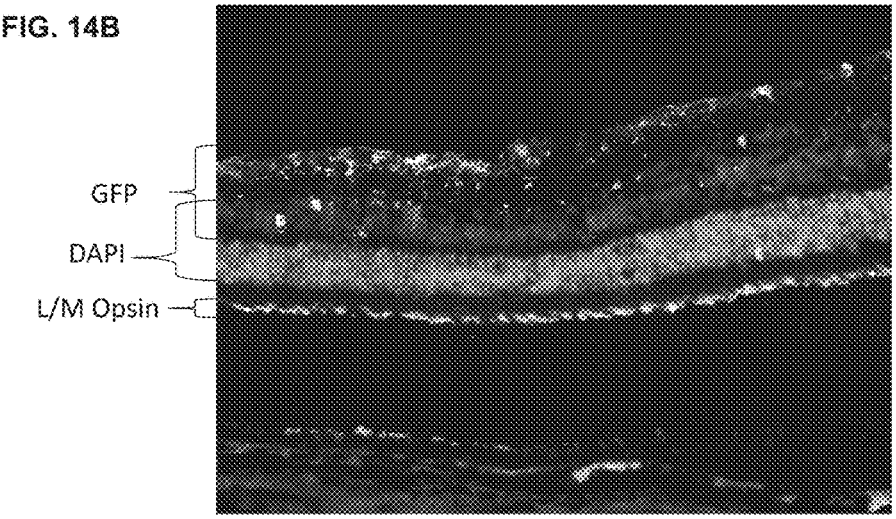

Following fundus imaging, animals were sacrificed, and retinas were removed and cryosectioned. Sections were stained with DAPI, and were probed for GFP, L/M Opsin, parvalbumin, and rhodopsin. FIGS. 12A and 12B provide immunofluorescent images of the retina of a gerbil that received 2.5T/7m8(−12)elHSPG via intravitreal injection. The images show that GFP expression colocalized with parvalbumin and DAPI. FIG. 13 provides and immunofluorescent image of the retina of a gerbil that received 2.5T/7m8(−3) lHSPG. The image shows that GFP expression colocalized with parvalbumin and DAPI. FIGS. 14A and 14B provide immunofluorescent images of the retina of a gerbil that received 2.5T/7m8(+3) Δ2. The images show that GFP expression colocalized with parvalbumin and DAPI.

Example 6

Determination of Neutralizing Antibody Profile

Neutralizing antibody (nAB) profiles were determined for swap variant virus by in vitro assay. Briefly, seven 1:3.1-fold serial dilutions of pooled human IgG antibodies (Gammaguard IVIG) were prepared (1:1, 1:3.1, 1:10, 1:31, 1:100, 1:310, and 1:1000). IgG serial dilutions were combined with swap variant virus carrying GFP, and used to transduce 293T cells at MOI of 1E+5 vg/cell. Transductions were carried out in quadruplicate. At 72 hours post-transduction, GFP expression was measured. Results are reported in FIGS. 11A-11E. Swap variants were shown to have a similar nAb profile to the AAV2.5T parent vector, which is improved over AAV2 (compare FIG. 1B top panel with FIGS. 11A-11E).

Example 7

Expression Following Intravitreal Administration to Non-Human Primate Retina

Figure 15:
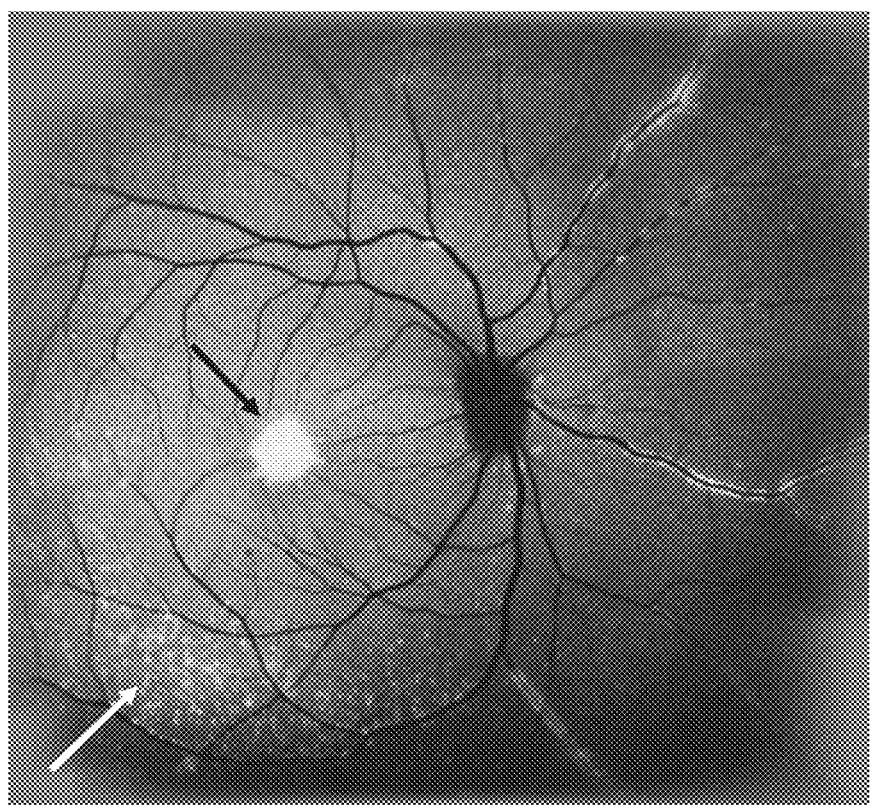

In vivo studies were performed in green monkeys (*Chlorocebus sabaeus*), which were intravitreally injected with 2.5E+12 vg/eye of swap variant viruses AAV2.5T/7m8(−12)elHSPG and AAV2.5T/7m8(+3) Δ2. OTC autofluorescence images were captured using a SPECTRALIS OCT (Heidelberg Engineering) at twelve weeks post injection and are shown in FIG. 15 (AAV2.5T/7m8(−12)elHSPG), and FIG. 19 (AAV2.5T/7m8(+3) Δ2). Unexpectedly, AAV2.5T/7m8(−12)elHSPG exhibited expression in the macula as well as inside the blood arcades. The blood arcade region of the retina has the thickest ILM, which is thought to block transduction of retinal cells by most AAV when injected intravitreally.

Figure 16:
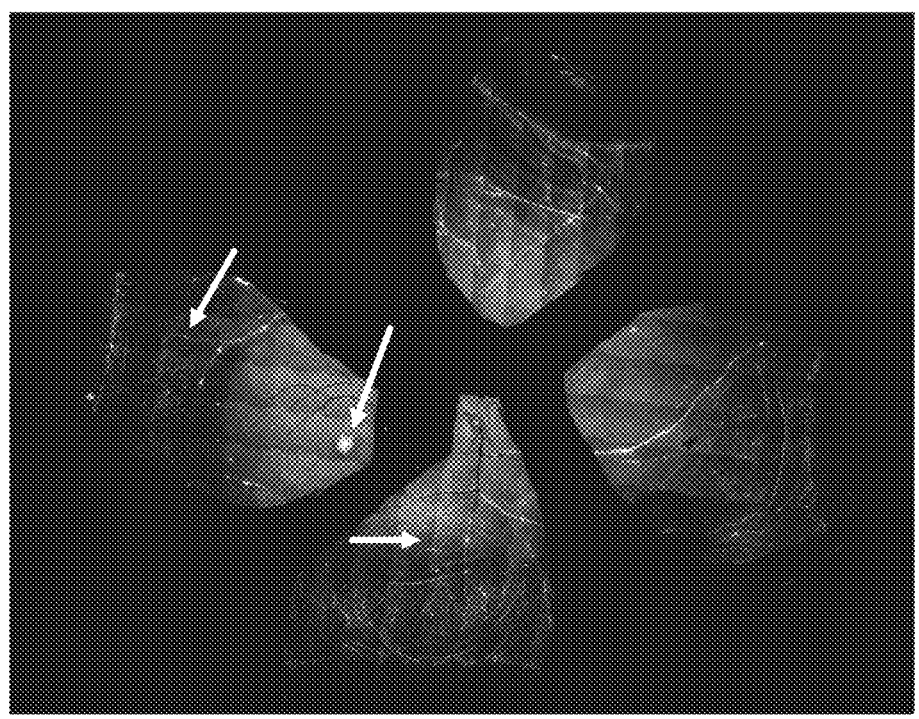

Following OTC autofluorescence, animals were sacrificed, and retinas were removed. Retina flat mounts were made from animals injected with swap variant viruses. Live imaging of flat mounted retinas is depicted in FIG. 16 (2.5T/7m8(−12)elHSPG) and FIG. 20 (2.5T/7m8(+3) Δ2). 2.5T/7m8(−12)elHSPG exhibited expression throughout the retina, whereas expression from 2.5T/7m8(+3) Δ2 was concentrated in the macula.

Next, retinas were cryo-sectioned to obtain transverse sections at the points indicated by the arrows on the flat mount images. Immunofluorescent imaging confirmed that 2.5T/7m8(−12)elHSPG was successfully able to penetrate the ILM and transduce cells from the fovea to the ora serrata, as evidenced by the GFP expression shown in FIG. 18, as well as transverse sections taken at the fovea (FIG. 17A) mid-periphery (FIG. 17B) and periphery (FIG. 17C), which show robust GFP expression in RGC, cones, and Müller cells. Immunofluorescent imaging confirmed that 2.5T/7m8(+3) Δ2 primarily transduces Müller cells in the fovea of non-human primates (FIGS. 20 and 21).

The invention claimed is:

1. A non-naturally-occurring modified adeno-associated virus (AAV) capsid protein, comprising one or more amino acid modification that confers heparan sulfate binding to the capsid protein, wherein the AAV is an AAV2.5T/7m8.

2. The modified AAV capsid protein of claim 1, wherein the AAV2.5T/7m8 is an AAV2.5T/7m8(+3), an AAV2.5T/7m8(0), an AAV2.5T/7m8(−12), an AAV2.5T/7m8(−9), an AAV2.5T/7m8(−6), or an AAV2.5T/7m8(−3), wherein the AAV2.5T/7m8(+3) comprises an insertion of the amino acids LALGETTRPA between residues 579-580 of AAV2.5T, the AAV2.5T/7m8(0) comprises an insertion of the amino acids LALGETTRPA between residues 578-579 of AAV2.5T, the AAV2.5T/7m8(−12) comprises an insertion of the amino acids LALGETTRPA between residues 574-575 of AAV2.5T, the AAV2.5T/7m8(−9) comprises an insertion of the amino acids LALGETTRPA between residues 575-576 of AAV2.5T, wherein the AAV2.5T/7m8(−6) comprises an insertion of the amino acids LALGETTRPA between residues 576-577 of AAV2.5T, and the AAV2.5T/7m8(−3) comprises an insertion of the amino acids LALGETTRPA between residues 577-578 of AAV2.5T.

3. A non-naturally-occurring modified adeno-associated virus (AAV) capsid protein, comprising one or more amino acid modification that confers heparan sulfate binding to the capsid protein, wherein the AAV is AAV2.5T, and wherein at least one of the one or more amino acid modifications comprises:
  (a) a S576R point mutation;
  (b) a T579R point mutation;
  (c) a substitution of amino acid residues 576-579 or 576-581 with the following amino acid residues: RGNRQA (SEQ ID NO:5);
  (d) a substitution of amino acid residues 576-581 with the following amino acid residues: RGNRQAAP (SEQ ID NO:6);
  (e) a substitution of amino acid residues 573-579, 573-581 or 573-584 with the following amino acid residues: NLQRGNRQAATA (SEQ ID NO:7); or
  (f) a substitution of amino acid residues 573-581 or 573-584 with the following amino acid residues: NLQRGNRQAATAAP (SEQ ID NO:8).

4. The modified AAV2.5T/7m8 capsid protein claim 1, wherein at least one of the one or more amino acid modifications comprises:
  (a) a point mutation corresponding to a S576R point mutation in AAV2.5T;
  (b) a point mutation corresponding to a T579R point mutation in AAV2.5T;
  (c) a substitution corresponding to a substitution of amino acid residues 576-579 or 576-581 in AAV2.5T with the following amino acid residues: RGNRQA (SEQ ID NO:5);
  (d) a substitution corresponding to a substitution of amino acid residues 576-581 in AAV2.5T with the following amino acid residues: RGNRQAAP (SEQ ID NO:6);
  (e) a substitution corresponding to a substitution of amino acid residues 573-579, 573-581, 573-583, 573-584, 576-579, 576-581, 576-583 or 576-584 in AAV2.5T with the following amino acid residues: NLQRGNRQAATA (SEQ ID NO:7); or (f) a substitution corresponding to a substitution of amino acid residues 576-581, 576-583, 576-584, 573-583 or 573-584 in AAV2.5T with the following amino acid residues: NLQRGNRQAATAAP (SEQ ID NO:8).

5. The modified AAV2.5T/7m8 capsid protein of claim 4, comprising a capsid sequence set forth in any of SEQ ID NOs:1-3.

6. The modified AAV2.5T/7m8 capsid protein of claim 4, comprising a capsid sequence having at least 90% sequence identity to SEQ ID NO: 1, and further comprising the sequence set forth in SEQ ID NO: 61.

7. The modified AAV2.5T/7m8 capsid protein of claim 4, comprising a capsid sequence having at least 90% sequence identity to SEQ ID NO: 2, and further comprising the sequence set forth in SEQ ID NO: 68.

8. The modified AAV2.5T/7m8 capsid protein of claim 4, comprising a capsid sequence having at least 90% sequence identity to SEQ ID NO: 3, and further comprising the sequence set forth in SEQ ID NO: 20.

9. The modified AAV2.5T/7m8 capsid protein of claim 4, wherein the capsid protein is an AAV2.5T/7m8(+3), further comprising the following amino acid modifications:
   (a) a point mutation corresponding to a S576R point mutation in AAV2.5T; and
   (b) a point mutation corresponding to a T579R point mutation in AAV2.5T.

10. The modified AAV2.5T/7m8 capsid protein of claim 4, wherein the capsid protein is an AAV2.5T/7m8(−12), further comprising a substitution corresponding to a substitution of amino acid residues 576-581, 576-583, 576-584, 573-583 or 573-584 in AAV2.5T with the following amino acid residues: NLQRGNRQAATAAP (SEQ ID NO:8).

11. The modified AAV2.5T/7m8 capsid protein of claim 10, wherein the capsid protein is an AAV2.5T/7m8(−12), further comprising a substitution corresponding to a substitution of amino acid residues 576-581 in AAV2.5T with the following amino acid residues: NLQRGNRQAATAAP (SEQ ID NO:8).

12. The modified AAV2.5T/7m8 capsid protein of claim 4, wherein the capsid protein is an AAV2.5T/7m8(−3), further comprising a substitution corresponding to a substitution of amino acid residues 573-579, 573-581, 573-583, 573-584, 576-579, 576-581, 576-583 or 576-584 in AAV2.5T with the following amino acid residues: NLQRGNRQAATA (SEQ ID NO:7).

13. The modified AAV2.5T/7m8 capsid protein of claim 12, wherein the capsid protein is an AAV2.5T/7m8(−3), further comprising a substitution corresponding to a substitution of amino acid residues 573-584 in AAV2.5T with the following amino acid residues: NLQRGNRQAATA (SEQ ID NO:7).

* * * * *

SEQUENCE LISTING

<160> NUMBER OF SEQ ID NOS: 76

<210> SEQ ID NO 1
<211> LENGTH: 735
<212> TYPE: PRT
<213> ORGANISM: Artificial Sequence
<220> FEATURE:
<223> OTHER INFORMATION: Made in Lab - Altered AAV capsid protein sequence

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

```
Cys Leu Pro Ala Phe Pro Pro Gln Val Phe Thr Leu Pro Gln Tyr Gly
            355                 360                 365

Tyr Ala Thr Leu Asn Arg Asp Asn Thr Glu Asn Pro Thr Glu Arg Ser
370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Arg
                565                 570                 575

Ser Thr Arg Leu Ala Leu Gly Glu Thr Thr Arg Pro Ala Ala Pro Thr
            580                 585                 590

Thr Gly Thr Tyr Asn Leu Gln Glu Ile Val Pro Gly Ser Val Trp Met
        595                 600                 605

Glu Arg Asp Val Tyr Leu Gln Gly Pro Ile Trp Ala Lys Ile Pro Glu
610                 615                 620

Thr Gly Ala His Phe His Pro Ser Pro Ala Met Gly Gly Phe Gly Leu
625                 630                 635                 640

Lys His Pro Pro Pro Met Met Leu Ile Lys Asn Thr Pro Val Pro Gly
                645                 650                 655

Asn Ile Thr Ser Phe Ser Asp Val Pro Val Ser Ser Phe Ile Thr Gln
            660                 665                 670

Tyr Ser Thr Gly Gln Val Thr Val Glu Met Glu Trp Glu Leu Lys Lys
        675                 680                 685

Glu Asn Ser Lys Arg Trp Asn Pro Glu Ile Gln Tyr Thr Asn Asn Tyr
690                 695                 700

Asn Asp Pro Gln Phe Val Asp Phe Ala Pro Asp Ser Thr Gly Glu Tyr
705                 710                 715                 720

Arg Thr Thr Arg Pro Ile Gly Thr Arg Tyr Leu Thr Arg Pro Leu
                725                 730                 735
```

<210> SEQ ID NO 2
<211> LENGTH: 743
<212> TYPE: PRT
<213> ORGANISM: Artificial Sequence
<220> FEATURE:
<223> OTHER INFORMATION: Made in Lab - Altered AAV capsid protein -continued sequence

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Gly Ala Lys Thr Ala Pro Thr Gly Lys Arg
    130                 135                 140

Ile Asp Asp His Phe Pro Lys Arg Lys Lys Ala Arg Thr Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

```
Asn Asn Phe Glu Phe Thr Tyr Asn Phe Glu Val Pro Phe His Ser
            405                 410                 415

Ser Phe Ala Pro Ser Gln Asn Leu Phe Lys Leu Ala Asn Pro Leu Val
        420                 425                 430

Asp Gln Tyr Leu Tyr Arg Phe Val Ser Thr Asn Asn Thr Gly Gly Val
            435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Leu Ala
                565                 570                 575

Leu Gly Glu Thr Thr Arg Pro Ala Gln Asn Leu Gln Arg Gly Asn Arg
            580                 585                 590

Gln Ala Ala Thr Ala Ala Pro Thr Thr Gly Thr Tyr Asn Leu Gln Glu
        595                 600                 605

Ile Val Pro Gly Ser Val Trp Met Glu Arg Asp Val Tyr Leu Gln Gly
    610                 615                 620

Pro Ile Trp Ala Lys Ile Pro Glu Thr Gly Ala His Phe His Pro Ser
625                 630                 635                 640

Pro Ala Met Gly Gly Phe Gly Leu Lys His Pro Pro Pro Met Met Leu
                645                 650                 655

Ile Lys Asn Thr Pro Val Pro Gly Asn Ile Thr Ser Phe Ser Asp Val
            660                 665                 670

Pro Val Ser Ser Phe Ile Thr Gln Tyr Ser Thr Gly Gln Val Thr Val
        675                 680                 685

Glu Met Glu Trp Glu Leu Lys Lys Glu Asn Ser Lys Arg Trp Asn Pro
    690                 695                 700

Glu Ile Gln Tyr Thr Asn Asn Tyr Asn Asp Pro Gln Phe Val Asp Phe
705                 710                 715                 720

Ala Pro Asp Ser Thr Gly Glu Tyr Arg Thr Thr Arg Pro Ile Gly Thr
                725                 730                 735

Arg Tyr Leu Thr Arg Pro Leu
            740

<210> SEQ ID NO 3
<211> LENGTH: 735
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 3

Met Ala Ala Asp Gly Tyr Leu Pro Asp Trp Leu Glu Asp Thr Leu Ser
1               5                   10                  15
```

Glu Gly Ile Arg Gln Trp Trp Lys Leu Lys Pro Gly Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Val Leu Glu Pro
         115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                 165                 170                 175

Gln Gln Leu Gln Ile Pro Ala Gln Pro Ala Ser Ser Leu Gly Ala Asp
             180                 185                 190

Thr Met Ser Ala Gly Gly Gly Pro Leu Gly Asp Asn Asn Gln Gly
         195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                 245                 250                 255

Asp Gly Ser Asn Ala Asn Ala Tyr Phe Gly Tyr Ser Thr Pro Trp Gly
             260                 265                 270

Tyr Phe Asp Phe Asn Arg Phe His Ser His Trp Ser Pro Arg Asp Trp
         275                 280                 285

Gln Arg Leu Ile Asn Asn Tyr Trp Gly Phe Arg Pro Arg Ser Leu Arg
290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                 325                 330                 335

Asp Asp Asp Tyr Gln Leu Pro Tyr Val Val Gly Asn Gly Thr Glu Gly
             340                 345                 350

Cys Leu Pro Ala Phe Pro Pro Gln Val Phe Thr Leu Pro Gln Tyr Gly
         355                 360                 365

Tyr Ala Thr Leu Asn Arg Asp Asn Thr Glu Asn Pro Thr Glu Arg Ser
370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                 405                 410                 415

Ser Phe Ala Pro Ser Gln Asn Leu Phe Lys Leu Ala Asn Pro Leu Val
             420                 425                 430

```
Asp Gln Tyr Leu Tyr Arg Phe Val Ser Thr Asn Asn Thr Gly Gly Val
            435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Leu Gln Arg
                565                 570                 575

Gly Leu Ala Leu Gly Glu Thr Thr Arg Pro Ala Asn Arg Gln Ala Ala
            580                 585                 590

Thr Ala Thr Tyr Asn Leu Gln Glu Ile Val Pro Gly Ser Val Trp Met
        595                 600                 605

Glu Arg Asp Val Tyr Leu Gln Gly Pro Ile Trp Ala Lys Ile Pro Glu
            610                 615                 620

Thr Gly Ala His Phe His Pro Ser Pro Ala Met Gly Gly Phe Gly Leu
625                 630                 635                 640

Lys His Pro Pro Met Met Leu Ile Lys Asn Thr Pro Val Pro Gly
                645                 650                 655

Asn Ile Thr Ser Phe Ser Asp Val Pro Val Ser Ser Phe Ile Thr Gln
            660                 665                 670

Tyr Ser Thr Gly Gln Val Thr Val Glu Met Glu Trp Glu Leu Lys Lys
            675                 680                 685

Glu Asn Ser Lys Arg Trp Asn Pro Glu Ile Gln Tyr Thr Asn Asn Tyr
690                 695                 700

Asn Asp Pro Gln Phe Val Asp Phe Ala Pro Asp Ser Thr Gly Glu Tyr
705                 710                 715                 720

Arg Thr Thr Arg Pro Ile Gly Thr Arg Tyr Leu Thr Arg Pro Leu
                725                 730                 735

<210> SEQ ID NO 4
<211> LENGTH: 10
<212> TYPE: PRT
<213> ORGANISM: Artificial Sequence
<220> FEATURE:
<223> OTHER INFORMATION: Made in Lab - amino acid substitution fragment

<400> SEQUENCE: 4

Leu Ala Leu Gly Glu Thr Thr Arg Pro Ala
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Made in Lab - amino acid substitution fragment

<400> SEQUENCE: 5
```

```
Arg Gly Asn Arg Gln Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Made in Lab - amino acid substitution fragment

<400> SEQUENCE: 6

Arg Gly Asn Arg Gln Ala Ala Pro
1               5

<210> SEQ ID NO 7
<211> LENGTH: 12
<212> TYPE: PRT
<213> ORGANISM: Artificial Sequence
<220> FEATURE:
<223> OTHER INFORMATION: Made in Lab - amino acid substitution fragment

<400> SEQUENCE: 7

Asn Leu Gln Arg Gly Asn Arg Gln Ala Ala Thr Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Made in Lab - amino acid substitution fragment

<400> SEQUENCE: 8

Asn Leu Gln Arg Gly Asn Arg Gln Ala Ala Thr Ala Ala Pro
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Made in Lab - amino acid substitution fragment

<400> SEQUENCE: 9

Thr Asn Gln Asn Leu Gln Arg Gly Asn Arg Gln Ala Ala Thr Ala
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Made in Lab - amino acid substitution fragment

<400> SEQUENCE: 10

Thr Asn Gln Asn Leu Gln Arg Gly Asn Arg Gln Ala Ala Thr Ala Ala
1               5                   10                  15

Pro

<210> SEQ ID NO 11
<211> LENGTH: 7
<212> TYPE: PRT
<213> ORGANISM: Artificial Sequence
<220> FEATURE:
<223> OTHER INFORMATION: Made in Lab - amino acid substitution fragment
```

```
<400> SEQUENCE: 11

Leu Gly Glu Thr Thr Arg Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Made in Lab - amino acid substitution fragment

<400> SEQUENCE: 12

Gln Arg Gly Asn Arg Gln Ala
1               5

<210> SEQ ID NO 13
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 13

Asn Leu Gln Arg Gly Asn Arg Gln Ala Ala Thr Ala Leu Ala Leu Gly
1               5                   10                  15

Glu Thr Thr Arg Pro Ala
            20

<210> SEQ ID NO 14
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 14

Asn Leu Gln Arg Gly Asn Arg Gln Ala Ala Thr Leu Ala Leu Gly Glu
1               5                   10                  15

Thr Thr Arg Pro Ala Ala
            20

<210> SEQ ID NO 15
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 15

Asn Leu Gln Arg Gly Asn Arg Gln Ala Ala Leu Ala Leu Gly Glu Thr
1               5                   10                  15

Thr Arg Pro Ala Thr Ala
            20

<210> SEQ ID NO 16
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 16

Asn Leu Gln Arg Gly Asn Arg Gln Ala Leu Ala Leu Gly Glu Thr Thr
1               5                   10                  15
```

Arg Pro Ala Ala Thr Ala
            20

<210> SEQ ID NO 17
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 17

Asn Leu Gln Arg Gly Asn Arg Gln Leu Ala Leu Gly Glu Thr Thr Arg
1               5                   10                  15

Pro Ala Ala Ala Thr Ala
            20

<210> SEQ ID NO 18
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 18

Asn Leu Gln Arg Gly Asn Arg Leu Ala Leu Gly Glu Thr Thr Arg Pro
1               5                   10                  15

Ala Gln Ala Ala Thr Ala
            20

<210> SEQ ID NO 19
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 19

Asn Leu Gln Arg Gly Asn Leu Ala Leu Gly Glu Thr Thr Arg Pro Ala
1               5                   10                  15

Arg Gln Ala Ala Thr Ala
            20

<210> SEQ ID NO 20
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 20

Asn Leu Gln Arg Gly Leu Ala Leu Gly Glu Thr Thr Arg Pro Ala Asn
1               5                   10                  15

Arg Gln Ala Ala Thr Ala
            20

<210> SEQ ID NO 21
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 21

Asn Leu Gln Arg Leu Ala Leu Gly Glu Thr Thr Arg Pro Ala Gly Asn
1               5                   10                  15

Arg Gln Ala Ala Thr Ala
            20

<210> SEQ ID NO 22
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 22

Asn Leu Gln Leu Ala Leu Gly Glu Thr Thr Arg Pro Ala Arg Gly Asn
1               5                   10                  15

Arg Gln Ala Ala Thr Ala
            20

<210> SEQ ID NO 23
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 23

Asn Leu Leu Ala Leu Gly Glu Thr Thr Arg Pro Ala Gln Arg Gly Asn
1               5                   10                  15

Arg Gln Ala Ala Thr Ala
            20

<210> SEQ ID NO 24
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 24

Asn Leu Ala Leu Gly Glu Thr Thr Arg Pro Ala Leu Gln Arg Gly Asn
1               5                   10                  15

Arg Gln Ala Ala Thr Ala
            20

<210> SEQ ID NO 25
<211> LENGTH: 22
<212> TYPE: PRT
<213> ORGANISM: Artificial Sequence
<220> FEATURE:
<223> OTHER INFORMATION: Made in Lab - amino acid substitution fragment

<400> SEQUENCE: 25

Leu Ala Leu Gly Glu Thr Thr Arg Pro Ala Asn Leu Gln Arg Gly Asn
1               5                   10                  15

Arg Gln Ala Ala Thr Ala
            20

<210> SEQ ID NO 26
<211> LENGTH: 6
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 26

```
Ser Ser Thr Thr Ala Pro
1               5
```

<210> SEQ ID NO 27
<211> LENGTH: 4
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 27

```
Ser Ser Thr Thr
1
```

<210> SEQ ID NO 28
<211> LENGTH: 745
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 28

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Leu Gly Glu
            580                 585                 590

Thr Thr Arg Pro Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
```

```
                690             695             700
Asn Pro Glu Ile Gln Tyr Thr Ser Asn Tyr Asn Lys Ser Val Asn Val
705             710             715                 720

Asp Phe Thr Val Asp Thr Asn Gly Val Tyr Ser Glu Pro Arg Pro Ile
                725             730             735

Gly Thr Arg Tyr Leu Thr Arg Asn Leu
            740             745

<210> SEQ ID NO 29
<211> LENGTH: 725
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 29

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
130             135                 140

Ile Asp Asp His Phe Pro Lys Arg Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300
```

```
Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
            325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
            355                 360                 365

Tyr Ala Thr Leu Asn Arg Asp Asn Thr Glu Asn Pro Thr Glu Arg Ser
        370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
530                 535                 540

Glu Gly Asn Met Leu Ile Thr Ser Glu Ser Thr Gln Pro Val Asn
545                 550                 555                 560

Arg Val Ala Tyr Asn Val Gly Gly Gln Met Ala Thr Asn Asn Gln Ser
                565                 570                 575

Ser Thr Arg Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
```

-continued

725

<210> SEQ ID NO 30
<211> LENGTH: 725
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 30

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
            355                 360                 365

Tyr Ala Thr Leu Asn Arg Asp Asn Thr Glu Asn Pro Thr Glu Arg Ser
370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
                420                 425                 430

Asp Gln Tyr Leu Tyr Arg Phe Val Ser Thr Asn Asn Thr Gly Gly Val
            435                 440                 445

Gln Phe Asn Lys Asn Leu Ala Gly Arg Tyr Ala Asn Thr Tyr Lys Asn
        450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
                500                 505                 510

Thr Asn Asn Leu Gln Gly Ser Asn Thr Tyr Ala Leu Glu Asn Thr Met
            515                 520                 525

Ile Phe Asn Ser Gln Pro Ala Asn Pro Gly Thr Thr Ala Thr Tyr Leu
        530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Arg
                565                 570                 575

Ser Thr Arg Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
                660                 665                 670

Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
        690                 695                 700

Asp Ser Thr Gly Glu Tyr Arg Thr Thr Arg Pro Ile Gly Thr Arg Tyr
705                 710                 715                 720

Leu Thr Arg Pro Leu
            725

<210> SEQ ID NO 31
<211> LENGTH: 725
<212> TYPE: PRT
<213> ORGANISM: Artificial Sequence
<220> FEATURE:
<223> OTHER INFORMATION: Made in Lab - Altered AAV capsid protein sequence

<400> SEQUENCE: 31

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400
```

-continued

Asn Asn Phe Glu Phe Thr Tyr Asn Phe Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Arg
                565                 570                 575

Gly Asn Arg Gln Ala Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asn Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 32
<211> LENGTH: 725
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 32

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

```
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
     50                  55                  60
Val Asn Glu Ala Asp Ala Ala Leu Glu His Asp Lys Ala Tyr Asp
 65              70                  75                  80
Arg Gln Leu Asp Ser Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
                115                 120                 125
Phe Gly Leu Val Glu Glu Gly Ala Lys Thr Ala Pro Thr Gly Lys Arg
            130                 135                 140
Ile Asp Asp His Phe Pro Lys Arg Lys Lys Ala Arg Thr Glu Glu Asp
145                 150                 155                 160
Ser Lys Pro Ser Thr Ser Ser Asp Ala Glu Ala Gly Pro Ser Gly Ser
                165                 170                 175
Gln Gln Leu Gln Ile Pro Ala Gln Pro Ala Ser Ser Leu Gly Ala Asp
            180                 185                 190
Thr Met Ser Ala Gly Gly Gly Pro Leu Gly Asp Asn Asn Gln Gly
            195                 200                 205
Ala Asp Gly Val Gly Asn Ala Ser Gly Asp Trp His Cys Asp Ser Thr
            210                 215                 220
Trp Met Gly Asp Arg Val Val Thr Lys Ser Thr Arg Thr Trp Val Leu
225                 230                 235                 240
Pro Ser Tyr Asn Asn His Gln Tyr Arg Glu Ile Lys Ser Gly Ser Val
                245                 250                 255
Asp Gly Ser Asn Ala Asn Ala Tyr Phe Gly Tyr Ser Thr Pro Trp Gly
                260                 265                 270
Tyr Phe Asp Phe Asn Arg Phe His Ser His Trp Ser Pro Arg Asp Trp
            275                 280                 285
Gln Arg Leu Ile Asn Asn Tyr Trp Gly Phe Arg Pro Arg Ser Leu Arg
            290                 295                 300
Val Lys Ile Phe Asn Ile Gln Val Lys Glu Val Thr Val Gln Asp Ser
305                 310                 315                 320
Thr Thr Thr Ile Ala Asn Asn Leu Thr Ser Thr Val Gln Val Phe Thr
                325                 330                 335
Asp Asp Asp Tyr Gln Leu Pro Tyr Val Val Gly Asn Gly Thr Glu Gly
                340                 345                 350
Cys Leu Pro Ala Phe Pro Pro Gln Val Phe Thr Leu Pro Gln Tyr Gly
            355                 360                 365
Tyr Ala Thr Leu Asn Arg Asp Asn Thr Glu Asn Pro Thr Glu Arg Ser
            370                 375                 380
Ser Phe Phe Cys Leu Glu Tyr Phe Pro Ser Lys Met Leu Arg Thr Gly
385                 390                 395                 400
Asn Asn Phe Glu Phe Thr Tyr Asn Phe Glu Glu Val Pro Phe His Ser
                405                 410                 415
Ser Phe Ala Pro Ser Gln Asn Leu Phe Lys Leu Ala Asn Pro Leu Val
            420                 425                 430
Asp Gln Tyr Leu Tyr Arg Phe Val Ser Thr Asn Asn Thr Gly Gly Val
            435                 440                 445
```

-continued

```
Gln Phe Asn Lys Asn Leu Ala Gly Arg Tyr Ala Asn Thr Tyr Lys Asn
    450                 455                 460
Trp Phe Pro Gly Pro Met Gly Arg Thr Gln Gly Trp Asn Leu Gly Ser
465                 470                 475                 480
Gly Val Asn Arg Ala Ser Val Ser Ala Phe Ala Thr Thr Asn Arg Met
                485                 490                 495
Glu Leu Glu Gly Ala Ser Tyr Gln Val Pro Gln Pro Asn Gly Met
            500                 505                 510
Thr Asn Asn Leu Gln Gly Ser Asn Thr Tyr Ala Leu Glu Asn Thr Met
            515                 520                 525
Ile Phe Asn Ser Gln Pro Ala Asn Pro Gly Thr Thr Ala Thr Tyr Leu
    530                 535                 540
Glu Gly Asn Met Leu Ile Thr Ser Glu Ser Glu Thr Gln Pro Val Asn
545                 550                 555                 560
Arg Val Ala Tyr Asn Val Gly Gly Gln Met Ala Thr Asn Leu Gln Arg
                565                 570                 575
Gly Asn Arg Gln Ala Ala Thr Ala Thr Tyr Asn Leu Gln Glu Ile Val
            580                 585                 590
Pro Gly Ser Val Trp Met Glu Arg Asp Val Tyr Leu Gln Gly Pro Ile
            595                 600                 605
Trp Ala Lys Ile Pro Glu Thr Gly Ala His Phe His Pro Ser Pro Ala
    610                 615                 620
Met Gly Gly Phe Gly Leu Lys His Pro Pro Met Met Leu Ile Lys
625                 630                 635                 640
Asn Thr Pro Val Pro Gly Asn Ile Thr Ser Phe Ser Asp Val Pro Val
                645                 650                 655
Ser Ser Phe Ile Thr Gln Tyr Ser Thr Gly Gln Val Thr Val Glu Met
            660                 665                 670
Glu Trp Glu Leu Lys Lys Glu Asn Ser Lys Arg Trp Asn Pro Glu Ile
            675                 680                 685
Gln Tyr Thr Asn Asn Tyr Asn Asp Pro Gln Phe Val Asp Phe Ala Pro
    690                 695                 700
Asp Ser Thr Gly Glu Tyr Arg Thr Thr Arg Pro Ile Gly Thr Arg Tyr
705                 710                 715                 720
Leu Thr Arg Pro Leu
                725

<210> SEQ ID NO 33
<211> LENGTH: 735
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 33

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
```

```
Arg Gln Leu Asp Ser Gly Asp Asn Pro Tyr Leu Lys Tyr Asn His Ala
                85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Val Leu Glu Pro
        115             120             125

Phe Gly Leu Val Glu Glu Gly Ala Lys Thr Ala Pro Thr Gly Lys Arg
    130             135             140

Ile Asp Asp His Phe Pro Lys Arg Lys Lys Ala Arg Thr Glu Glu Asp
145             150             155             160

Ser Lys Pro Ser Thr Ser Ser Asp Ala Glu Ala Gly Pro Ser Gly Ser
            165             170             175

Gln Gln Leu Gln Ile Pro Ala Gln Pro Ala Ser Ser Leu Gly Ala Asp
        180             185             190

Thr Met Ser Ala Gly Gly Gly Pro Leu Gly Asp Asn Asn Gln Gly
    195             200             205

Ala Asp Gly Val Gly Asn Ala Ser Gly Asp Trp His Cys Asp Ser Thr
210             215             220

Trp Met Gly Asp Arg Val Val Thr Lys Ser Thr Arg Thr Trp Val Leu
225             230             235             240

Pro Ser Tyr Asn Asn His Gln Tyr Arg Glu Ile Lys Ser Gly Ser Val
            245             250             255

Asp Gly Ser Asn Ala Asn Ala Tyr Phe Gly Tyr Ser Thr Pro Trp Gly
            260             265             270

Tyr Phe Asp Phe Asn Arg Phe His Ser His Trp Ser Pro Arg Asp Trp
    275             280             285

Gln Arg Leu Ile Asn Asn Tyr Trp Gly Phe Arg Pro Arg Ser Leu Arg
    290             295             300

Val Lys Ile Phe Asn Ile Gln Val Lys Glu Val Thr Val Gln Asp Ser
305             310             315             320

Thr Thr Thr Ile Ala Asn Asn Leu Thr Ser Thr Val Gln Val Phe Thr
            325             330             335

Asp Asp Asp Tyr Gln Leu Pro Tyr Val Val Gly Asn Gly Thr Glu Gly
            340             345             350

Cys Leu Pro Ala Phe Pro Pro Gln Val Phe Thr Leu Pro Gln Tyr Gly
    355             360             365

Tyr Ala Thr Leu Asn Arg Asp Asn Thr Glu Asn Pro Thr Glu Arg Ser
    370             375             380

Ser Phe Phe Cys Leu Glu Tyr Phe Pro Ser Lys Met Leu Arg Thr Gly
385             390             395             400

Asn Asn Phe Glu Phe Thr Tyr Asn Phe Glu Glu Val Pro Phe His Ser
            405             410             415

Ser Phe Ala Pro Ser Gln Asn Leu Phe Lys Leu Ala Asn Pro Leu Val
            420             425             430

Asp Gln Tyr Leu Tyr Arg Phe Val Ser Thr Asn Asn Thr Gly Gly Val
        435             440             445

Gln Phe Asn Lys Asn Leu Ala Gly Arg Tyr Ala Asn Thr Tyr Lys Asn
    450             455             460

Trp Phe Pro Gly Pro Met Gly Arg Thr Gln Gly Trp Asn Leu Gly Ser
465             470             475             480

Gly Val Asn Arg Ala Ser Val Ser Ala Phe Ala Thr Thr Asn Arg Met
            485             490             495
```

-continued

```
Glu Leu Glu Gly Ala Ser Tyr Gln Val Pro Pro Gln Pro Asn Gly Met
                500                 505                 510

Thr Asn Asn Leu Gln Gly Ser Asn Thr Tyr Ala Leu Glu Asn Thr Met
            515                 520                 525

Ile Phe Asn Ser Gln Pro Ala Asn Pro Gly Thr Thr Ala Thr Tyr Leu
        530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Arg
                565                 570                 575

Gly Leu Ala Leu Gly Glu Thr Thr Arg Pro Ala Asn Arg Gln Ala Thr
            580                 585                 590

Thr Gly Thr Tyr Asn Leu Gln Glu Ile Val Pro Gly Ser Val Trp Met
        595                 600                 605

Glu Arg Asp Val Tyr Leu Gln Gly Pro Ile Trp Ala Lys Ile Pro Glu
610                 615                 620

Thr Gly Ala His Phe His Pro Ser Pro Ala Met Gly Gly Phe Gly Leu
625                 630                 635                 640

Lys His Pro Pro Met Met Leu Ile Lys Asn Thr Pro Val Pro Gly
                645                 650                 655

Asn Ile Thr Ser Phe Ser Asp Val Pro Val Ser Ser Phe Ile Thr Gln
            660                 665                 670

Tyr Ser Thr Gly Gln Val Thr Val Glu Met Glu Trp Glu Leu Lys Lys
        675                 680                 685

Glu Asn Ser Lys Arg Trp Asn Pro Glu Ile Gln Tyr Thr Asn Asn Tyr
690                 695                 700

Asn Asp Pro Gln Phe Val Asp Phe Ala Pro Asp Ser Thr Gly Glu Tyr
705                 710                 715                 720

Arg Thr Thr Arg Pro Ile Gly Thr Arg Tyr Leu Thr Arg Pro Leu
                725                 730                 735

<210> SEQ ID NO 34
<211> LENGTH: 735
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 34

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Phe Gly Leu Val Glu Glu Gly Ala Lys Thr Ala Pro Thr Gly Lys Arg
        130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
                180                 185                 190

Thr Met Ser Ala Gly Gly Gly Pro Leu Gly Asp Asn Asn Gln Gly
                195                 200                 205

Ala Asp Gly Val Gly Asn Ala Ser Gly Asp Trp His Cys Asp Ser Thr
        210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
                260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
        290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
                340                 345                 350

Cys Leu Pro Ala Phe Pro Pro Gln Val Phe Thr Leu Pro Gln Tyr Gly
                355                 360                 365

Tyr Ala Thr Leu Asn Arg Asp Asn Thr Glu Asn Pro Thr Glu Arg Ser
        370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
                420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
        450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
                500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
530                 535                 540
```

Glu Gly Asn Met Leu Ile Thr Ser Glu Ser Thr Gln Pro Val Asn
545                 550                 555                 560

Arg Val Ala Tyr Asn Val Gly Gly Gln Met Ala Thr Asn Leu Gln Arg
            565                 570                 575

Gly Asn Leu Ala Leu Gly Glu Thr Thr Arg Pro Ala Arg Gln Ala Ala
            580                 585                 590

Thr Ala Thr Tyr Asn Leu Gln Glu Ile Val Pro Gly Ser Val Trp Met
            595                 600                 605

Glu Arg Asp Val Tyr Leu Gln Gly Pro Ile Trp Ala Lys Ile Pro Glu
            610                 615                 620

Thr Gly Ala His Phe His Pro Ser Pro Ala Met Gly Gly Phe Gly Leu
625                 630                 635                 640

Lys His Pro Pro Pro Met Met Leu Ile Lys Asn Thr Pro Val Pro Gly
                    645                 650                 655

Asn Ile Thr Ser Phe Ser Asp Val Pro Val Ser Ser Phe Ile Thr Gln
                660                 665                 670

Tyr Ser Thr Gly Gln Val Thr Val Glu Met Glu Trp Glu Leu Lys Lys
            675                 680                 685

Glu Asn Ser Lys Arg Trp Asn Pro Glu Ile Gln Tyr Thr Asn Asn Tyr
            690                 695                 700

Asn Asp Pro Gln Phe Val Asp Phe Ala Pro Asp Ser Thr Gly Glu Tyr
705                 710                 715                 720

Arg Thr Thr Arg Pro Ile Gly Thr Arg Tyr Leu Thr Arg Pro Leu
                    725                 730                 735

<210> SEQ ID NO 35
<211> LENGTH: 737
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 35

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65              70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

```
Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
                260                 265                 270

Tyr Phe Asp Phe Asn Arg Phe His Ser His Trp Ser Pro Arg Asp Trp
            275                 280                 285

Gln Arg Leu Ile Asn Asn Tyr Trp Gly Phe Arg Pro Arg Ser Leu Arg
            290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
            355                 360                 365

Tyr Ala Thr Leu Asn Arg Asp Asn Thr Glu Asn Pro Thr Glu Arg Ser
            370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
                420                 425                 430

Asp Gln Tyr Leu Tyr Arg Phe Val Ser Thr Asn Asn Thr Gly Gly Val
            435                 440                 445

Gln Phe Asn Lys Asn Leu Ala Gly Arg Tyr Ala Asn Thr Tyr Lys Asn
            450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
            515                 520                 525

Ile Phe Asn Ser Gln Pro Ala Asn Pro Gly Thr Thr Ala Thr Tyr Leu
            530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Leu Ala
                565                 570                 575

Leu Gly Glu Thr Thr Arg Pro Ala Gln Arg Gly Asn Arg Gln Ala Ala
            580                 585                 590
```

```
Pro Thr Thr Gly Thr Tyr Asn Leu Gln Glu Ile Val Pro Gly Ser Val
            595                 600                 605

Trp Met Glu Arg Asp Val Tyr Leu Gln Gly Pro Ile Trp Ala Lys Ile
610                 615                 620

Pro Glu Thr Gly Ala His Phe His Pro Ser Pro Ala Met Gly Phe
625                 630                 635                 640

Gly Leu Lys His Pro Pro Met Met Leu Ile Lys Asn Thr Pro Val
            645                 650                 655

Pro Gly Asn Ile Thr Ser Phe Ser Asp Val Pro Val Ser Phe Ile
            660                 665                 670

Thr Gln Tyr Ser Thr Gly Gln Val Thr Val Glu Met Glu Trp Glu Leu
            675                 680                 685

Lys Lys Glu Asn Ser Lys Arg Trp Asn Pro Glu Ile Gln Tyr Thr Asn
690                 695                 700

Asn Tyr Asn Asp Pro Gln Phe Val Asp Phe Ala Pro Asp Ser Thr Gly
705                 710                 715                 720

Glu Tyr Arg Thr Thr Arg Pro Ile Gly Thr Arg Tyr Leu Thr Arg Pro
                725                 730                 735

Leu

<210> SEQ ID NO 36
<211> LENGTH: 118
<212> TYPE: PRT
<213> ORGANISM: Artificial Sequence
<220> FEATURE:
<223> OTHER INFORMATION: Made in Lab - synthetic antibody construct

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu
        115

<210> SEQ ID NO 37
<211> LENGTH: 110
<212> TYPE: PRT
<213> ORGANISM: Artificial Sequence
<220> FEATURE:
<223> OTHER INFORMATION: Made in Lab - synthetic antibody construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30
```

```
Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val
            100                 105                 110

<210> SEQ ID NO 38
<211> LENGTH: 118
<212> TYPE: PRT
<213> ORGANISM: Artificial Sequence
<220> FEATURE:
<223> OTHER INFORMATION: Made in Lab - synthetic antibody construct

<400> SEQUENCE: 38

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                      55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Tyr Gly Thr Ser His Trp Tyr Phe Asp Val
            100                 105                 110

Trp Gly Gln Gly Thr Leu
        115

<210> SEQ ID NO 39
<211> LENGTH: 110
<212> TYPE: PRT
<213> ORGANISM: Artificial Sequence
<220> FEATURE:
<223> OTHER INFORMATION: Made in Lab - synthetic antibody construct

<400> SEQUENCE: 39

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val
            100                 105                 110
```

```
<210> SEQ ID NO 40
<211> LENGTH: 458
<212> TYPE: PRT
<213> ORGANISM: Artificial Sequence
<220> FEATURE:
<223> OTHER INFORMATION: Made in Lab - synthetic antibody construct

<400> SEQUENCE: 40

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365
```

```
Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
        450                 455

<210> SEQ ID NO 41
<211> LENGTH: 725
<212> TYPE: PRT
<213> ORGANISM: Adeno-associated virus-5

<400> SEQUENCE: 41

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
```

-continued

```
            275                 280                 285
Gln Arg Leu Ile Asn Asn Tyr Trp Gly Phe Arg Pro Arg Ser Leu Arg
        290                 295                 300
Val Lys Ile Phe Asn Ile Gln Val Lys Glu Val Thr Val Gln Asp Ser
305                 310                 315                 320
Thr Thr Thr Ile Ala Asn Asn Leu Thr Ser Thr Val Gln Val Phe Thr
                    325                 330                 335
Asp Asp Asp Tyr Gln Leu Pro Tyr Val Val Gly Asn Gly Thr Glu Gly
            340                 345                 350
Cys Leu Pro Ala Phe Pro Pro Gln Val Phe Thr Leu Pro Gln Tyr Gly
                355                 360                 365
Tyr Ala Thr Leu Asn Arg Asp Asn Thr Glu Asn Pro Thr Glu Arg Ser
        370                 375                 380
Ser Phe Phe Cys Leu Glu Tyr Phe Pro Ser Lys Met Leu Arg Thr Gly
385                 390                 395                 400
Asn Asn Phe Glu Phe Thr Tyr Asn Phe Glu Glu Val Pro Phe His Ser
                    405                 410                 415
Ser Phe Ala Pro Ser Gln Asn Leu Phe Lys Leu Ala Asn Pro Leu Val
            420                 425                 430
Asp Gln Tyr Leu Tyr Arg Phe Val Ser Thr Asn Asn Thr Gly Gly Val
                435                 440                 445
Gln Phe Asn Lys Asn Leu Ala Gly Arg Tyr Ala Asn Thr Tyr Lys Asn
        450                 455                 460
Trp Phe Pro Gly Pro Met Gly Arg Thr Gln Gly Trp Asn Leu Gly Ser
465                 470                 475                 480
Gly Val Asn Arg Ala Ser Val Ser Ala Phe Ala Thr Thr Asn Arg Met
                    485                 490                 495
Glu Leu Glu Gly Ala Ser Tyr Gln Val Pro Pro Gln Pro Asn Gly Met
            500                 505                 510
Thr Asn Asn Leu Gln Gly Ser Asn Thr Tyr Ala Leu Glu Asn Thr Met
                515                 520                 525
Ile Phe Asn Ser Gln Pro Ala Asn Pro Gly Thr Thr Ala Thr Tyr Leu
        530                 535                 540
Glu Gly Asn Met Leu Ile Thr Ser Glu Ser Glu Thr Gln Pro Val Asn
545                 550                 555                 560
Arg Val Ala Tyr Asn Val Gly Gly Gln Met Ala Thr Asn Asn Gln Ser
                    565                 570                 575
Ser Thr Thr Ala Pro Thr Thr Gly Thr Tyr Asn Leu Gln Glu Ile Val
            580                 585                 590
Pro Gly Ser Val Trp Met Glu Arg Asp Val Tyr Leu Gln Gly Pro Ile
                595                 600                 605
Trp Ala Lys Ile Pro Glu Thr Gly Ala His Phe His Pro Ser Pro Ala
        610                 615                 620
Met Gly Gly Phe Gly Leu Lys His Pro Pro Met Met Leu Ile Lys
625                 630                 635                 640
Asn Thr Pro Val Pro Gly Asn Ile Thr Ser Phe Ser Asp Val Pro Val
                    645                 650                 655
Ser Ser Phe Ile Thr Gln Tyr Ser Thr Gly Gln Val Thr Val Glu Met
            660                 665                 670
Glu Trp Glu Leu Lys Lys Glu Asn Ser Lys Arg Trp Asn Pro Glu Ile
                675                 680                 685
Gln Tyr Thr Asn Asn Tyr Asn Asp Pro Gln Phe Val Asp Phe Ala Pro
        690                 695                 700
```

```
Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 42
<211> LENGTH: 450
<212> TYPE: PRT
<213> ORGANISM: Artificial Sequence
<220> FEATURE:
<223> OTHER INFORMATION: Made in Lab

<400> SEQUENCE: 42

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Ala Gly Gln Thr Leu His
            35                  40                  45

Leu Gln Cys Arg Gly Glu Ala Ala Met Gln His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335
```

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln
    450

<210> SEQ ID NO 43
<211> LENGTH: 106
<212> TYPE: PRT
<213> ORGANISM: Artificial Sequence
<220> FEATURE:
<223> OTHER INFORMATION: Made in Lab

<400> SEQUENCE: 43

Ile Tyr Ile Phe Ile Ser Asp Thr Gly Arg Pro Phe Val Glu Met Tyr
1               5                   10                  15

Ser Glu Ile Pro Glu Ile Ile His Met Thr Glu Gly Arg Glu Leu Val
            20                  25                  30

Ile Pro Cys Arg Val Thr Ser Pro Asn Ile Thr Val Thr Leu Lys Lys
        35                  40                  45

Phe Pro Leu Asp Thr Leu Ile Pro Asp Gly Lys Arg Ile Ile Trp Asp
    50                  55                  60

Ser Arg Lys Gly Phe Ile Ile Ser Asn Ala Thr Tyr Lys Glu Ile Gly
65                  70                  75                  80

Leu Leu Thr Cys Glu Ala Thr Val Asn Gly His Leu Tyr Lys Thr Asn
                85                  90                  95

Tyr Leu Thr His Arg Gln Thr Asn Thr Ile
            100                 105

<210> SEQ ID NO 44
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 44

Ser Thr Asn Leu Gln Arg Gly Asn Arg Gln Ala Ala Thr Ala Asp
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

```
<400> SEQUENCE: 45

Ala Thr Asn Asn Gln Ser Ser Arg Arg Ala Pro Ala Thr Gly Thr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 46

Ala Thr Asn Asn Gln Ser Ser Thr Thr Ala Pro Thr Thr Gly Thr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 47

Ala Thr Asn Asn Gln Arg Ser Thr Thr Ala Pro Thr Thr Gly Thr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 48

Ala Thr Asn Asn Gln Ser Ser Thr Arg Ala Pro Thr Thr Gly Thr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 49

Ala Thr Asn Asn Gln Arg Ser Thr Arg Ala Pro Thr Thr Gly Thr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 50

Ala Thr Asn Asn Gln Arg Gly Asn Arg Gln Ala Thr Thr Gly Thr
1               5                   10                  15

<210> SEQ ID NO 51
<211> LENGTH: 17
<212> TYPE: PRT
```

```
<213> ORGANISM: Artificial Sequence
<220> FEATURE:
<223> OTHER INFORMATION: Made in Lab - Altered AAV capsid protein
      sequence

<400> SEQUENCE: 51

Ala Thr Asn Asn Gln Arg Gly Asn Arg Gln Ala Ala Pro Thr Thr Gly
1               5                   10                  15

Thr

<210> SEQ ID NO 52
<211> LENGTH: 15
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 52

Ala Thr Asn Leu Gln Arg Gly Asn Arg Gln Ala Ala Thr Ala Thr
1               5                   10                  15

<210> SEQ ID NO 53
<211> LENGTH: 23
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 53

Ala Thr Asn Asn Gln Asn Leu Gln Arg Gly Asn Arg Gln Ala Ala Thr
1               5                   10                  15

Ala Ala Pro Thr Thr Gly Thr
            20

<210> SEQ ID NO 54
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 54

Ser Thr Asn Leu Gln Arg Gly Asn Leu Ala Leu Gly Glu Thr Thr Arg
1               5                   10                  15

Pro Ala Arg Gln Ala Ala Thr Ala Asp
            20                  25

<210> SEQ ID NO 55
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 55

Ala Thr Asn Asn Gln Ser Ser Thr Leu Ala Leu Gly Glu Thr Thr Arg
1               5                   10                  15

Pro Ala Thr Ala Pro Thr Thr Gly Thr
            20                  25

<210> SEQ ID NO 56
```

```
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 56

Ala Thr Asn Asn Gln Ser Ser Thr Thr Leu Ala Leu Gly Glu Thr Thr
1               5                   10                  15

Arg Pro Ala Ala Pro Thr Thr Gly Thr
            20                  25

<210> SEQ ID NO 57
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 57

Ala Thr Asn Asn Gln Ser Ser Leu Ala Leu Gly Glu Thr Thr Arg Pro
1               5                   10                  15

Ala Thr Thr Ala Pro Thr Thr Gly Thr
            20                  25

<210> SEQ ID NO 58
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 58

Ala Thr Asn Asn Gln Ser Leu Ala Leu Gly Glu Thr Thr Arg Pro Ala
1               5                   10                  15

Ser Thr Thr Ala Pro Thr Thr Gly Thr
            20                  25

<210> SEQ ID NO 59
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 59

Ala Thr Asn Asn Gln Leu Ala Leu Gly Glu Thr Thr Arg Pro Ala Ser
1               5                   10                  15

Ser Thr Thr Ala Pro Thr Thr Gly Thr
            20                  25

<210> SEQ ID NO 60
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 60

Ala Thr Asn Asn Leu Ala Leu Gly Glu Thr Thr Arg Pro Ala Gln Ser
1               5                   10                  15
```

Ser Thr Thr Ala Pro Thr Thr Gly Thr
            20                  25

<210> SEQ ID NO 61
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 61

Ala Thr Asn Asn Gln Arg Ser Thr Arg Leu Ala Leu Gly Glu Thr Thr
1               5                   10                  15

Arg Pro Ala Ala Pro Thr Thr Gly Thr
            20                  25

<210> SEQ ID NO 62
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 62

Ala Thr Asn Asn Leu Ala Leu Gly Glu Thr Thr Arg Pro Ala Gln Arg
1               5                   10                  15

Ser Thr Arg Ala Pro Thr Thr Gly Thr
            20                  25

<210> SEQ ID NO 63
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 63

Ala Thr Asn Asn Gln Arg Gly Asn Leu Ala Leu Gly Glu Thr Thr Arg
1               5                   10                  15

Pro Ala Arg Gln Ala Thr Thr Gly Thr
            20                  25

<210> SEQ ID NO 64
<211> LENGTH: 27
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 64

Ala Thr Asn Asn Gln Arg Gly Asn Leu Ala Leu Gly Glu Thr Thr Arg
1               5                   10                  15

Pro Ala Arg Gln Ala Ala Pro Thr Thr Gly Thr
            20                  25

<210> SEQ ID NO 65
<211> LENGTH: 25
<212> TYPE: PRT
<213> ORGANISM: Artificial Sequence
<220> FEATURE:
<223> OTHER INFORMATION: Made in Lab - Altered AAV capsid protein sequence

<400> SEQUENCE: 65

Ala Thr Asn Leu Gln Arg Gly Asn Leu Ala Leu Gly Glu Thr Thr Arg
1               5                   10                  15

Pro Ala Arg Gln Ala Ala Thr Ala Thr
            20                  25

<210> SEQ ID NO 66
<211> LENGTH: 25
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 66

Ala Thr Asn Leu Gln Arg Gly Leu Ala Leu Gly Glu Thr Thr Arg Pro
1               5                   10                  15

Ala Asn Arg Gln Ala Ala Thr Ala Thr
            20                  25

<210> SEQ ID NO 67
<211> LENGTH: 27
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 67

Ala Thr Asn Asn Leu Ala Leu Gly Glu Thr Thr Arg Pro Ala Gln Arg
1               5                   10                  15

Gly Asn Arg Gln Ala Ala Pro Thr Thr Gly Thr
            20                  25

<210> SEQ ID NO 68
<211> LENGTH: 33
<212> TYPE: PRT
<213> ORGANISM: Artificial Sequence
<220> FEATURE:
<223> OTHER INFORMATION: Made in Lab - Altered AAV capsid protein
      sequence

<400> SEQUENCE: 68

Ala Thr Asn Asn Leu Ala Leu Gly Glu Thr Thr Arg Pro Ala Gln Asn
1               5                   10                  15

Leu Gln Arg Gly Asn Arg Gln Ala Ala Thr Ala Ala Pro Thr Thr Gly
            20                  25                  30

Thr

<210> SEQ ID NO 69
<211> LENGTH: 42
<212> TYPE: PRT
<213> ORGANISM: Adeno-associated virus 2

<400> SEQUENCE: 69

Pro Val Ala Thr Glu Gln Tyr Gly Ser Val Ser Thr Asn Leu Gln Arg
1               5                   10                  15

Gly Asn Arg Gln Ala Ala Thr Ala Asp Val Asn Thr Gln Gly Val Leu
            20                  25                  30

Pro Gly Met Val Trp Gln Asp Arg Asp Val
            35                  40

```
<210> SEQ ID NO 70
<211> LENGTH: 42
<212> TYPE: PRT
<213> ORGANISM: Adeno-associated virus 1

<400> SEQUENCE: 70

Pro Val Ala Thr Glu Arg Phe Gly Thr Val Ala Val Asn Phe Gln Ser
1               5                   10                  15

Ser Ser Thr Asp Pro Ala Thr Gly Asp Val His Ala Met Gly Ala Leu
            20                  25                  30

Pro Gly Met Val Trp Gln Asp Arg Asp Val
        35                  40

<210> SEQ ID NO 71
<211> LENGTH: 42
<212> TYPE: PRT
<213> ORGANISM: Adeno-associated virus 5

<400> SEQUENCE: 71

Arg Val Ala Tyr Asn Val Gly Gly Gln Trp Met Ala Thr Asn Asn Gln
1               5                   10                  15

Ser Ser Thr Thr Ala Pro Ala Thr Gly Thr Tyr Asn Leu Gln Glu Ile
            20                  25                  30

Val Pro Gly Ser Val Met Glu Arg Asp Val
        35                  40

<210> SEQ ID NO 72
<211> LENGTH: 42
<212> TYPE: PRT
<213> ORGANISM: Adeno-associated virus 6

<400> SEQUENCE: 72

Pro Val Ala Thr Glu Arg Phe Gly Thr Val Ala Val Asn Leu Gln Ser
1               5                   10                  15

Ser Ser Thr Asp Pro Ala Thr Gly Asp Val His Val Met Gly Ala Leu
            20                  25                  30

Pro Gly Met Val Trp Gln Asp Arg Asp Val
        35                  40

<210> SEQ ID NO 73
<211> LENGTH: 42
<212> TYPE: PRT
<213> ORGANISM: Adeno-associated virus 7

<400> SEQUENCE: 73

Pro Val Ala Thr Glu Glu Tyr Gly Ile Val Ser Ser Asn Leu Gln Ala
1               5                   10                  15

Ala Asn Thr Ala Ala Gln Thr Gln Val Val Asn Asn Gln Gly Ala Leu
            20                  25                  30

Pro Gly Met Val Trp Gln Asn Arg Asp Val
        35                  40

<210> SEQ ID NO 74
<211> LENGTH: 42
<212> TYPE: PRT
<213> ORGANISM: Adeno-associated virus 8

<400> SEQUENCE: 74

Pro Val Ala Thr Glu Glu Tyr Gly Ile Val Ala Asp Asn Leu Gln Gln
1               5                   10                  15
```

```
Gln Asn Thr Ala Pro Gln Ile Gly Thr Val Asn Ser Gln Gly Ala Leu
            20                  25                  30

Pro Gly Met Val Trp Gln Asn Arg Asp Val
        35                  40

<210> SEQ ID NO 75
<211> LENGTH: 42
<212> TYPE: PRT
<213> ORGANISM: Adeno-associated virus 9

<400> SEQUENCE: 75

Pro Val Ala Thr Glu Ser Tyr Gly Gln Val Ala Thr Asn His Gln Ser
1               5                   10                  15

Ala Gln Ala Gln Ala Gln Thr Gly Trp Val Gln Asn Gln Gly Ile Leu
            20                  25                  30

Pro Gly Met Val Trp Gln Asp Arg Asp Val
        35                  40

<210> SEQ ID NO 76
<211> LENGTH: 42
<212> TYPE: PRT
<213> ORGANISM: Adeno-associated virus 10

<400> SEQUENCE: 76

Pro Val Ala Thr Glu Gln Tyr Gly Val Val Ala Asp Asn Leu Gln Gln
1               5                   10                  15

Ala Asn Thr Gly Pro Ile Val Gly Asn Val Asn Ser Gln Gly Ala Leu
            20                  25                  30

Pro Gly Met Val Trp Gln Asn Arg Asp Val
        35                  40
```